US010000694B2

(12) United States Patent
Parham et al.

(10) Patent No.: US 10,000,694 B2
(45) Date of Patent: Jun. 19, 2018

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Christof Pflumm, Darmstadt (DE); Jonas V. Kroeber, Frankfurt am Main (DE)

(73) Assignee: Merck Patent GmbH (DE)

( * ) Notice: Subject to any disclaimer, the term of this patent is extended or adjusted under 35 U.S.C. 154(b) by 17 days.

(21) Appl. No.: 15/108,899

(22) PCT Filed: Dec. 18, 2014

(86) PCT No.: PCT/EP2014/003417
§ 371 (c)(1),
(2) Date: Jun. 29, 2016

(87) PCT Pub. No.: WO2015/106789
PCT Pub. Date: Jul. 23, 2015

(65) Prior Publication Data
US 2016/0326429 A1    Nov. 10, 2016

(30) Foreign Application Priority Data
Jan. 17, 2014    (EP) .................................... 14000179

(51) Int. Cl.
*C07D 491/052* (2006.01)
*C07D 491/147* (2006.01)
*C09K 11/06* (2006.01)
*H05B 33/20* (2006.01)
*H01L 51/00* (2006.01)
*C09K 11/02* (2006.01)
*H01L 51/50* (2006.01)

(52) U.S. Cl.
CPC .......... *C09K 11/06* (2013.01); *C07D 491/052* (2013.01); *C07D 491/147* (2013.01); *C09K 11/025* (2013.01); *H01L 51/006* (2013.01); *H01L 51/0054* (2013.01); *H01L 51/0056* (2013.01); *H01L 51/0061* (2013.01); *H01L 51/0067* (2013.01); *H01L 51/0071* (2013.01); *H01L 51/0072* (2013.01); *H01L 51/0073* (2013.01); *H05B 33/20* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0052* (2013.01); *H01L 51/0058* (2013.01); *H01L 51/5012* (2013.01); *H01L 51/5016* (2013.01); *Y02E 10/549* (2013.01)

(58) Field of Classification Search
CPC ............ C07D 491/052; C07D 491/147; C09K 11/025; C09K 11/06; C09K 2211/1011; C09K 2211/1029; C09K 2211/1033; C09K 2211/1037; C09K 2211/1044; C09K 2211/1059; C09K 2211/1088; C09K 2211/1092; H01L 51/0071; H01L 51/0072; H01L 51/0073; H01L 51/0056; H01L 51/0067; H01L 51/0061; H01L 51/0054; H01L 51/006; H01L 51/0058; H01L 51/0052; H01L 51/501
See application file for complete search history.

(56) References Cited

U.S. PATENT DOCUMENTS

| 7,794,906 B2 * | 9/2010 | Wu ...................... G03G 5/0567 430/63 |
| 9,040,172 B2 | 5/2015 | Parham et al. |
| 2004/0092579 A1 | 5/2004 | Bokel et al. |
| 2008/0020234 A1 | 1/2008 | Ren et al. |
| 2009/0274970 A1 * | 11/2009 | Wu ...................... G03G 5/0521 430/58.6 |

FOREIGN PATENT DOCUMENTS

| CN | 1451001 A | 10/2003 |
| DE | 102009031021 A1 | 1/2011 |

OTHER PUBLICATIONS

Bringmann, G., et al., "*En route* to the first stereoselective synthesis of axially chiral biscarbazole alkaloids", Chemical Communications, No. 8, (2001), pp. 761-762.
International Search Report for PCT/EP2014/003417 dated Mar. 5, 2015.
Prabakaran, K., et al., "Palladium-Mediated Intramolecular C-O and C-C Coupling Reactions: An Efficient Synthesis of Benzannulated Oxazepino—and Pyranocarbazoles", Synlett, vol. 2011, No. 13, (2011), pp. 1835-1840.
Raju, B., et al., "Excited state properties of pre-twisted 7-diethylamino coumarinyl benzopyrano pyridine: an experimental and AM1 study", Journal of Photochemistry and Photobiology, A: Chemistry, vol. 116, No. 2, (1998), pp. 135-142.
Sreenivas, D., et al., "An Efficient Route for the Synthesis of Isochromenocarbazolones through Palladium-Catalyzed Intramolecular *ortho*-Arylation", Synthesis, vol. 2011, No. 19, (2011), pp. 3195-3203.
English Translation of Chinese Office Action for Chinese Application No. 201480073198.4, dated Feb. 6, 2018.

* cited by examiner

*Primary Examiner* — Karuna P Reddy
(74) *Attorney, Agent, or Firm* — Drinker Biddle & Reath LLP

(57) ABSTRACT

The invention relates to compounds which can be used in electronic devices, and to electronic devices, in particular organic electroluminescent devices, containing said compounds.

19 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2014/003417, filed Dec. 18, 2014, which claims benefit of European Application No. 14000179.3, filed Jan. 17, 2014, both of which are incorporated herein by reference in their entirety.

The present invention relates to materials for use in electronic devices, especially in organic electroluminescent devices, and to electronic devices, especially organic electroluminescent devices, comprising these materials.

The structure of organic electroluminescent devices (OLEDs) in which organic semiconductors are used as functional materials is described, for example, in U.S. Pat. No. 4,539,507, U.S. Pat. No. 5,151,629, EP 0676461 and WO 98/27136. Emitting materials used here are frequently organometallic complexes which exhibit phosphorescence rather than fluorescence. In general terms, there is still a need for improvement in OLEDs, especially also in OLEDs which exhibit triplet emission, i.e. phosphorescence, for example with regard to efficiency, operating voltage and lifetime.

The properties of phosphorescent OLEDs are not just determined by the triplet emitters used. Also of particular significance here are especially the other materials used, such as matrix materials, hole blocker materials, electron transport materials, hole transport materials and electron or exciton blocker materials. Improvements to these materials can thus also lead to improvements in the OLED properties.

According to the prior art, indolocarbazole derivatives, for example according to WO 2007/063754 or WO 2008/056746, or indenocarbazole derivatives, for example according to WO 2010/136109, are among the matrix materials used for phosphorescent emitters in organic electroluminescent devices. Further improvements are desirable here, especially in relation to the efficiency, lifetime and thermal stability of the materials.

It is an object of the present invention to provide compounds suitable for use in an OLED, especially as matrix material for phosphorescent emitters, but also as hole blocker material, as electron transport material or, if appropriate, as hole transport and/or electron blocker material. It is a further object of the present invention to provide further organic semiconductors for organic electroluminescent devices, in order thus to enable the person skilled in the art to have a greater possible choice of materials for the production of OLEDs.

It has been found that, surprisingly, particular compounds described below achieve this object and are of good suitability for use in OLEDs and lead to improvements in the organic electroluminescent device. These improvements relate particularly to the lifetime and/or the operating voltage. The present invention therefore provides these compounds and electronic devices, especially organic electroluminescent devices, comprising such compounds.

The present invention provides a compound of formula (1) or formula (2)

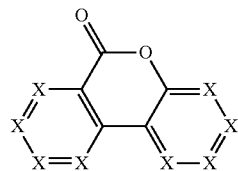

Formula (1)

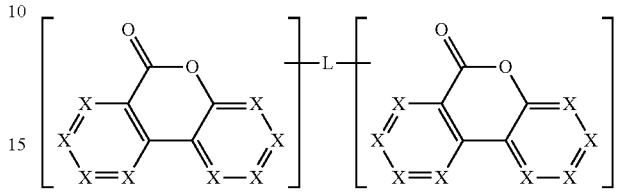

Formula (2)

where the symbols used are as follows:
X is the same or different at each instance and is CR or N or two adjacent X groups are a group of the following formula (3):

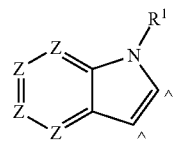

Formula (3)

where ^ indicates the corresponding adjacent X groups in the formula (1) or formula (2),
with the proviso that the compound of the formula (1) or formula (2) contains at least one group of the formula (3);
Z is the same or different at each instance and is CR or N;
L is a single bond or a bivalent group, where L is bonded in place of an R or $R^1$ group;
R is the same or different at each instance and is selected from the group consisting of H, D, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $Si(Ar^1)_3$, $Si(R^2)_3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $R^2C=CR^2$, $C≡C$, $Si(R^2)_2$, $C=O$, $C=S$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 60 aromatic ring atoms and may be substituted in each case by one or more $R^2$ radicals, an aryloxy or heteroaryloxy group which has 5 to 60 aromatic ring atoms and may be substituted by one or more $R^2$ radicals; at the same time, it is optionally possible for two adjacent $R^1$ substituents to form a monocyclic or polycyclic, aliphatic, aromatic or heteroaromatic ring system which may be substituted by one or more $R^2$ radicals;
$R^1$ is the same or different at each instance and is selected from the group consisting of an aromatic or heteroaromatic ring system which has 5 to 60 aromatic ring atoms and may be substituted in each case by one or more $R^2$ radicals;

Ar¹ is the same or different at each instance and is an aromatic or heteroaromatic ring system which has 5-30 aromatic ring atoms and may be substituted by one or more nonaromatic R² radicals; at the same time, two Ar¹ radicals bonded to the same nitrogen atom or phosphorus atom may also be bridged to one another by a single bond or a bridge selected from N(R²), C(R²)₂, O and S;

R² is the same or different at each instance and is selected from the group consisting of H, D, F, CN, an aliphatic hydrocarbyl radical having 1 to 20 carbon atoms and an aromatic or heteroaromatic ring system having 5 to 30 aromatic ring atoms in which one or more hydrogen atoms may be replaced by D, F, Cl, Br, I or CN, where two or more adjacent R² substituents together may form a mono- or polycyclic, aliphatic ring system.

When an L group is attached in formula (2), the corresponding X or Z group is CR, and the L group in each case is bonded in place of the R group, or the L group is bonded to the nitrogen atom in formula (3) in place of R.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or CH₂ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent CH₂ groups may be replaced by the abovementioned groups; in addition, it is also possible for one or more hydrogen atoms to be replaced by D, F, Cl, Br, I, CN or NO₂, preferably F, Cl or CN, further preferably F or CN, especially preferably CN.

An aromatic or heteroaromatic ring system which has 5-60 aromatic ring atoms and may also be substituted in each case by the abovementioned R² radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

Dibenzopyranone has the following structure:

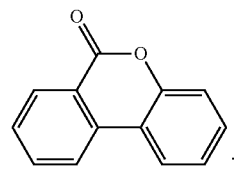 [SMILES: O=c1oc2ccccc2c2ccccc12]

When reference is made to dibenzopyranone in the description which follows, however, this shall refer not just to the abovementioned compound but also to derivatives in which one or more of the carbon atoms have been replaced by nitrogen atoms.

Adjacent radicals or adjacent substituents in the context of the present application are understood to mean substituents which are bonded to carbon atoms that are in turn bonded directly to one another, or substituents bonded to the same carbon atom.

The group of the formula (3) may be attached in any positions in the compound of the formula (1) or (2).

In a preferred embodiment of the invention, each of the two cycles of the dibenzopyranone in formula (1) contains not more than one group of the formula (3), such that the compound of the formula (1) contains a total of one or two groups of the formula (3). In a particularly preferred embodiment of the present invention, the compound of the formula (1) contains exactly one group of the formula (3). In a further preferred embodiment of the invention, each of the cycles of the dibenzopyranone in formula (2) contains not more than one group of the formula (3). In a particularly preferred embodiment of the present invention, each dibenzopyranone unit in the compound of the formula (2) contains exactly one group of the formula (3), such that the compound of the formula (2) contains a total of two groups of the formula (3).

In structures of the formula (2) containing two dibenzopyranone units, these dibenzopyranone units are bonded to one another via an L group, where L may be bonded at any desired positions. At the same time, it is also possible that L is bonded not to the dibenzopyranone unit itself, but also, for example, to the group of the formula (3).

Preferably, the X symbols which are not a group of the formula (3) are the same or different at each instance and are CR or N, where not more than one X group per cycle is N. Additionally preferably, adjacent R radicals present on X do not form an aromatic ring with one another. More preferably, the X symbols which are not a group of the formula (3) are the same or different at each instance and are CR, where adjacent R radicals preferably do not form an aromatic ring with one another.

A preferred embodiment of the compounds of the formula (1) concerns compounds of the following formula (4):

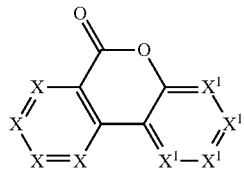

Formula (4)

where X is as defined above and $X^1$ is the same or different at each instance and is CR or N, i.e. the group of the formula (3) is bonded on the carbonyl side of the dibenzopyranone.

A further preferred embodiment of the compounds of the formula (1) concerns compounds of the following formula (5):

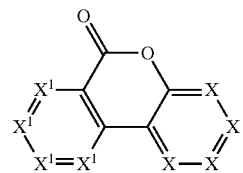

Formula (5)

where X and $X^1$ are as defined above, i.e. the group of the formula (3) is bonded on the oxygen side of the dibenzopyranone.

Preferred embodiments of the formula (1) are therefore the compounds of the following formulae (6) to (17):

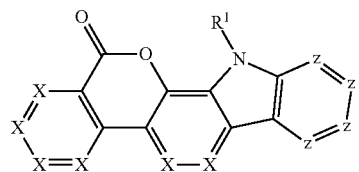

Formula (6)

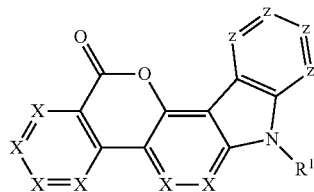

Formula (7)

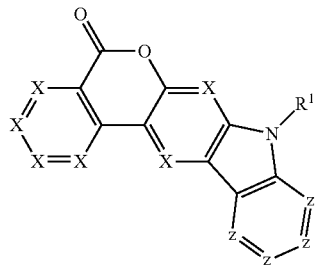

Formula (8)

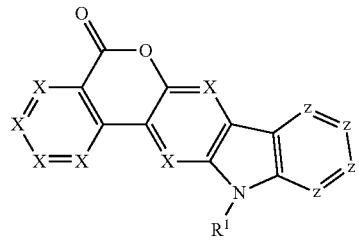

Formula (9)

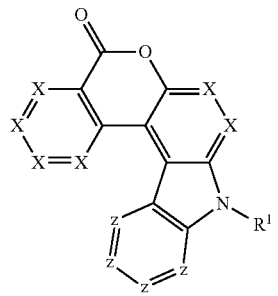

Formula (10)

Formula (11)
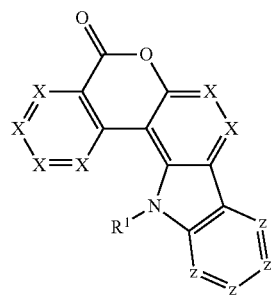
Formula (12)
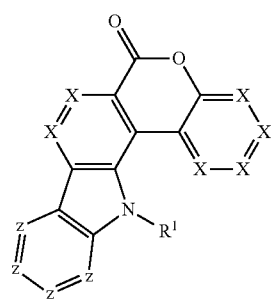
Formula (13)
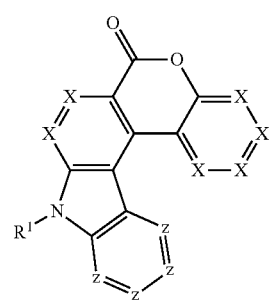
Formula (14)
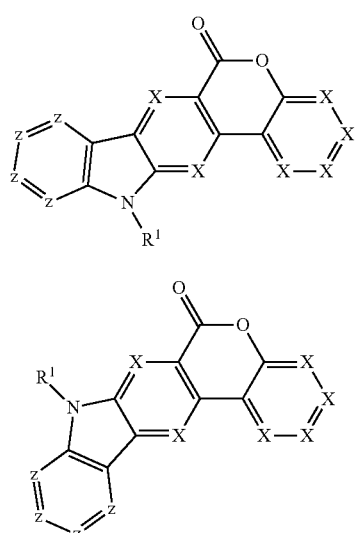
Formula (15)
Formula (16)
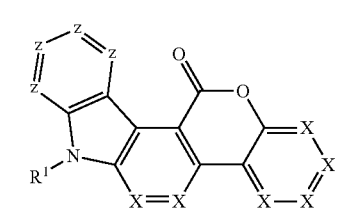
Formula (17)
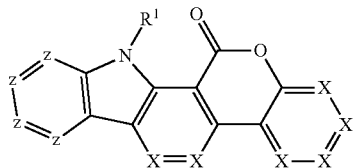
where the symbols used have the same definition as described above, and X is the same or different at each instance and is CR or N.
Particularly preferred embodiments of the formula (1) are the compounds of the following formulae (6a) to (17a):
Formula (6a)
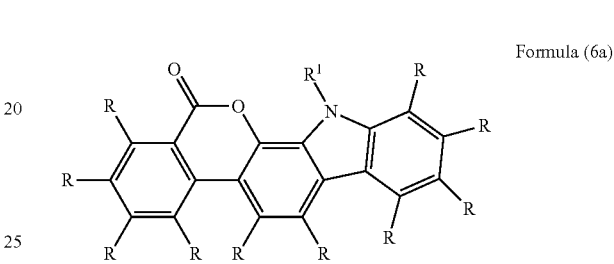
Formula (7a)
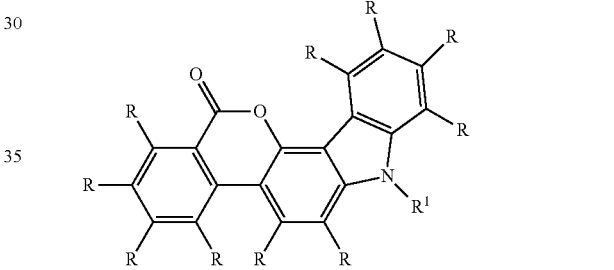
Formula (8a)
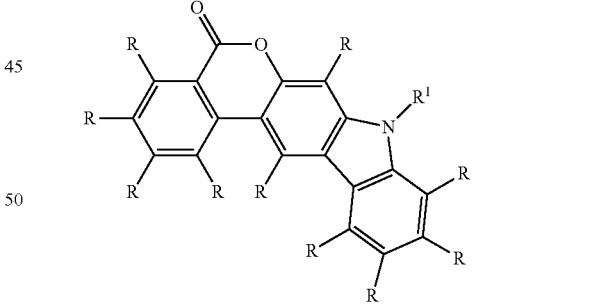
Formula (9a)
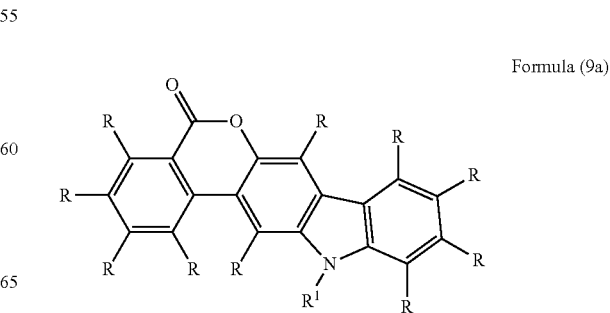

Formula (10a)

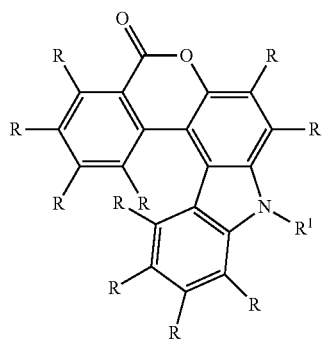

Formula (11a)

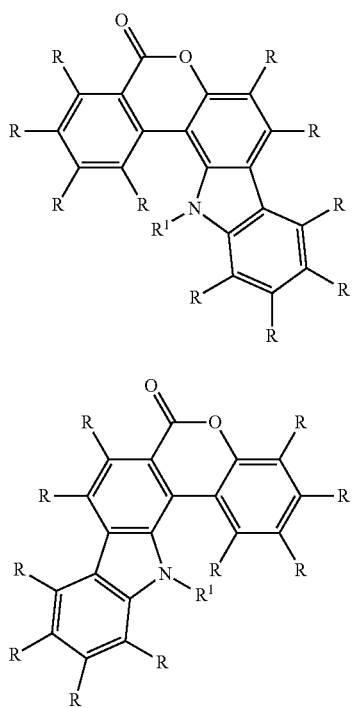

Formula (12a)

Formula (13a)

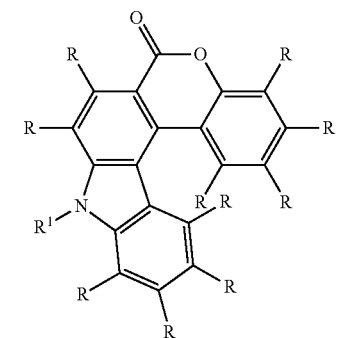

Formula (14a)

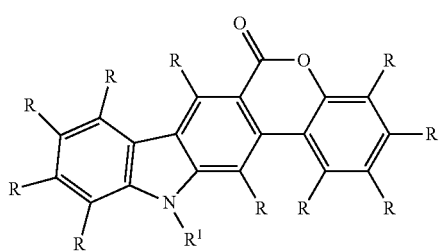

Formula (15a)

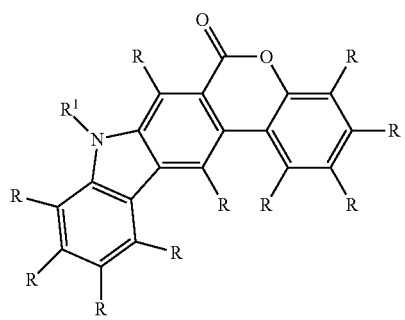

Formula (16a)

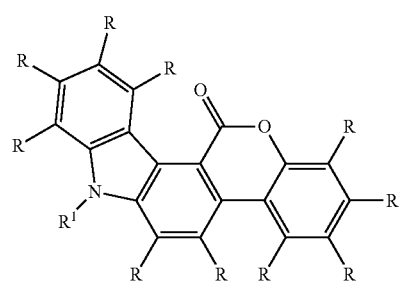

Formula (17a)

where the symbols used have the same definition as described above. Preference is given to the compounds of the formulae (6a), (10a) and (15a), particular preference being given to the compound of the formula (15a).

Very particularly preferred embodiments of the formula (1) are the compounds of the following formulae (6b) to (17b):

Formula (6b)

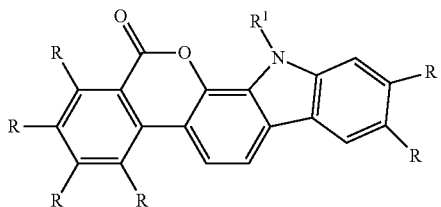

Formula (7b)

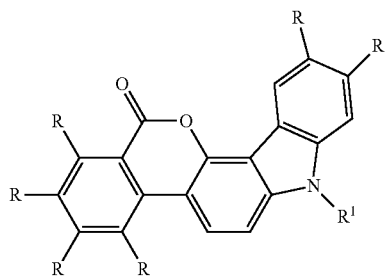

Formula (8b)
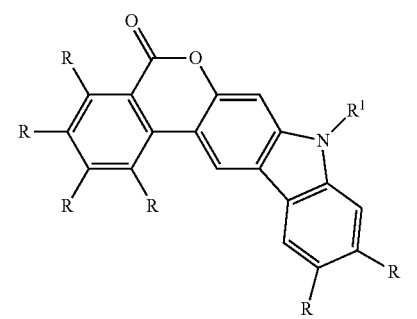

Formula (9b)
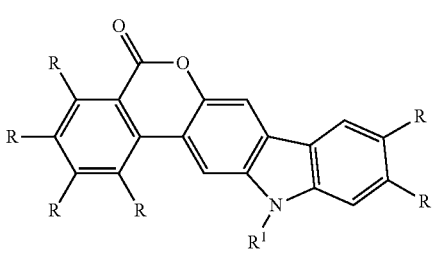

Formula (10b)
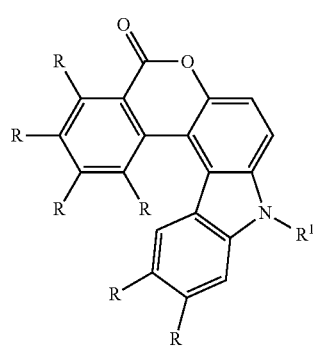

Formula (11b)
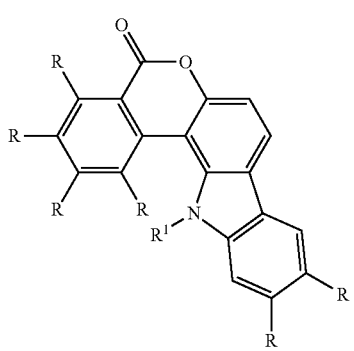

Formula (12b)
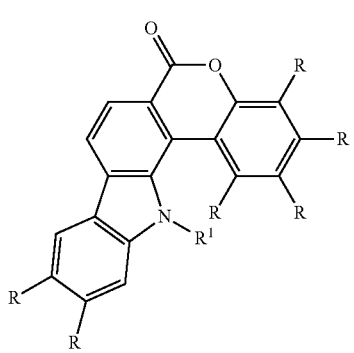

Formula (13b)
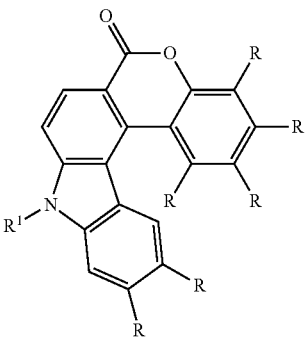

Formula (14b)
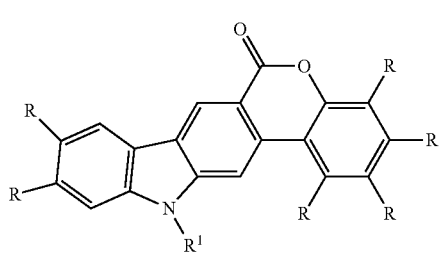

Formula (15b)
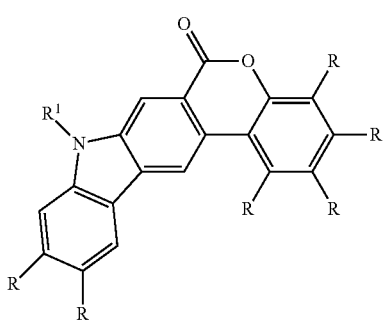

Formula (16b)
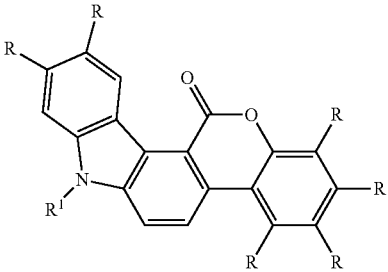

Formula (17b)
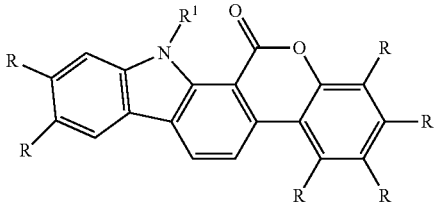

where the symbols used have the same definition as described above. Preference is given to the compounds of the formulae (6b), (10b) and (15b), particular preference being given to the compound of the formula (15b).

Preferred embodiments of the formula (2) correspond to those of the above-detailed preferred embodiments of the formula (1), where two such units in each case are joined to one another via an L group which may be a single bond or a bivalent group.

In preferred compounds of the formula (2), the bivalent L group is bonded to the groups of the formula (3), especially to the nitrogen atom of the formula (3), meaning that L is attached in place of the $R^1$ group, or to the carbon atom para to the nitrogen atom. This is shown schematically in the following formulae (3a) and (3b):

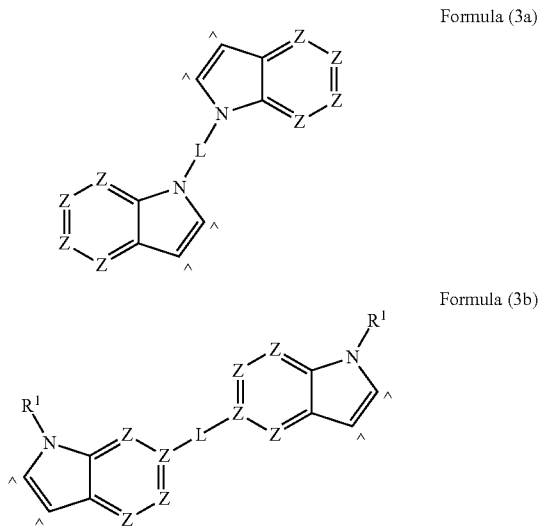

Formula (3a)

Formula (3b)

where these formulae are each incorporated correspondingly in the compound of the formula (2) and the symbols are as defined above.

In a preferred embodiment of the invention, L is selected from the group consisting of a single bond, a straight-chain alkylene group having 1 to 10 carbon atoms and a branched or cyclic alkylene group having 3 to 10 carbon atoms and an aromatic or heteroaromatic ring system which has 5 to 60 aromatic ring atoms and may be substituted by one or more nonaromatic $R^2$ radicals. In a particularly preferred embodiment of the invention, L is selected from the group consisting of a single bond and an aromatic or heteroaromatic ring system which has 5 to 30 aromatic ring atoms, preferably 5 to 24 aromatic ring atoms and more preferably 6 to 18 aromatic ring atoms and may be substituted by one or more nonaromatic $R^2$ radicals.

In a preferred embodiment of the invention, R is the same or different at each instance and is selected from the group consisting of H, F, CN, $N(Ar^1)_2$, a straight-chain alkyl group having 1 to 10 carbon atoms, preferably having 1 to 4 carbon atoms, and a branched or cyclic alkyl group having 3 to 10 carbon atoms, preferably a branched alkyl group having 3 or 4 carbon atoms, and an aromatic or heteroaromatic ring system which has 5 to 30 aromatic ring atoms and may be substituted by one or more nonaromatic $R^2$ radicals. In a particularly preferred embodiment of the invention, R is the same or different at each instance and is selected from the group consisting of H, $N(Ar^1)_2$ and an aromatic or heteroaromatic ring system which has 5 to 30 aromatic ring atoms and may be substituted by one or more nonaromatic $R^2$ radicals. When the compound of the invention is used as monomer for production of a polymer, it may also be preferable when two R substituents are Br or I and the polymerization is conducted via these groups. It may likewise be preferable in this case when one of the R substituents is an alkenyl group, a styryl group, an acrylate group, an oxetane group or an oxirane group and the polymerization is conducted via this group.

In a further preferred embodiment of the invention, $R^1$ is the same or different at each instance and is selected from the group consisting of an aromatic or heteroaromatic ring system which has 5 to 30 aromatic ring atoms and may be substituted in each case by one or more $R^2$ radicals. More preferably, $R^1$ is the same or different at each instance and is selected from the group consisting of an aromatic or heteroaromatic ring system which has 5 to 24 aromatic ring atoms and may be substituted in each case by one or more $R^2$ radicals.

At the same time, in compounds which are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

Particularly preferred $R^1$ groups are selected from benzene, ortho-, meta- or para-biphenyl, ortho-, meta-, para- or branched terphenyl, ortho-, meta-, para- or branched quaterphenyl, 1-, 2-, 3- or 4-fluorenyl, 1-, 2-, 3- or 4-spirobifluorenyl, 1- or 2-naphthyl, pyrrole, furan, thiophene, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, anthracene, phenanthrene, triphenylene, pyrene, benzanthracene and combinations of two or three of the aforementioned groups, each of which may be substituted by one or more $R^2$ radicals. A combination of two or three of these groups leads, for example, to a phenylenetriazine group which may be substituted by one or more $R^2$ radicals. Further preferred $R^1$ groups are triaryl or -heteroaryl groups which may be substituted by one or more $R^2$ radicals.

When R is an aromatic or heteroaromatic ring system, this R is preferably the same or different at each instance and is selected from the same groups as specified above as preferred groups for $R^1$.

Particularly suitable structures R when R is an aromatic or heteroaromatic ring system, or $R^1$, are selected from the groups of the following formulae (R-1) to (R-34):

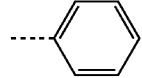

Formula (R-1)

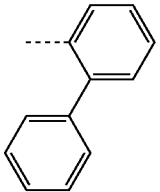

Formula (R-2)

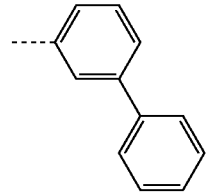

Formula (R-3)

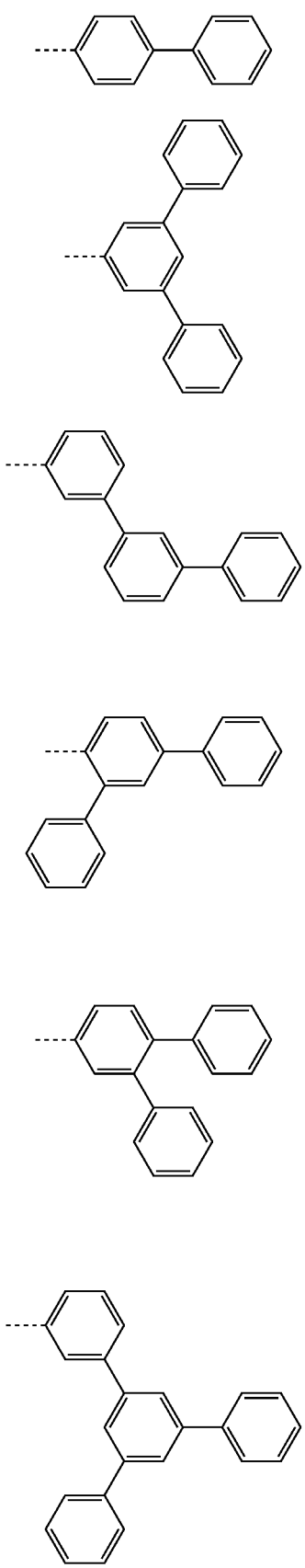

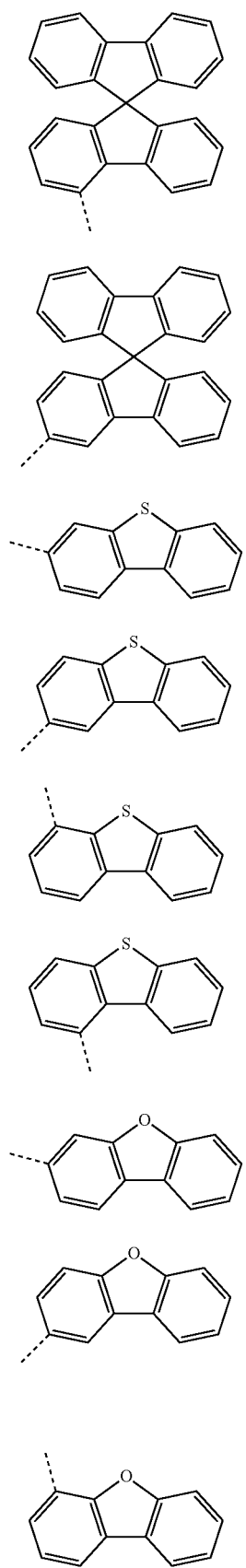

-continued

Formula (R-34)

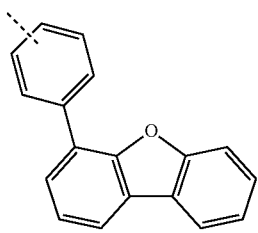

where the dotted bond indicates the bond to the base skeleton and the groups may each be substituted by one or more $R^2$ radicals, but are preferably unsubstituted.

For the use of the compounds of the invention as electron transport material, it is preferable when at least one of the R, $R^1$ and/or L groups is an electron-deficient heteroaromatic ring system or —C(=O)$Ar^1$ or —P(=O)($Ar^1$)$_2$. According to the invention, electron-deficient heteroaromatics are five-membered heteroaromatic rings having at least two heteroatoms or six-membered heteroaromatic rings, to each of which may be fused one or more aromatic or heteroaromatic groups. Examples of electron-deficient heteroaromatics are substituted or unsubstituted imidazoles, pyrazoles, thiazoles, oxazoles, oxadiazoles, triazoles, pyridines, pyrazines, pyrimidines, pyridazines, triazines, benzimidazoles, etc., especially those as described in detail hereinafter. Preferred R, $R^1$ and/or L groups are additionally also substituted or unsubstituted fused aryl groups, especially naphthalene, anthracene, pyrene, phenanthrene, triphenylene and benzanthracene.

When the compound of the invention is used as matrix material for a phosphorescent emitter or as an electron transport material, it is further preferable when at least one R, $R^1$ and/or L group is a simple aromatic group or an electron-deficient group. Especially suitable here are the above-detailed groups (R-1) to (R-34) and the following formulae (R-35) to (R-38) for R and $R^1$, or (L-1) or (L-2) for L, Formula (R-35)

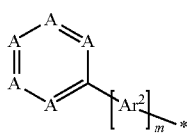

Formula (R-36)

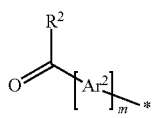

Formula (R-37)

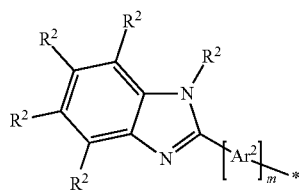

Formula (R-38)

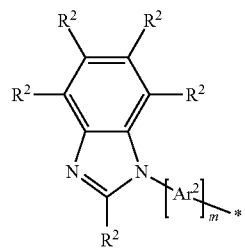

and/or at least one L group is preferably a group of the following formulae (L-1) or (L-2):

Formula (L-1)

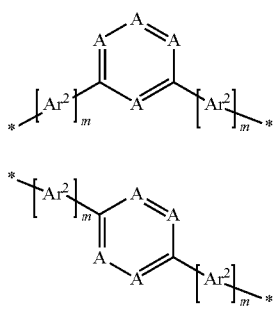

Formula (L-2)

where $R^2$ is as defined above, * indicates the position of the bond of the group and, in addition:

A is the same or different at each instance and is $CR^2$ or N, with the proviso that no, one, two or three A groups are N;

$Ar^2$ is the same or different at each instance and is a bivalent aromatic or heteroaromatic ring system which has 5 to 18 carbon atoms and may be substituted by one or more $R^2$ radicals;

m is the same or different at each instance and is 0 or 1.

Preferred embodiments of the above-detailed groups of the formula (R-35) are the groups of the following formulae (R-35a) to (R-35g), and particularly preferred L groups are the groups of the following formulae (L-1a) to (L-2c):

Formula (R-35a)

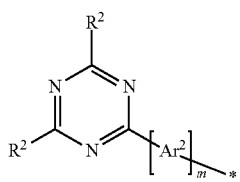

Formula (R-35b)

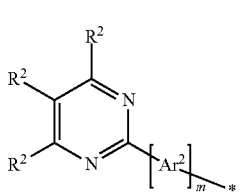

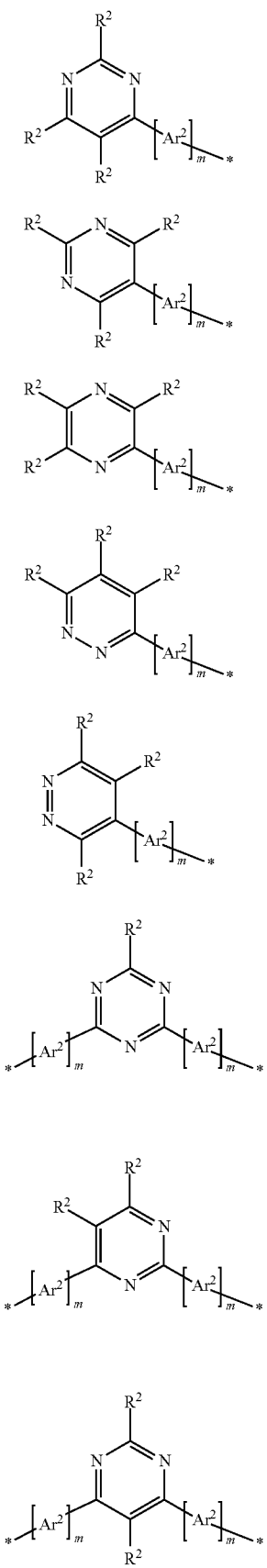

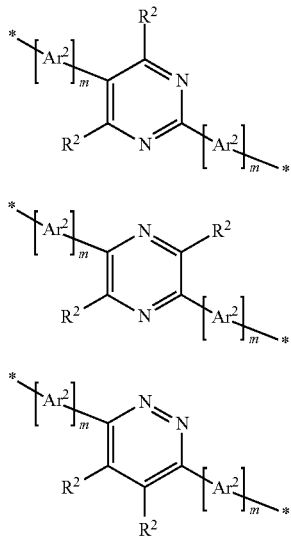

where the symbols and indices used have the definitions given above.

When R or $R^1$ is a group of the formula (R-35a), $R^2$ in this group is preferably an aromatic or heteroaromatic ring system which has 5 to 24 aromatic ring atoms and may be substituted by one or more alkyl groups having 1 to 10 carbon atoms, but is preferably unsubstituted, and is especially phenyl, biphenyl, especially ortho-, meta- or para-biphenyl, terphenyl, especially ortho-, meta-, para- or branched terphenyl, or quaterphenyl, especially ortho-, meta-, para- or branched quaterphenyl.

When R or $R^1$ is a group of the formula (R-35b) to (R-35g), $R^2$ in these groups is preferably the same or different at each instance and is H, D or an aromatic or heteroaromatic ring system which has 5 to 24 aromatic ring atoms and may be substituted by one or more alkyl groups having 1 to 10 carbon atoms, but is preferably unsubstituted, and is especially H or phenyl, biphenyl, especially ortho-, meta- or para-biphenyl, terphenyl, especially ortho-, meta-, para- or branched terphenyl, or quaterphenyl, especially ortho-, meta-, para- or branched quaterphenyl.

Further suitable substituents R or $R^1$, especially for the use of the compound of the invention as matrix material for a phosphorescent emitter, are selected from the group consisting of triaryl- or heteroarylamine derivatives, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives and dibenzothiophene derivatives, each of which may be substituted by one or more $R^2$ radicals, and/or at least one substituent R is —N(Ar$^1$)$_2$. These groups are preferably selected from the groups of the following formulae (R-39) to (R-63):

Formula (R-39)

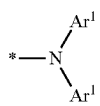

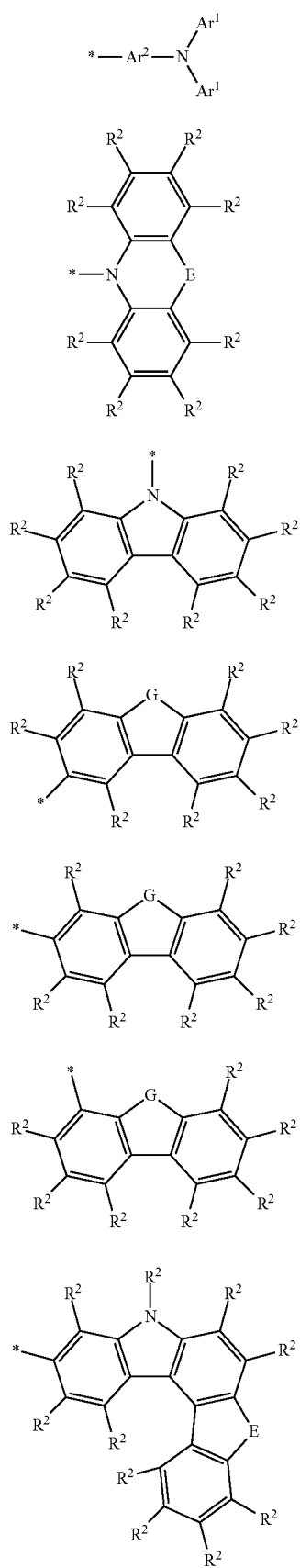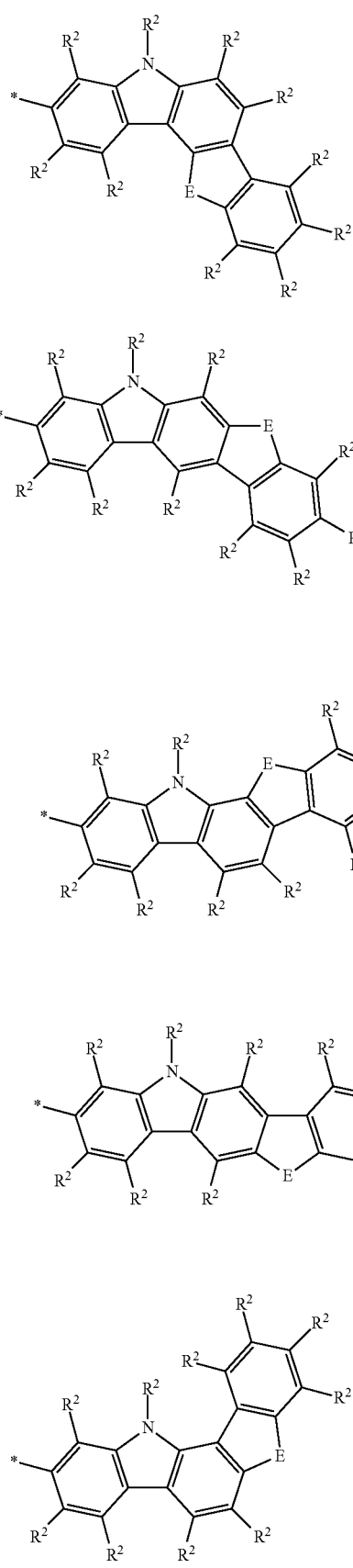

Formula (R-52)
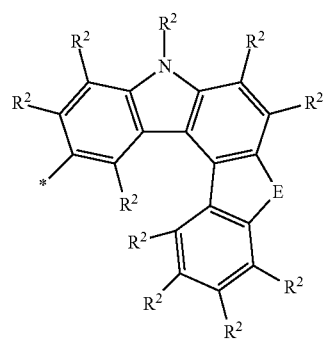
Formula (R-53)
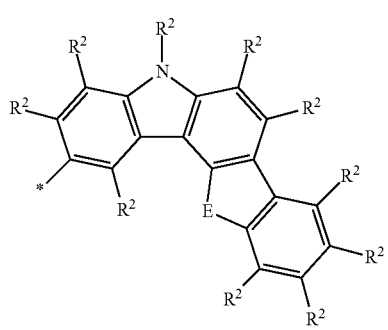
Formula (R-54)
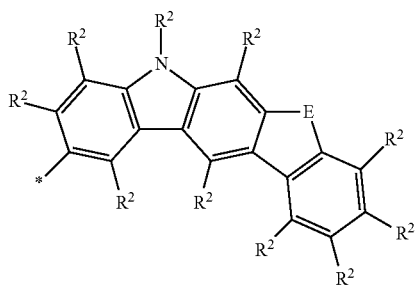
Formula (R-55)
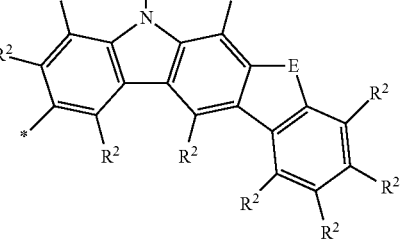
Formula (R-56)
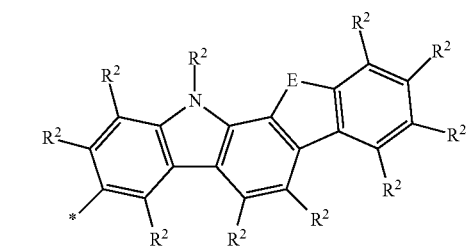
Formula (R-57)
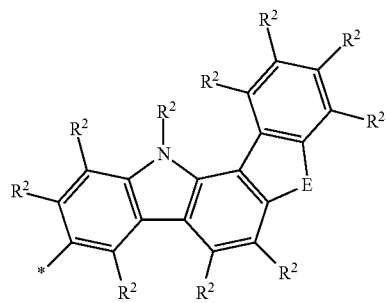
Formula (R-58)
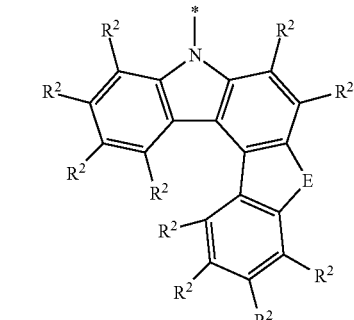
Formula (R-59)
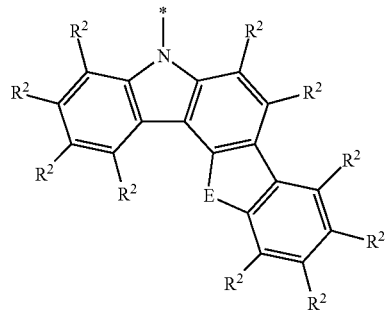
Formula (R-60)
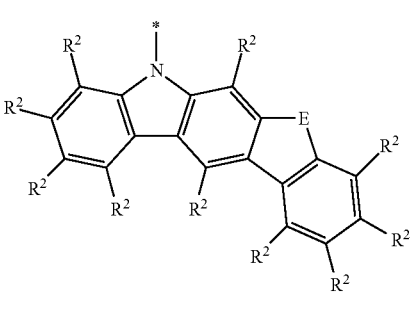
Formula (R-61)
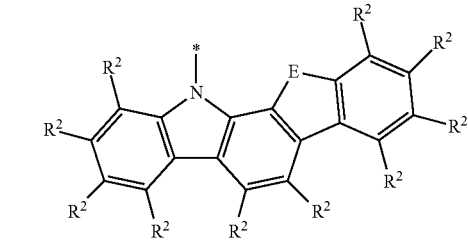

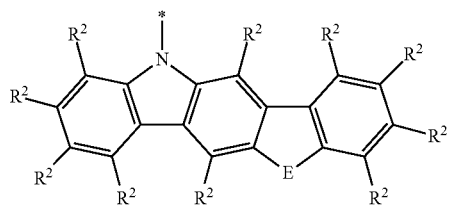

Formula (R-62)

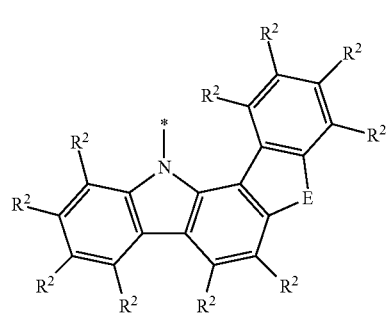

Formula (R-63)

where * indicates the position of the bond of the group, the symbols used are as defined above and, in addition:

E is selected from the group consisting of $C(R^2)_2$, $NR^2$, O and S;

G is selected from the group consisting of $NR^2$, O and S.

The abovementioned preferred embodiments may be combined with one another as desired. In a particularly preferred embodiment of the invention, the abovementioned preferences occur simultaneously.

When the compounds of the formula (1) or (2) or the preferred embodiments are used as matrix material for a phosphorescent emitter, it is further preferable when the compound does not contain any fused aryl or heteroaryl groups in which more than two aromatic or heteroaromatic six-membered rings are fused directly to one another. It is especially preferable when the R, $R^1$ and $R^2$ radicals do not contain any fused aryl or heteroaryl group in which two or more six-membered rings are fused directly to one another.

Examples of suitable compounds according to the above-detailed embodiments are the compounds detailed in the following table:

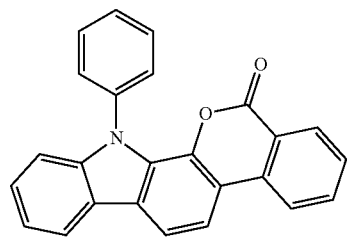 [SMILES: O=c1oc2c(ccc3c4ccccc4n(-c4ccccc4)c32)c2ccccc12]

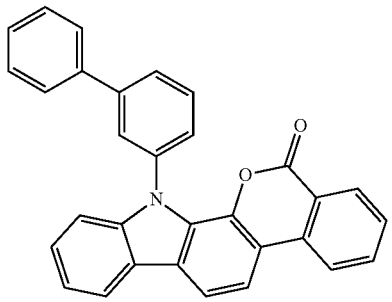 [SMILES: O=c1oc2c(ccc3c4ccccc4n(-c4cccc(-c5ccccc5)c4)c32)c2ccccc12]

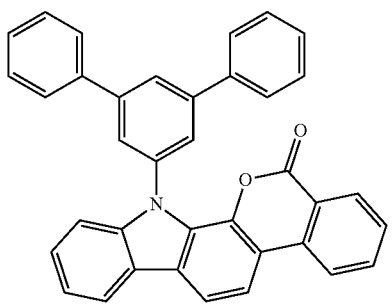 [SMILES: O=c1oc2c(ccc3c4ccccc4n(-c4cc(-c5ccccc5)cc(-c5ccccc5)c4)c32)c2ccccc12]

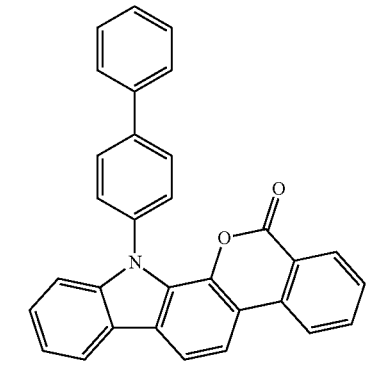 [SMILES: O=c1oc2c(ccc3c4ccccc4n(-c4ccc(-c5ccccc5)cc4)c32)c2ccccc12]

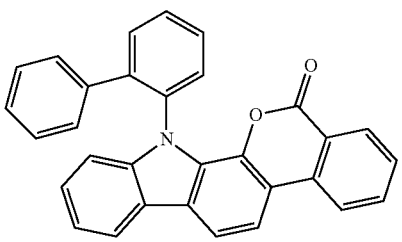 [SMILES: O=c1oc2c(ccc3c4ccccc4n(-c4ccccc4-c4ccccc4)c32)c2ccccc12]

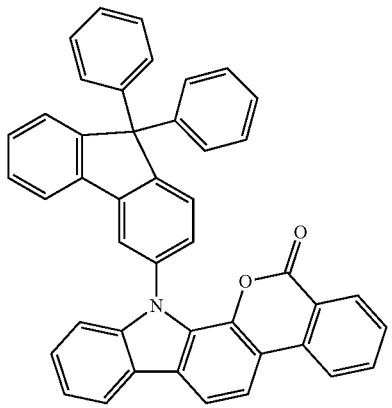 [SMILES: O=c1oc2c(ccc3c4ccccc4n(-c4ccc5c(c4)-c4ccccc4C5(c4ccccc4)c4ccccc4)c32)c2ccccc12]

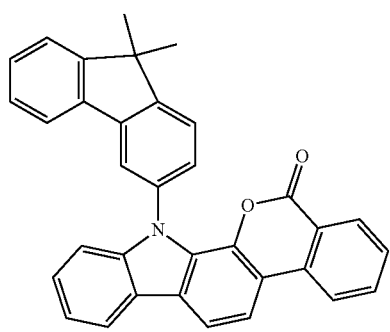 [SMILES: CC1(C)c2ccccc2-c2cc(-n3c4ccccc4c4ccc5c6ccccc6c(=O)oc5c43)ccc21]
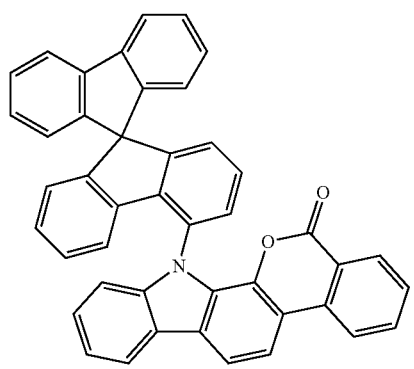 [SMILES: O=c1oc2c(ccc3c4ccccc4n(-c4cccc5c4-c4ccccc4C54c5ccccc5-c5ccccc54)c32)c2ccccc12]
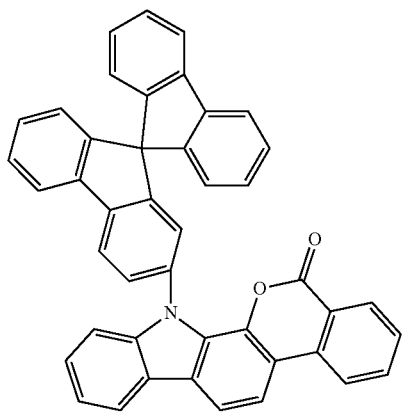 [SMILES: O=c1oc2c(ccc3c4ccccc4n(-c4ccc5c(c4)C4(c6ccccc6-c6ccccc64)c4ccccc4-5)c32)c2ccccc12]
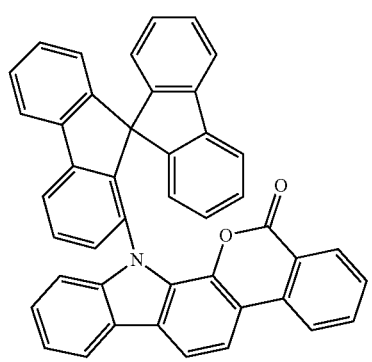 [SMILES: O=c1oc2c(ccc3c4ccccc4n(-c4cccc5c4C4(c6ccccc6-c6ccccc64)c4ccccc4-5)c32)c2ccccc12]
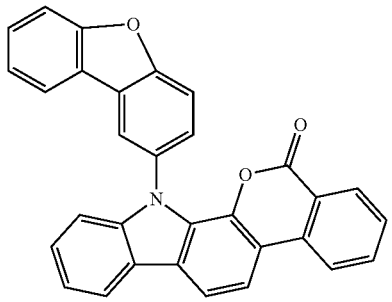 [SMILES: O=c1oc2c(ccc3c4ccccc4n(-c4ccc5oc6ccccc6c5c4)c32)c2ccccc12]
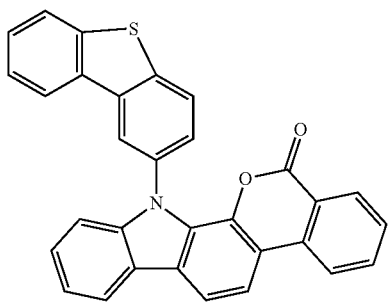 [SMILES: O=c1oc2c(ccc3c4ccccc4n(-c4ccc5sc6ccccc6c5c4)c32)c2ccccc12]
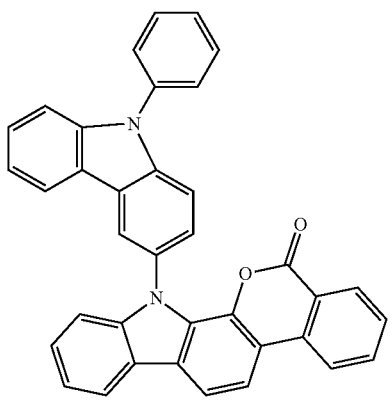 [SMILES: O=c1oc2c(ccc3c4ccccc4n(-c4ccc5c(c4)c4ccccc4n5-c4ccccc4)c32)c2ccccc12]
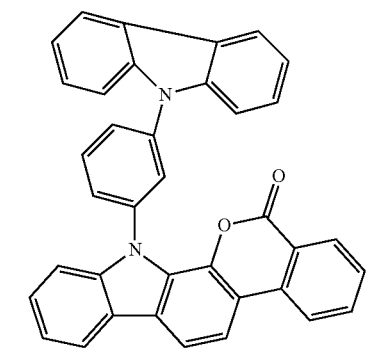 [SMILES: O=c1oc2c(ccc3c4ccccc4n(-c4cccc(-n5c6ccccc6c6ccccc65)c4)c32)c2ccccc12]

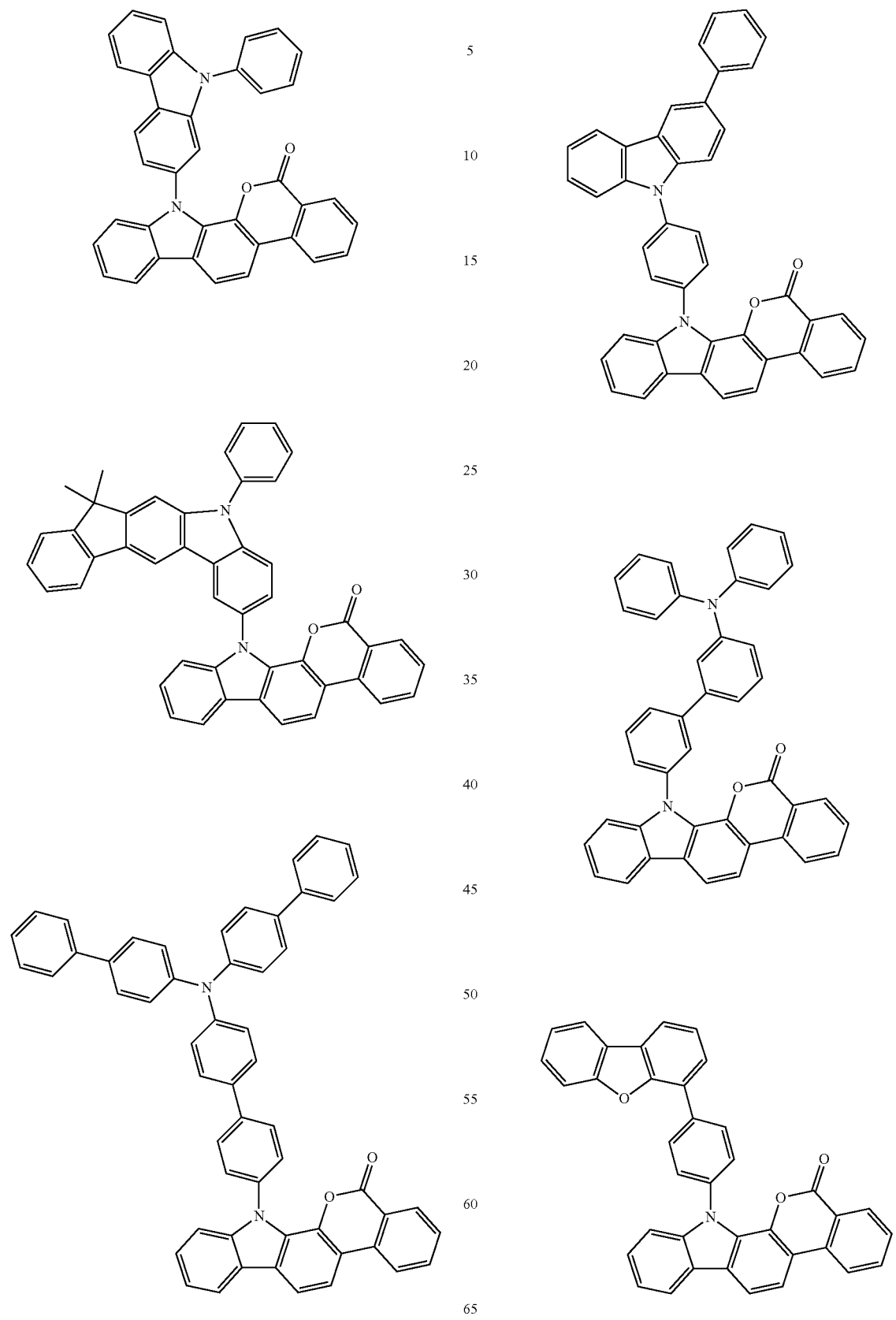

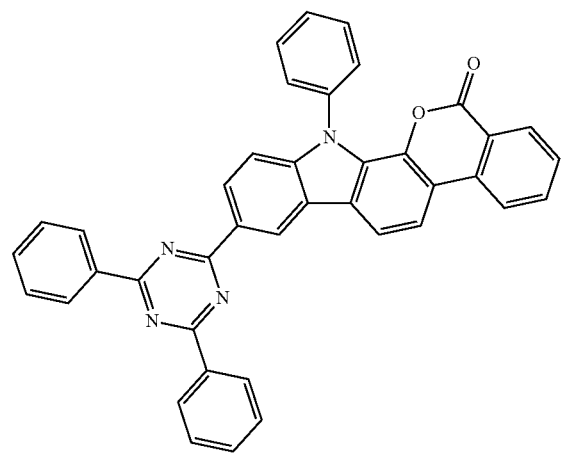 [SMILES: O=c1oc2c(ccc3c4cc(-c5nc(-c6ccccc6)nc(-c6ccccc6)n5)ccc4n(-c4ccccc4)c32)c2ccccc12]
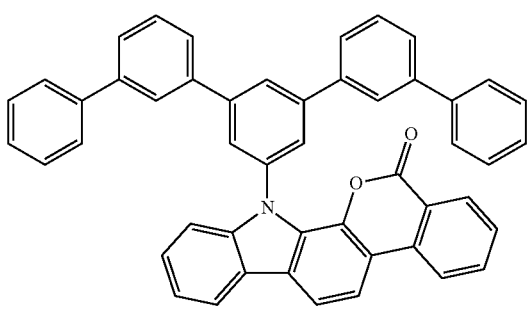
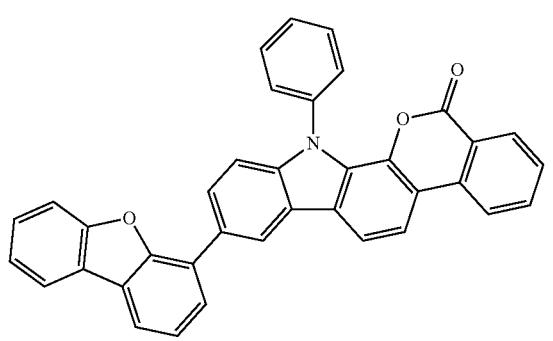 [SMILES: O=c1oc2c(ccc3c4cc(-c5cccc6c5oc5ccccc56)ccc4n(-c4ccccc4)c32)c2ccccc12]
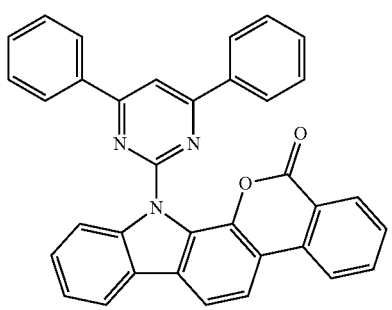
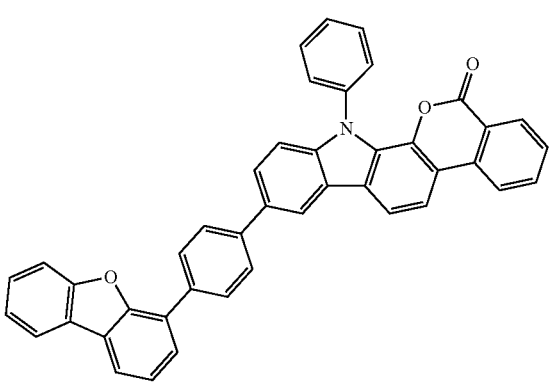 [SMILES: O=c1oc2c(ccc3c4cc(-c5ccc(-c6cccc7c6oc6ccccc67)cc5)ccc4n(-c4ccccc4)c32)c2ccccc12]
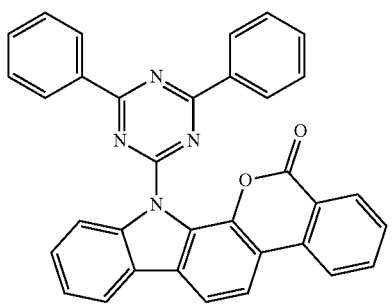
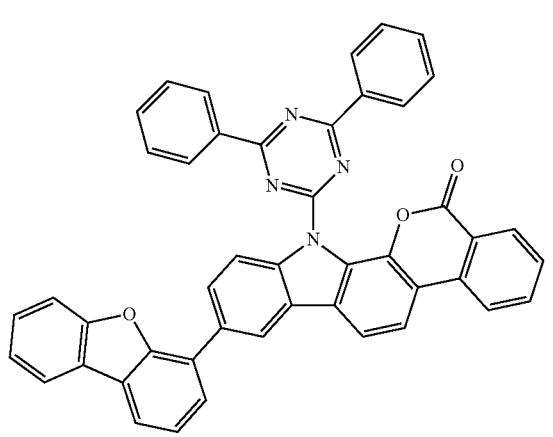 [SMILES: O=c1oc2c(ccc3c4cc(-c5cccc6c5oc5ccccc56)ccc4n(-c4nc(-c5ccccc5)nc(-c5ccccc5)n4)c32)c2ccccc12]
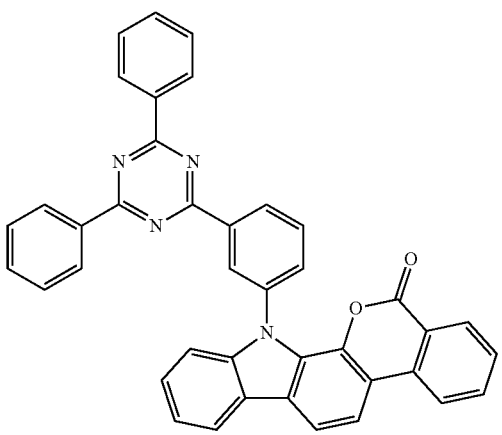 [SMILES: O=c1oc2c(ccc3c4ccccc4n(-c4cccc(-c5nc(-c6ccccc6)nc(-c6ccccc6)n5)c4)c32)c2ccccc12]

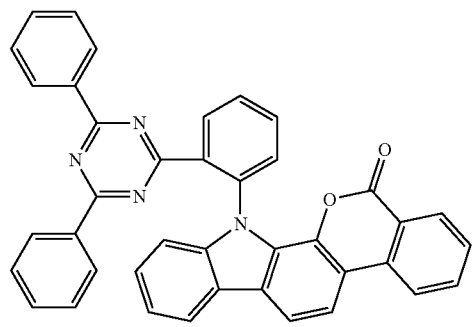 [SMILES: O=c1oc2c(ccc3c4ccccc4n(-c4ccccc4-c4nc(-c5ccccc5)nc(-c5ccccc5)n4)c32)c2ccccc12]
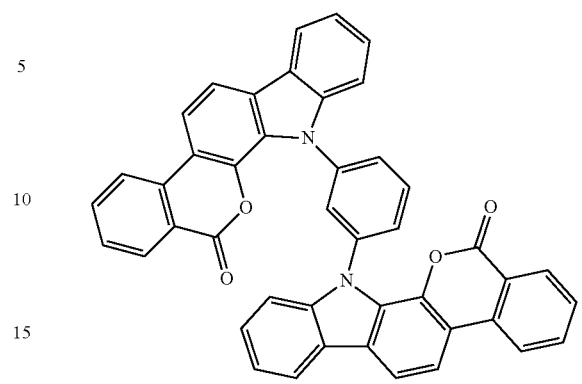
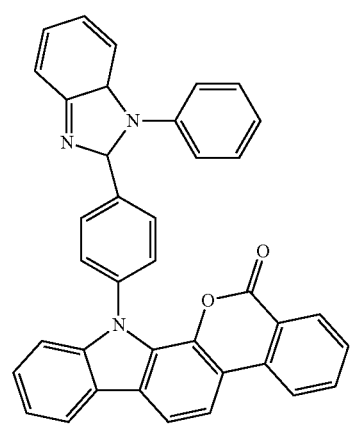 [SMILES: O=c1oc2c(ccc3c4ccccc4n(-c4ccc(C5N=C6C=CC=CC6N5c5ccccc5)cc4)c32)c2ccccc12]
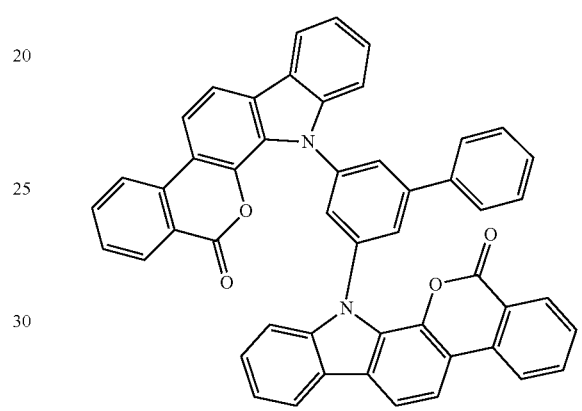
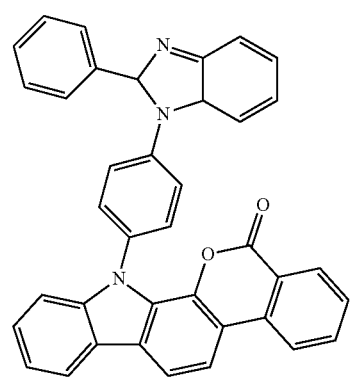 [SMILES: O=c1oc2c(ccc3c4ccccc4n(-c4ccc(N5C6C=CC=CC6=NC5c5ccccc5)cc4)c32)c2ccccc12]
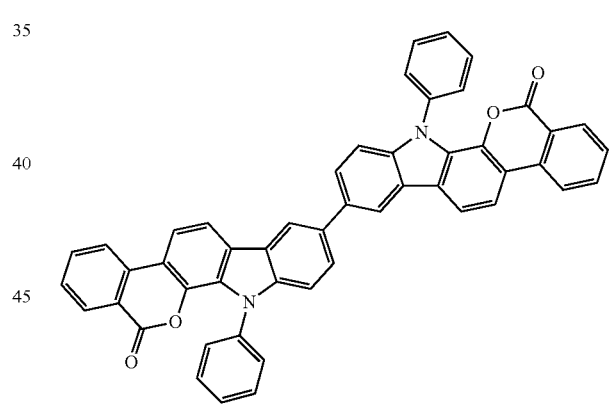
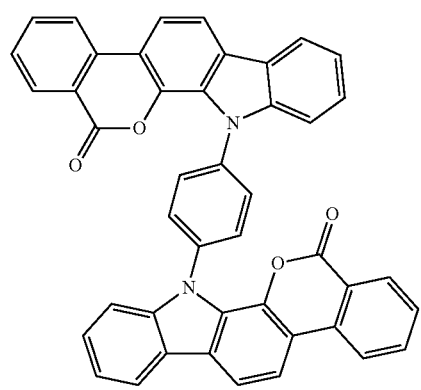 [SMILES: O=c1oc2c(ccc3c4ccccc4n(-c4ccc(-n5c6ccccc6c6ccc7c8ccccc8c(=O)oc7c65)cc4)c32)c2ccccc12]
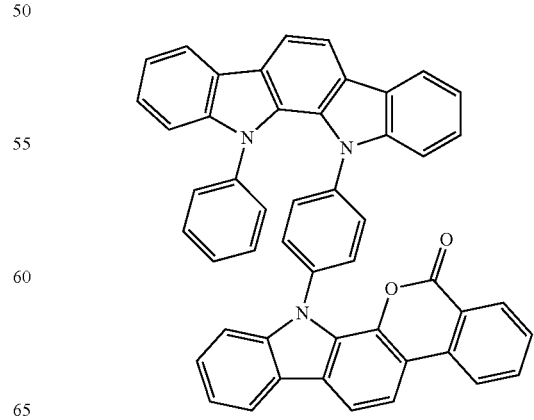

37
-continued
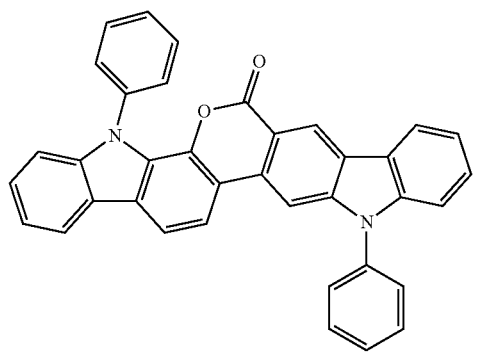 [SMILES: O=c1oc2c(ccc3c4ccccc4n(-c4ccccc4)c32)c2cc3c(cc12)c1ccccc1n3-c1ccccc1]
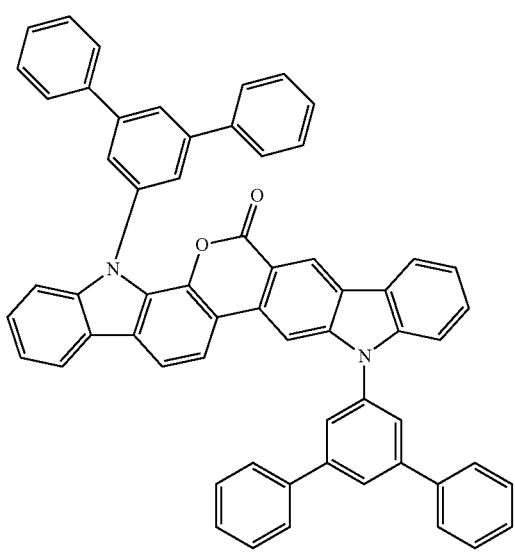 [SMILES: O=c1oc2c(ccc3c4ccccc4n(-c4cc(-c5ccccc5)cc(-c5ccccc5)c4)c32)c2cc3c(cc12)c1ccccc1n3-c1cc(-c2ccccc2)cc(-c2ccccc2)c1]
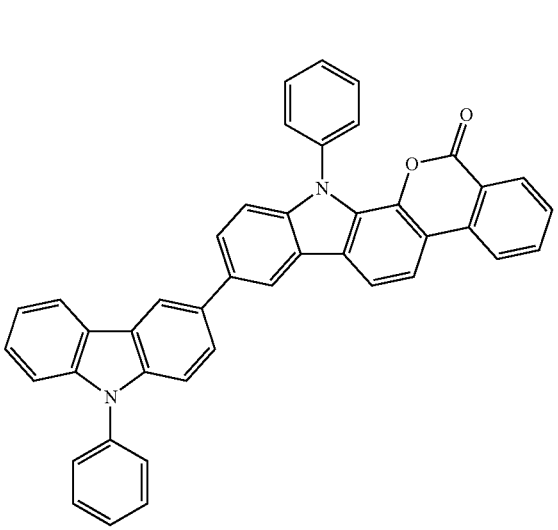 [SMILES: O=c1oc2c(ccc3c4cc(-c5ccc6c(c5)c5ccccc5n6-c5ccccc5)ccc4n(-c4ccccc4)c32)c2ccccc12]
38
-continued
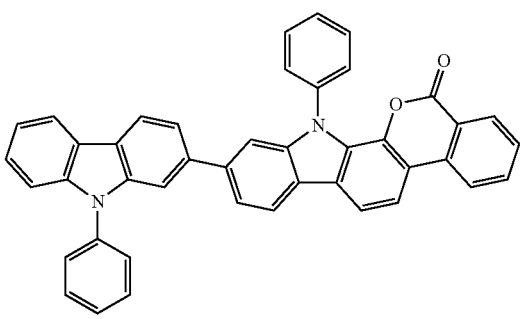 [SMILES: O=c1oc2c(ccc3c4ccc(-c5ccc6c7ccccc7n(-c7ccccc7)c6c5)cc4n(-c4ccccc4)c32)c2ccccc12]
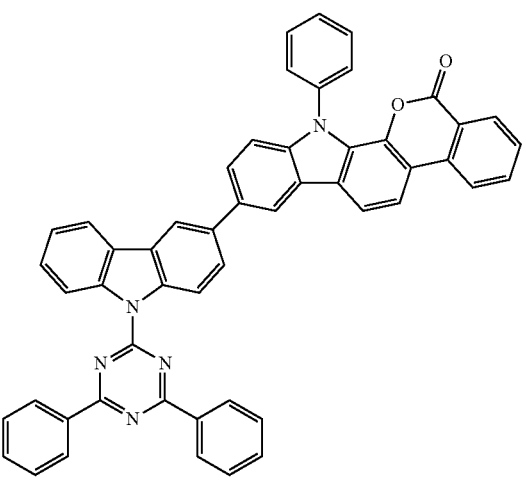 [SMILES: O=c1oc2c(ccc3c4cc(-c5ccc6c(c5)c5ccccc5n6-c5nc(-c6ccccc6)nc(-c6ccccc6)n5)ccc4n(-c4ccccc4)c32)c2ccccc12]
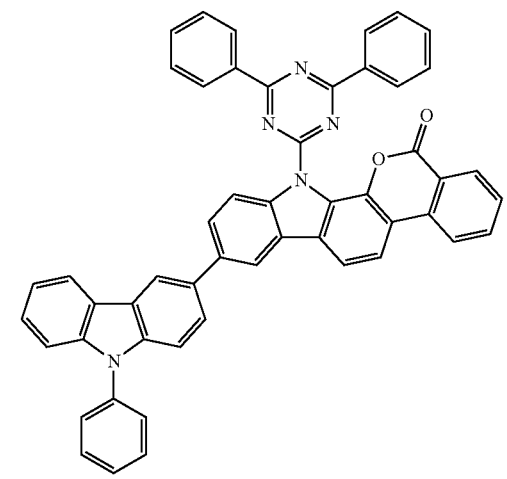 [SMILES: O=c1oc2c(ccc3c4cc(-c5ccc6c(c5)c5ccccc5n6-c5ccccc5)ccc4n(-c4nc(-c5ccccc5)nc(-c5ccccc5)n4)c32)c2ccccc12]

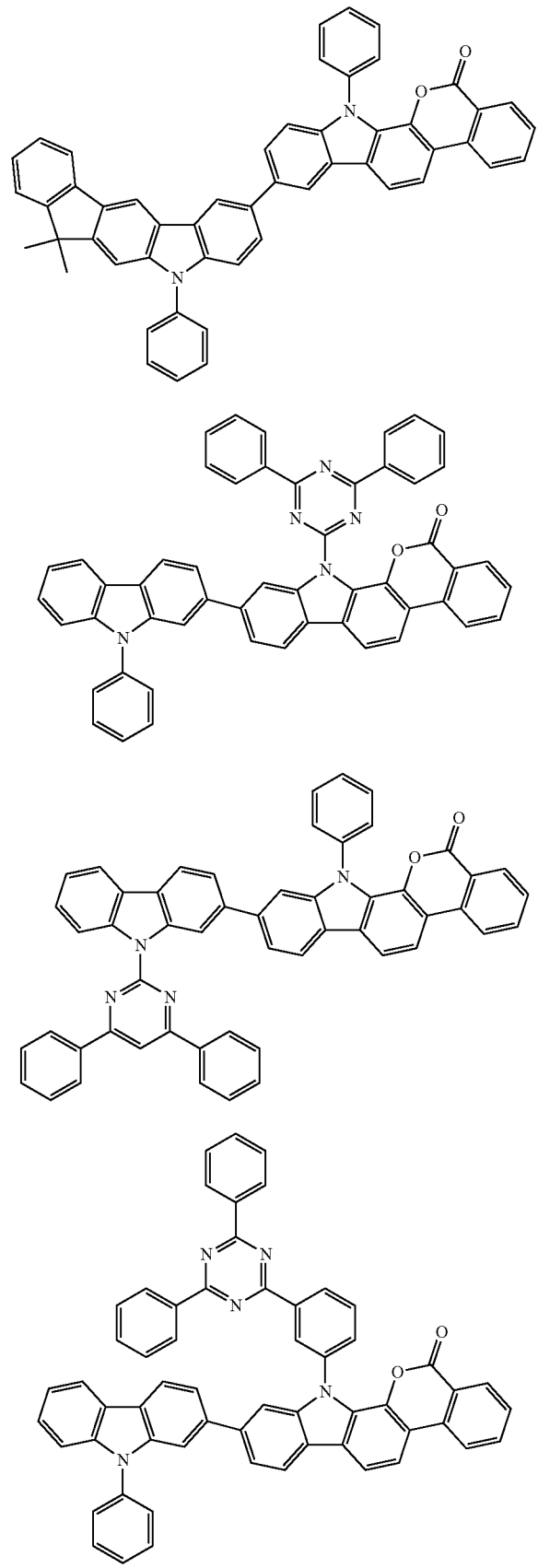
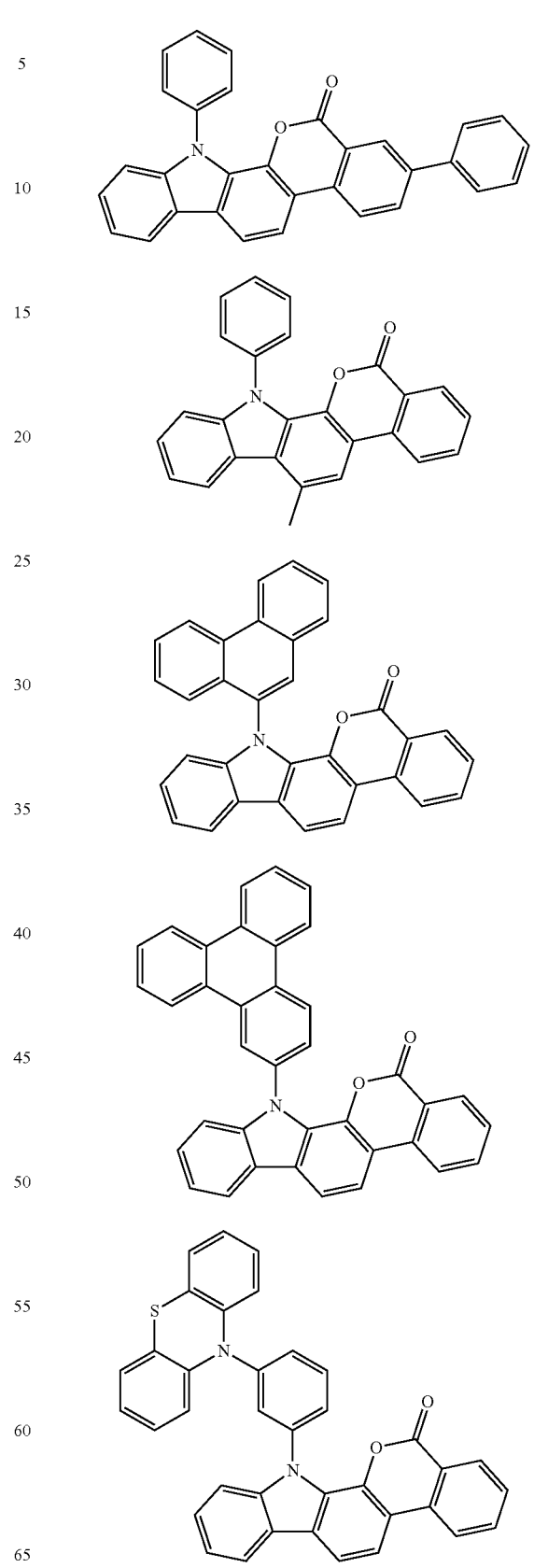

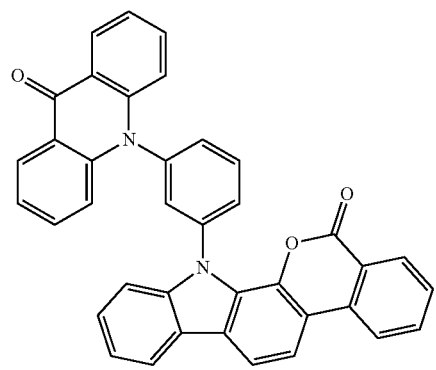 [SMILES: O=c1oc2c(ccc3c4ccccc4n(-c4cccc(-n5c6ccccc6c(=O)c6ccccc65)c4)c32)c2ccccc12]
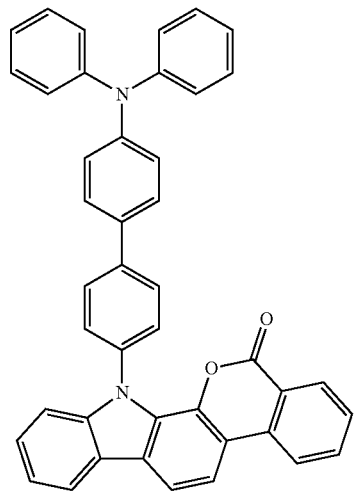
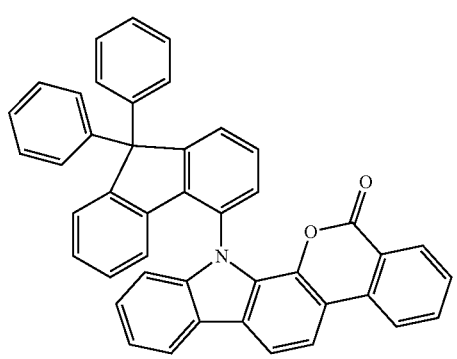 [SMILES: O=c1oc2c(ccc3c4ccccc4n(-c4cccc5c4-c4ccccc4C5(c4ccccc4)c4ccccc4)c32)c2ccccc12]
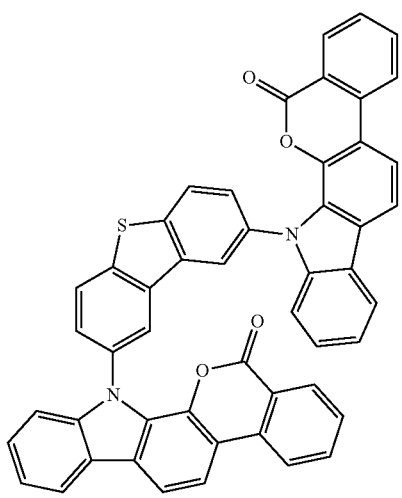
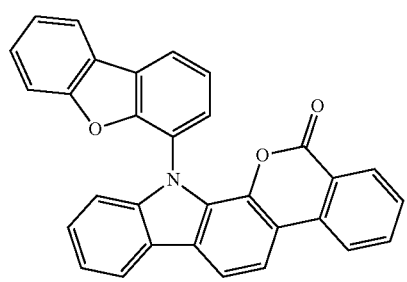 [SMILES: O=c1oc2c(ccc3c4ccccc4n(-c4cccc5c4oc4ccccc45)c32)c2ccccc12]
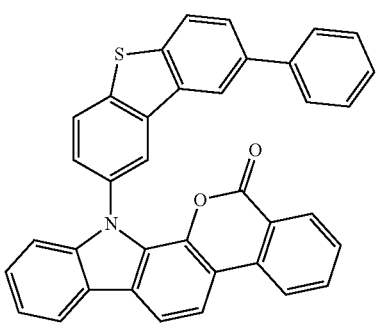
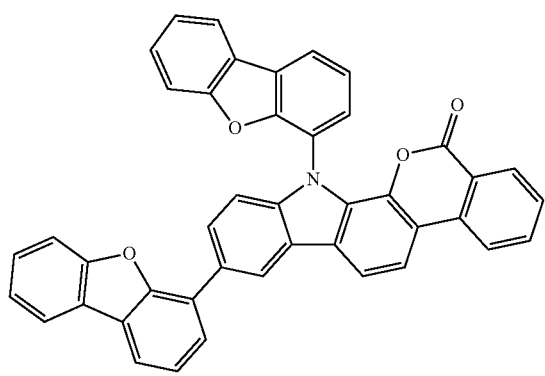 [SMILES: O=c1oc2c(ccc3c4cc(-c5cccc6c5oc5ccccc56)ccc4n(-c4cccc5c4oc4ccccc45)c32)c2ccccc12]
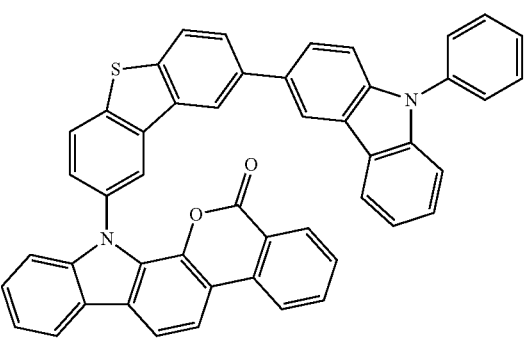 [SMILES: O=c1oc2c(ccc3c4ccccc4n(-c4ccc5sc6ccc(-c7ccc8c(c7)c7ccccc7n8-c7ccccc7)cc6c5c4)c32)c2ccccc12]

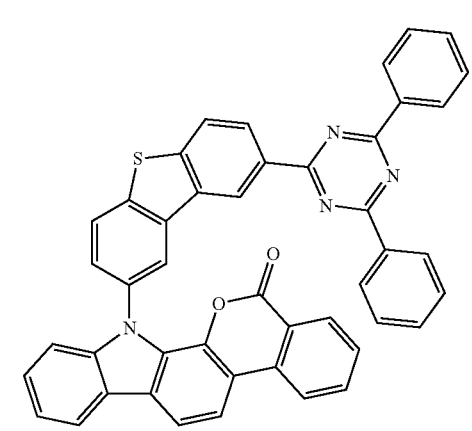 [SMILES: O=c1oc2c(ccc3c4ccccc4n(-c4ccc5sc6ccc(-c7nc(-c8ccccc8)nc(-c8ccccc8)n7)cc6c5c4)c32)c2ccccc12]
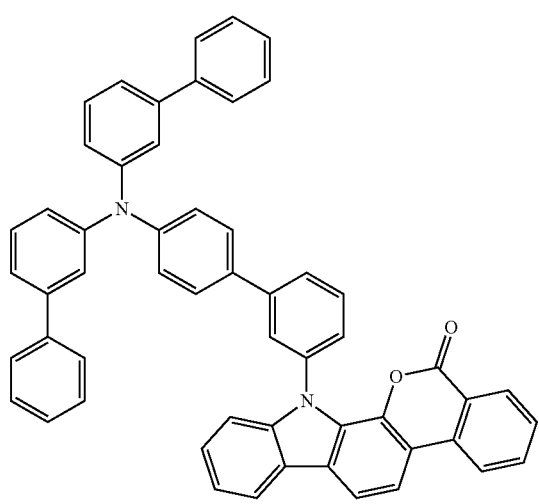 [SMILES: O=c1oc2c(ccc3c4ccccc4n(-c4cccc(-c5ccc(N(c6cccc(-c7ccccc7)c6)c6cccc(-c7ccccc7)c6)cc5)c4)c32)c2ccccc12]
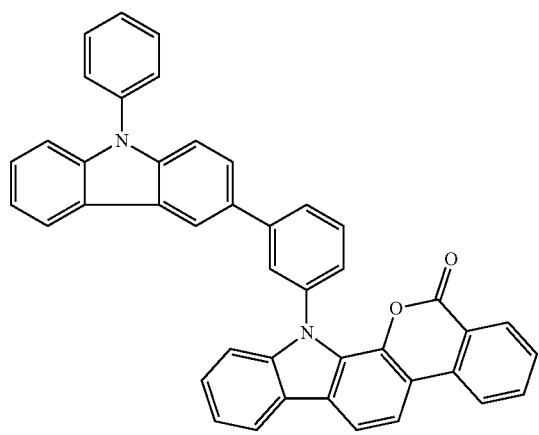 [SMILES: O=c1oc2c(ccc3c4ccccc4n(-c4cccc(-c5ccc6c(c5)c5ccccc5n6-c5ccccc5)c4)c32)c2ccccc12]
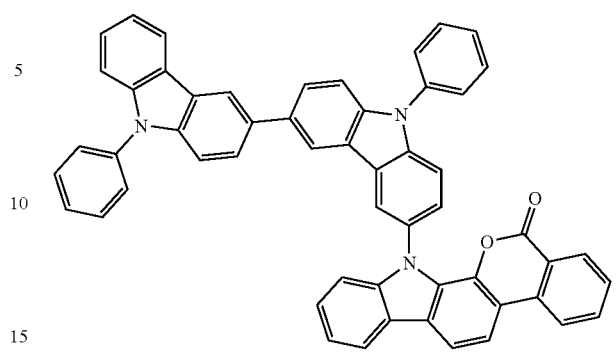
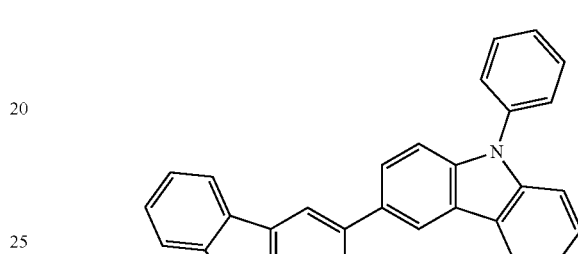
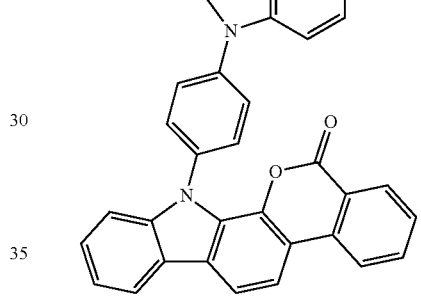
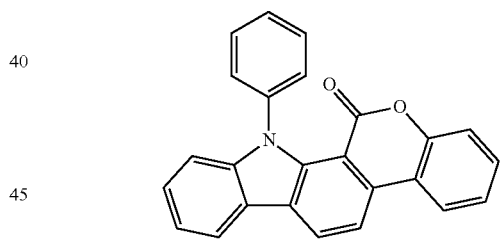
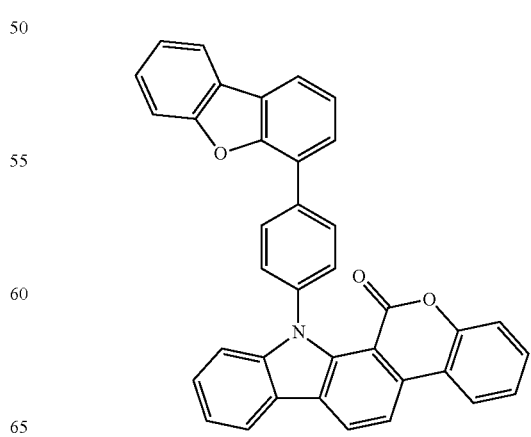

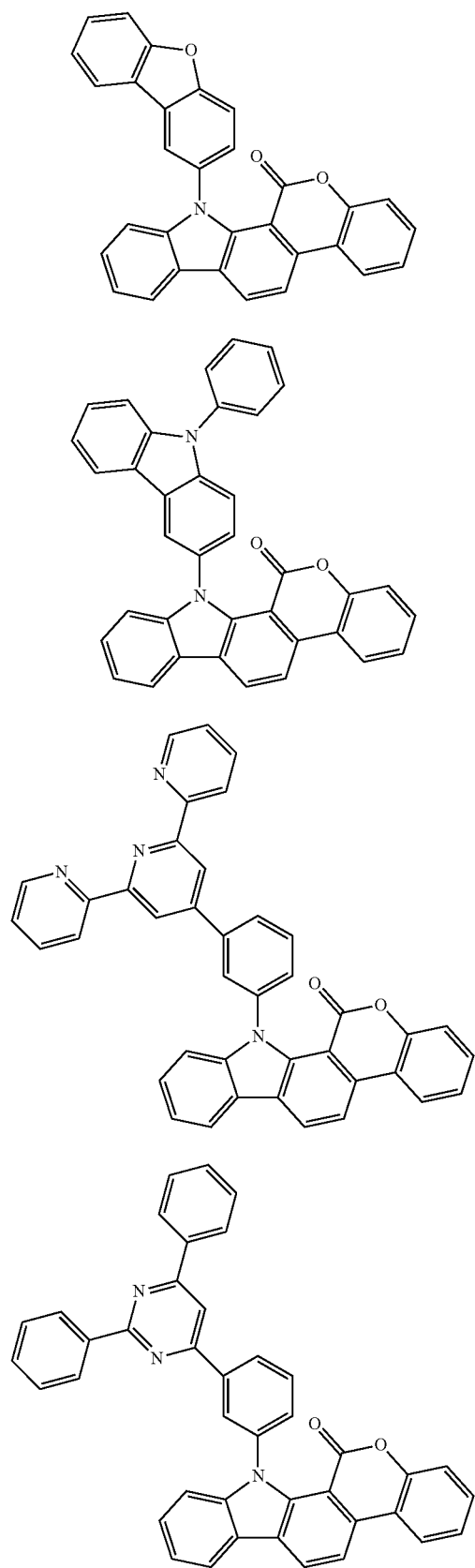
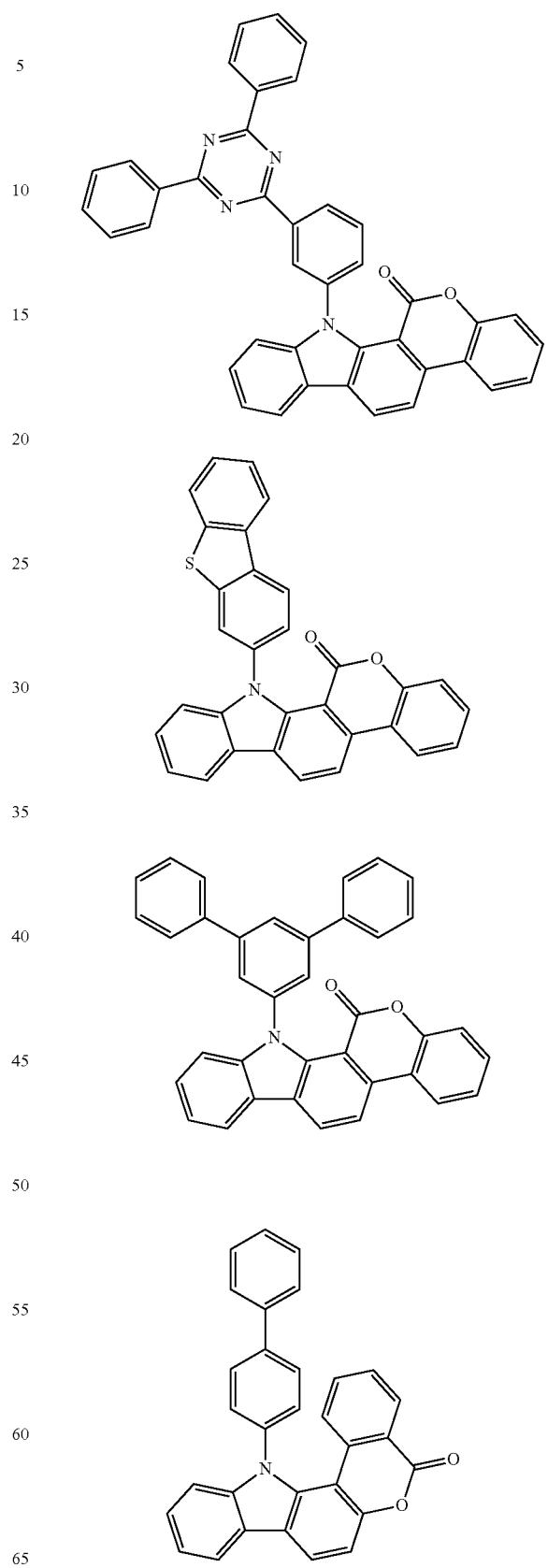

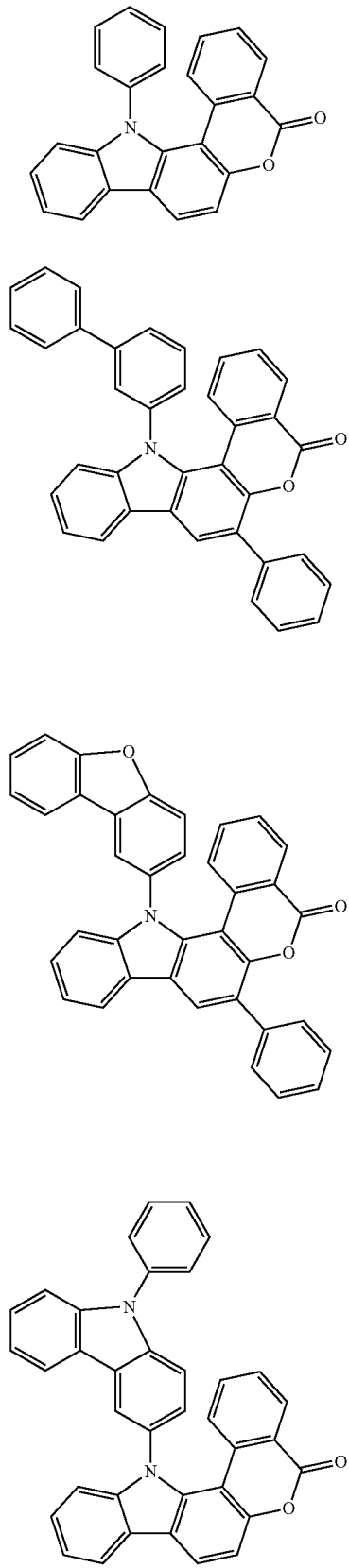
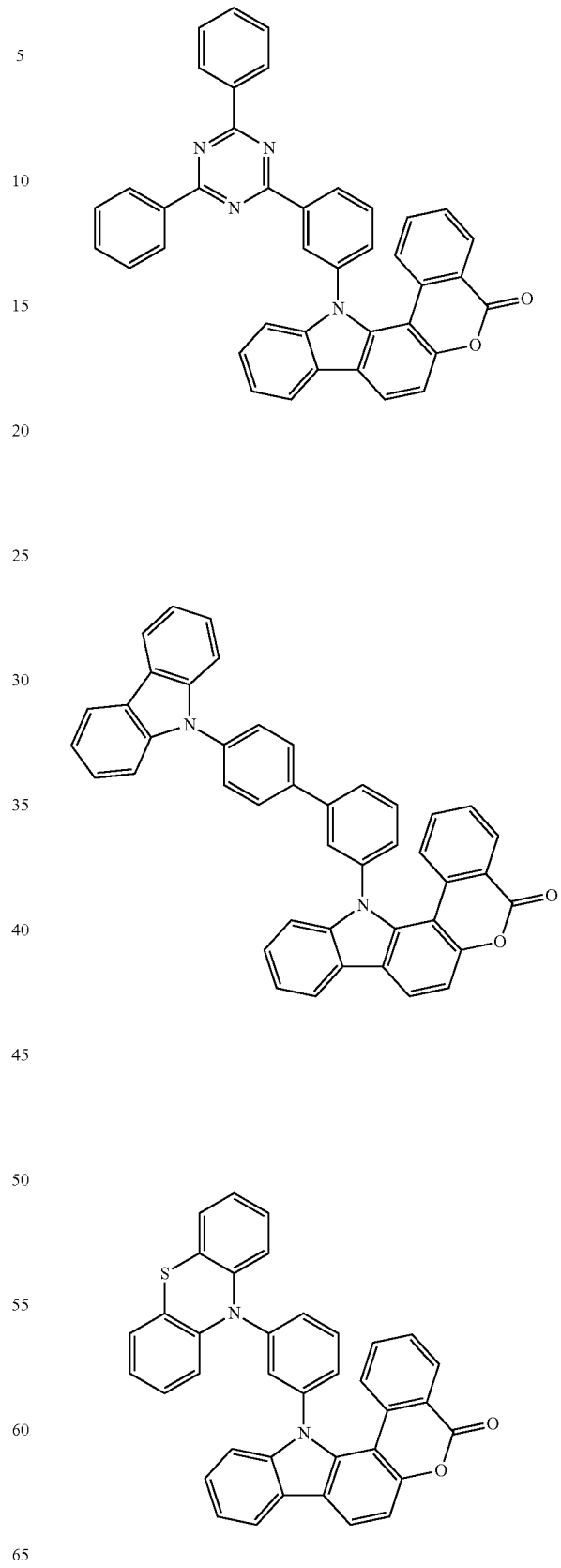

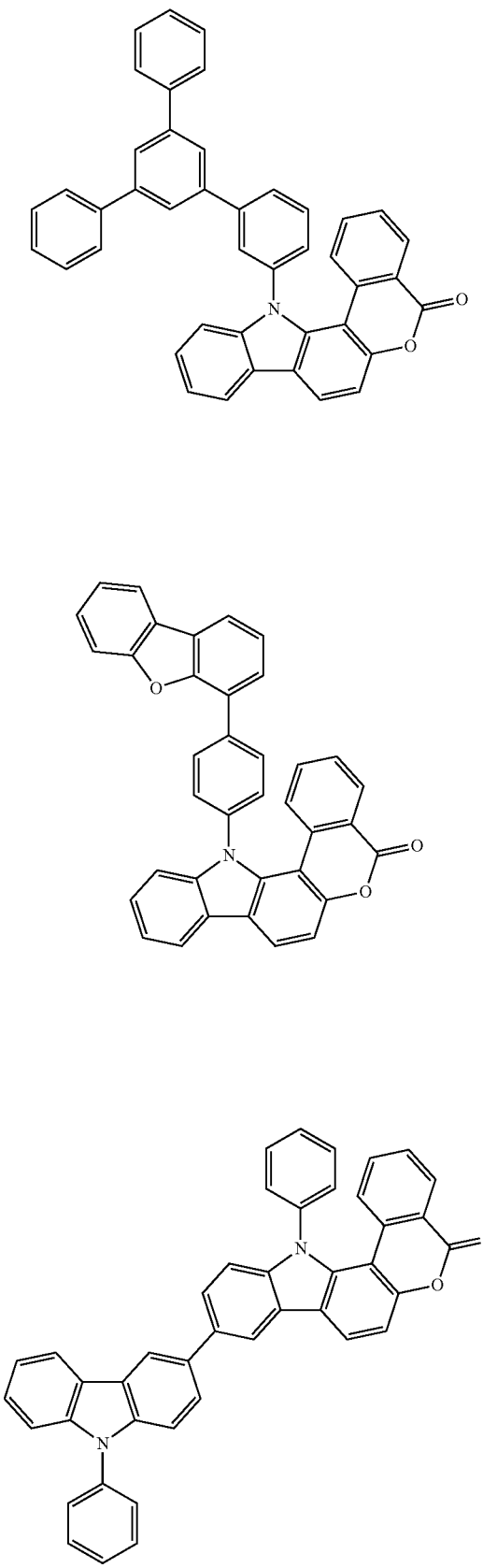
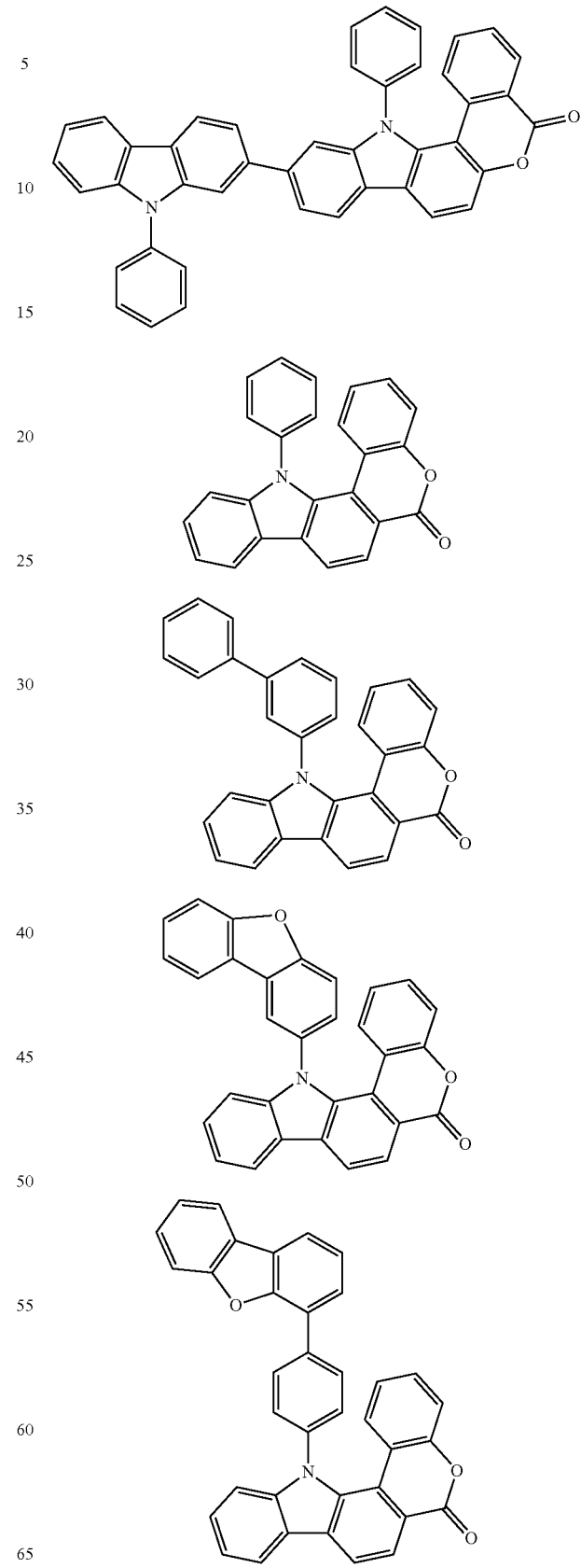

51
-continued
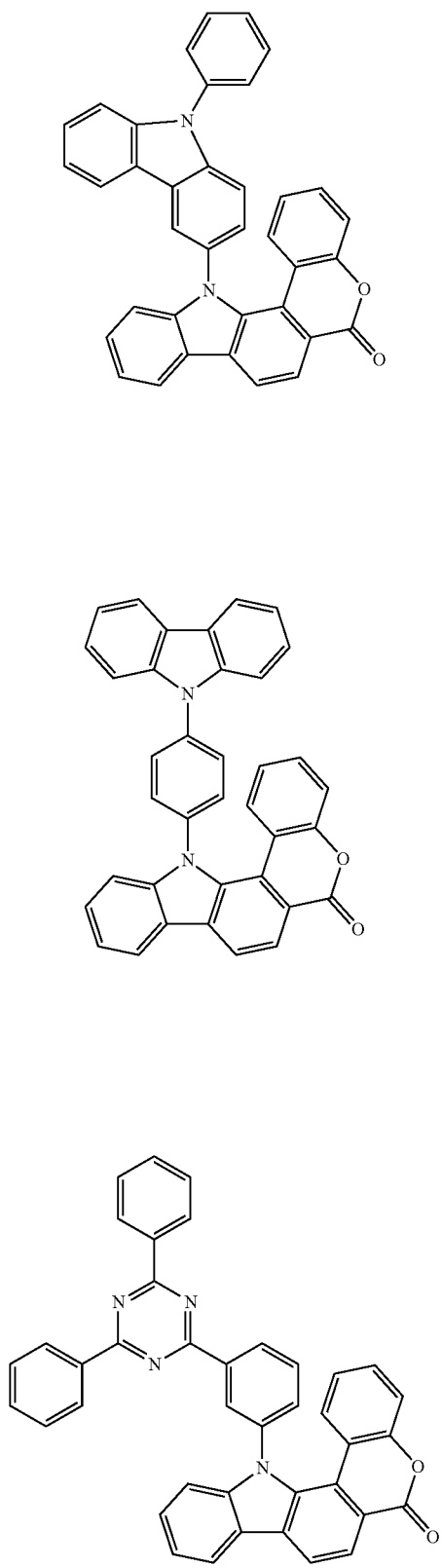
52
-continued
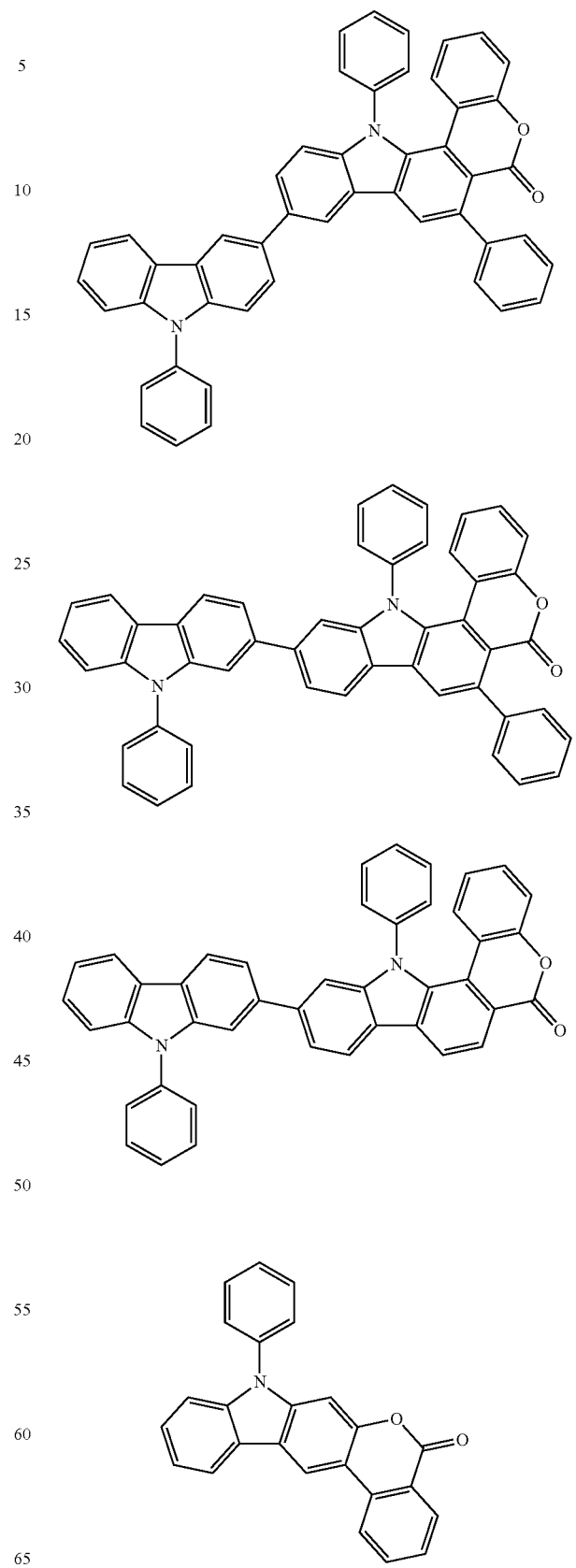

53
-continued
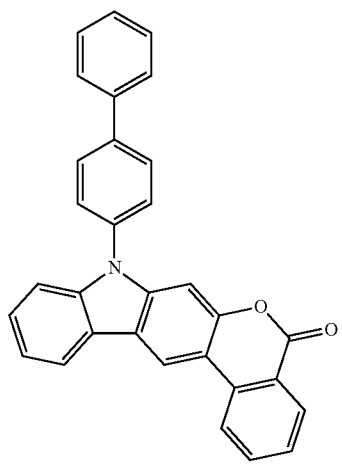 [SMILES: O=c1oc2cc3c(cc2c2ccccc12)c1ccccc1n3-c1ccc(-c2ccccc2)cc1]
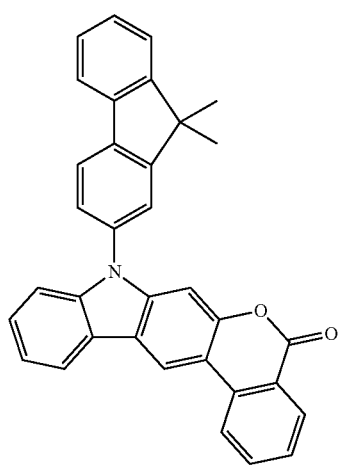 [SMILES: CC1(C)c2ccccc2-c2ccc(-n3c4ccccc4c4cc5c(cc43)oc(=O)c3ccccc35)cc21]
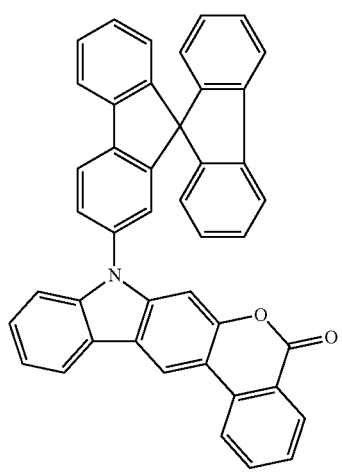 [SMILES: O=c1oc2cc3c(cc2c2ccccc12)c1ccccc1n3-c1ccc2c(c1)C1(c3ccccc3-c3ccccc31)c1ccccc1-2]
54
-continued
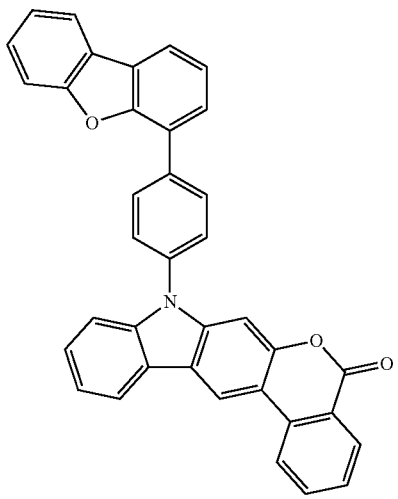 [SMILES: O=c1oc2cc3c(cc2c2ccccc12)c1ccccc1n3-c1ccc(-c2cccc3c2oc2ccccc23)cc1]
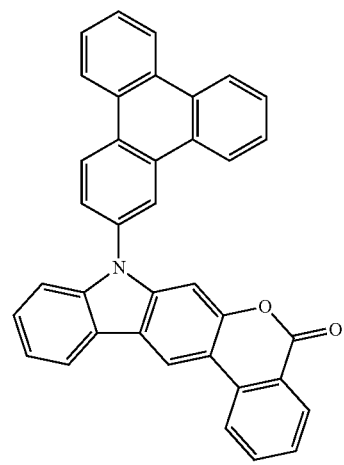 [SMILES: O=c1oc2cc3c(cc2c2ccccc12)c1ccccc1n3-c1ccc2c3ccccc3c3ccccc3c2c1]
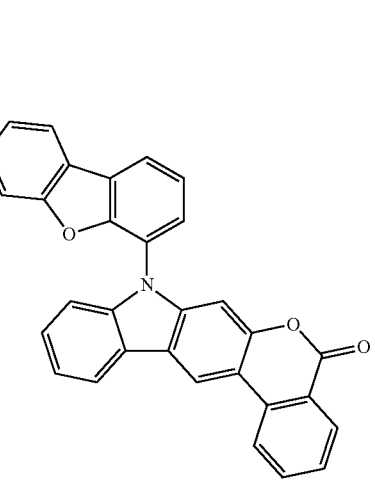

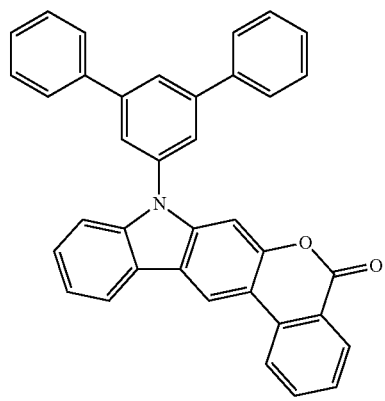 [SMILES: O=c1oc2cc3c(cc2c2ccccc12)c1ccccc1n3-c1cc(-c2ccccc2)cc(-c2ccccc2)c1]
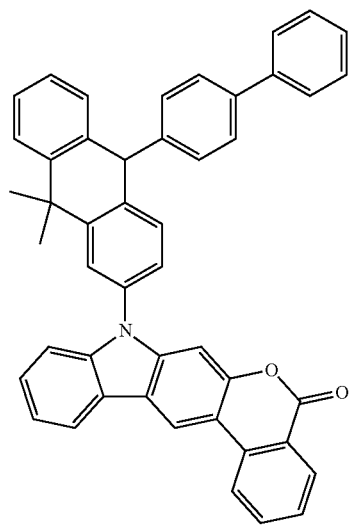
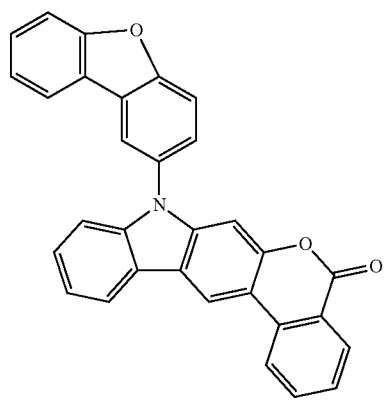 [SMILES: O=c1oc2cc3c(cc2c2ccccc12)c1ccccc1n3-c1ccc2oc3ccccc3c2c1]
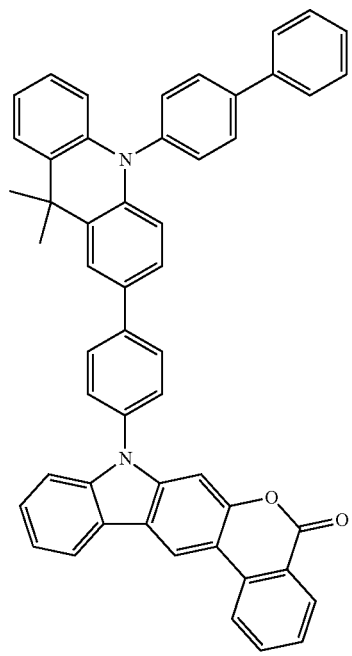
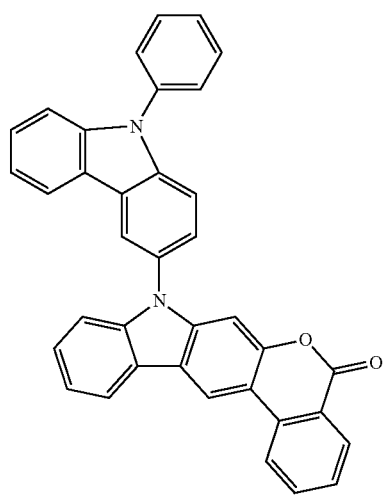 [SMILES: O=c1oc2cc3c(cc2c2ccccc12)c1ccccc1n3-c1ccc2c(c1)c1ccccc1n2-c1ccccc1]
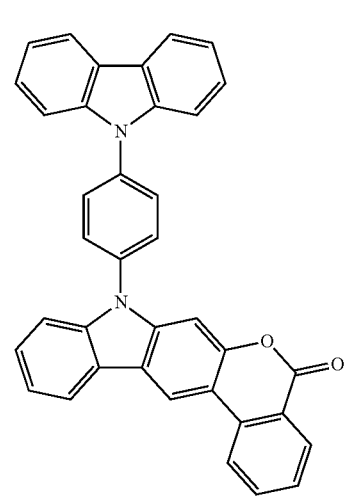 [SMILES: O=c1oc2cc3c(cc2c2ccccc12)c1ccccc1n3-c1ccc(-n2c3ccccc3c3ccccc32)cc1]

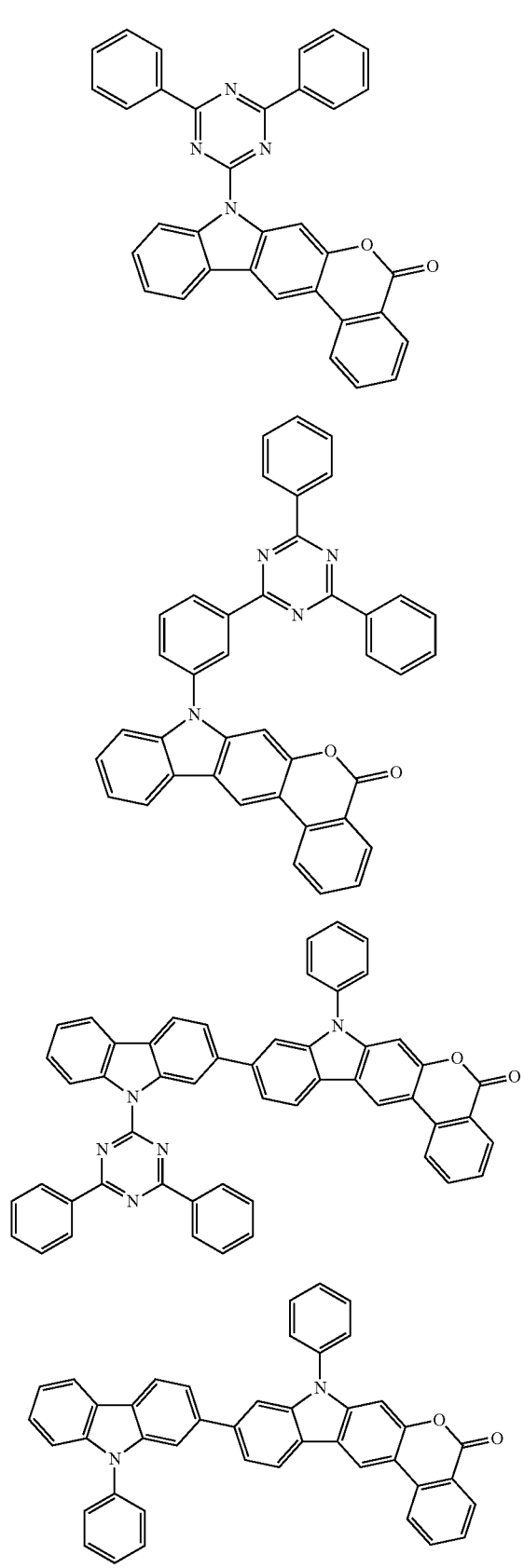
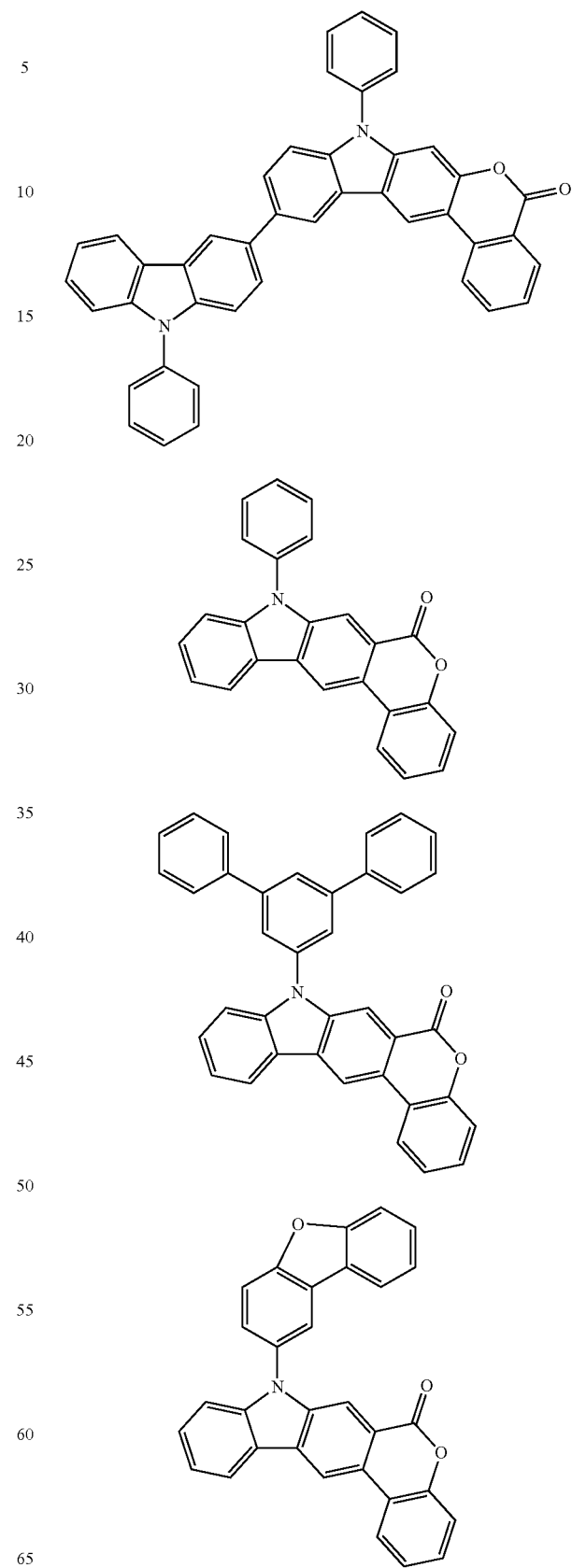

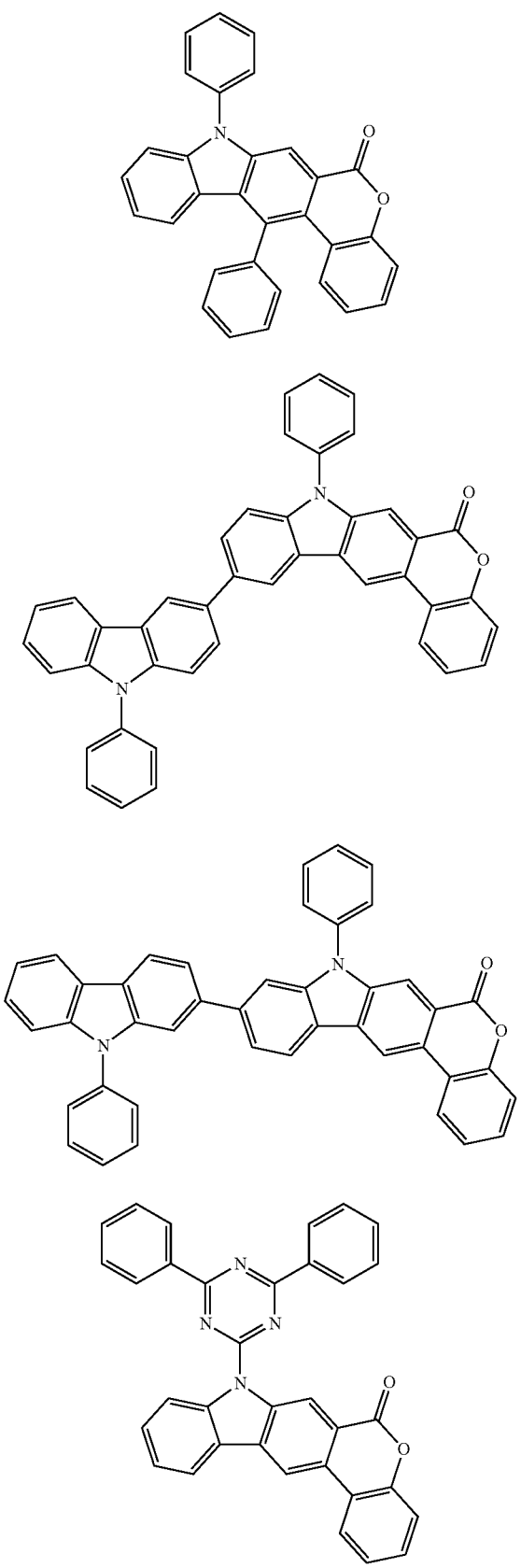

-continued
61
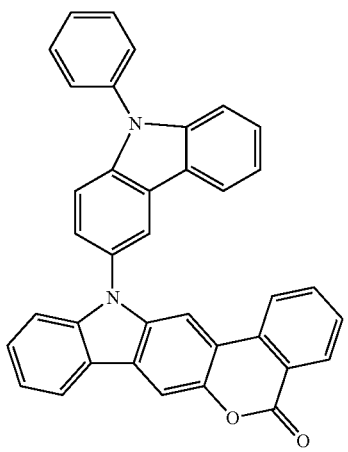 [SMILES: O=c1oc2cc3c4ccccc4n(-c4ccc5c(c4)c4ccccc4n5-c4ccccc4)c3cc2c2ccccc12]
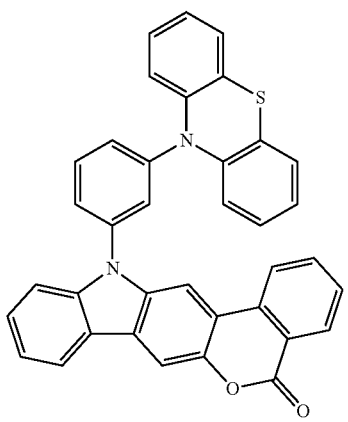 [SMILES: O=c1oc2cc3c4ccccc4n(-c4cccc(N5c6ccccc6Sc6ccccc65)c4)c3cc2c2ccccc12]
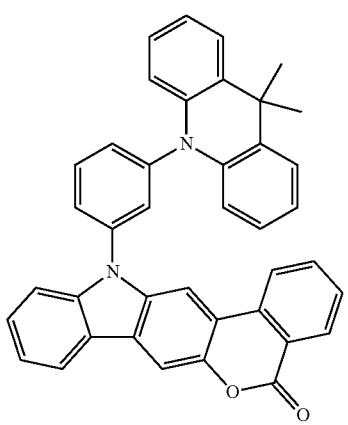 [SMILES: CC1(C)c2ccccc2N(c2cccc(-n3c4ccccc4c4cc5oc(=O)c6ccccc6c5cc43)c2)c2ccccc21]
-continued
62
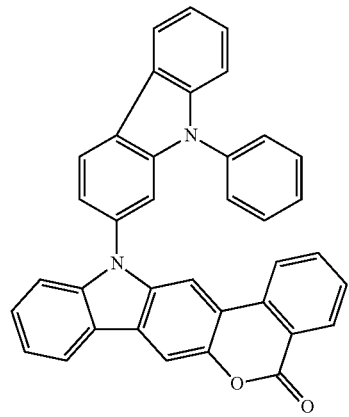 [SMILES: O=c1oc2cc3c4ccccc4n(-c4ccc5c6ccccc6n(-c6ccccc6)c5c4)c3cc2c2ccccc12]
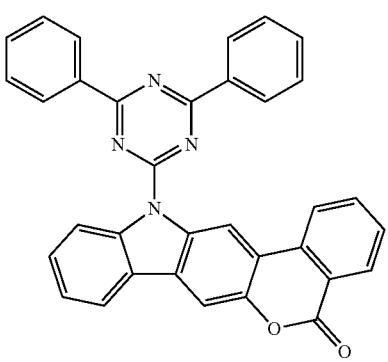 [SMILES: O=c1oc2cc3c4ccccc4n(-c4nc(-c5ccccc5)nc(-c5ccccc5)n4)c3cc2c2ccccc12]
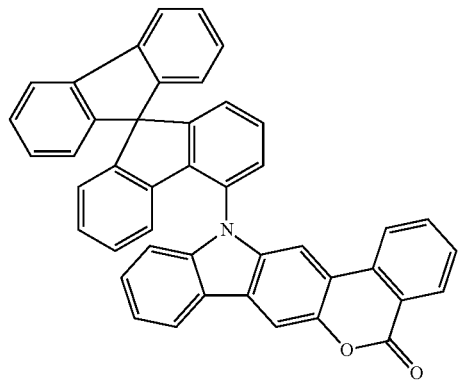 [SMILES: O=c1oc2cc3c4ccccc4n(-c4cccc5c4-c4ccccc4C54c5ccccc5-c5ccccc54)c3cc2c2ccccc12]
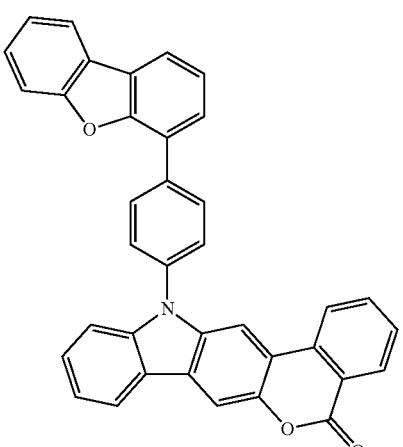

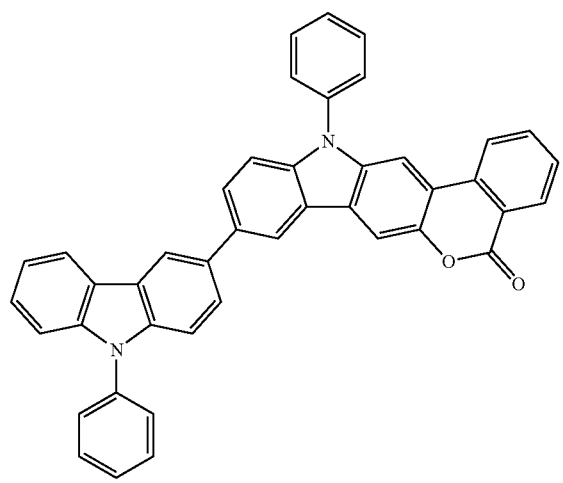 [SMILES: O=c1oc2cc3c4cc(-c5ccc6c(c5)c5ccccc5n6-c5ccccc5)ccc4n(-c4ccccc4)c3cc2c2ccccc12]
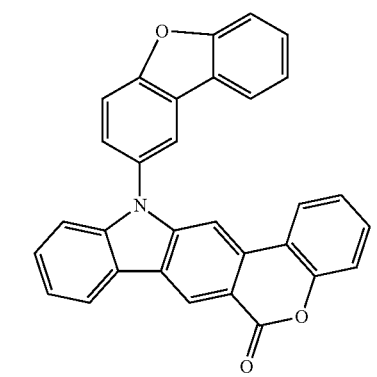
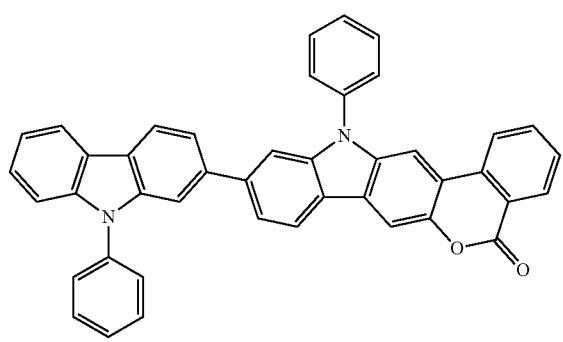 [SMILES: O=c1oc2cc3c4ccc(-c5ccc6c7ccccc7n(-c7ccccc7)c6c5)cc4n(-c4ccccc4)c3cc2c2ccccc12]
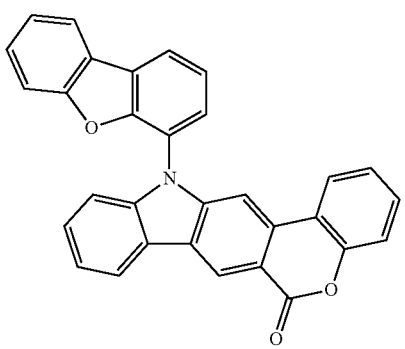
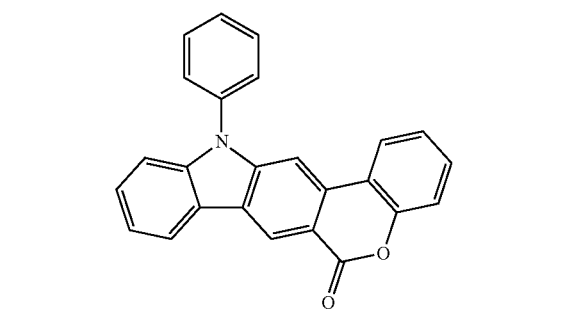 [SMILES: O=c1oc2ccccc2c2cc3c(cc12)c1ccccc1n3-c1ccccc1]
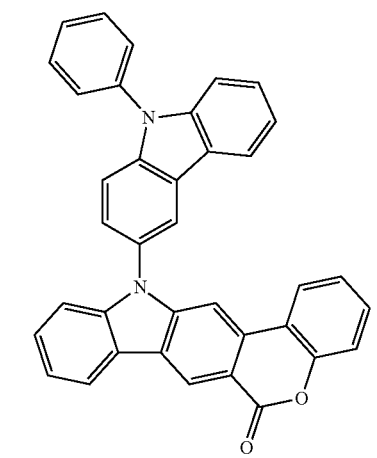
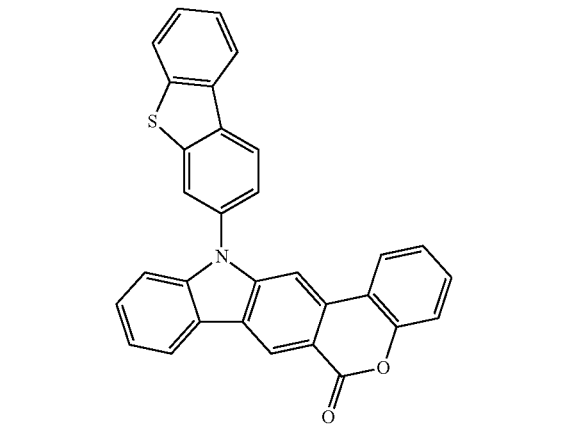 [SMILES: O=c1oc2ccccc2c2cc3c(cc12)c1ccccc1n3-c1ccc2c(c1)sc1ccccc12]
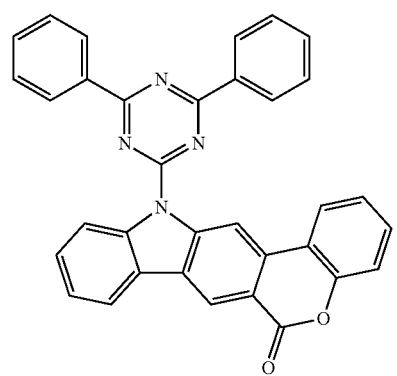 [SMILES: O=c1oc2ccccc2c2cc3c(cc12)c1ccccc1n3-c1nc(-c2ccccc2)nc(-c2ccccc2)n1]

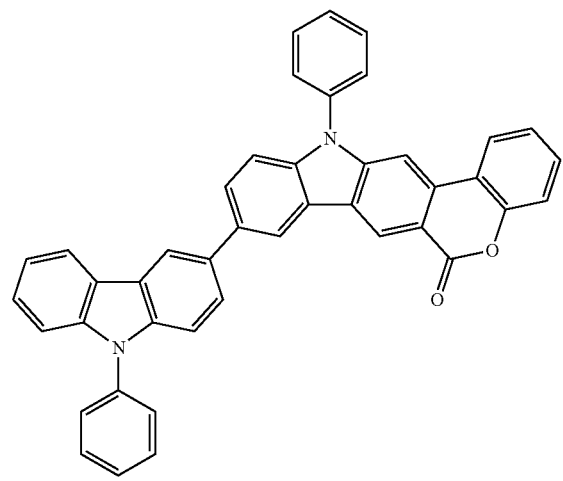 [SMILES: O=c1oc2ccccc2c2cc3c(cc12)c1cc(-c2ccc4c(c2)c2ccccc2n4-c2ccccc2)ccc1n3-c1ccccc1]
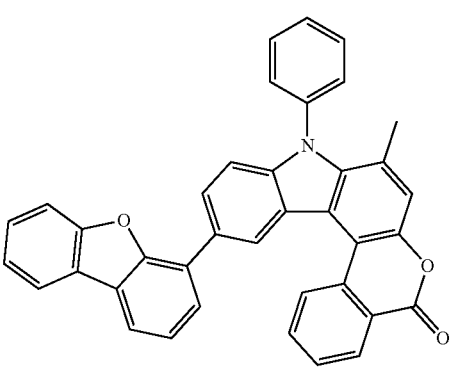
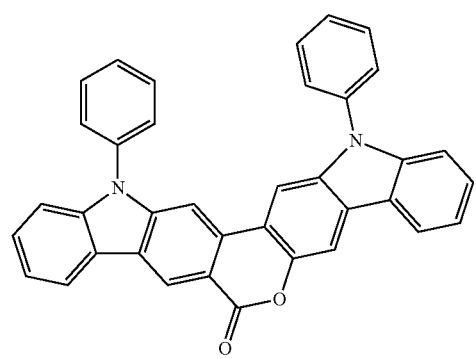 [SMILES: O=c1oc2cc3c4ccccc4n(-c4ccccc4)c3cc2c2cc3c(cc12)c1ccccc1n3-c1ccccc1]
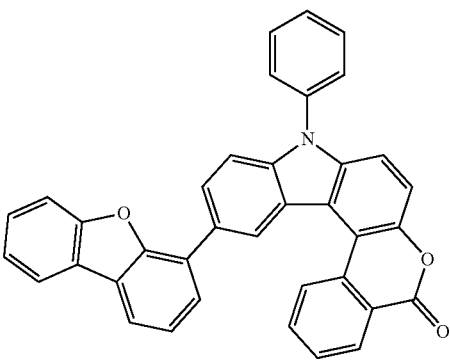
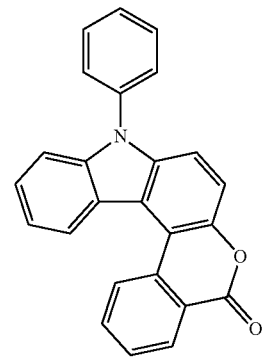 [SMILES: O=c1oc2ccc3c(c4ccccc4n3-c3ccccc3)c2c2ccccc12]
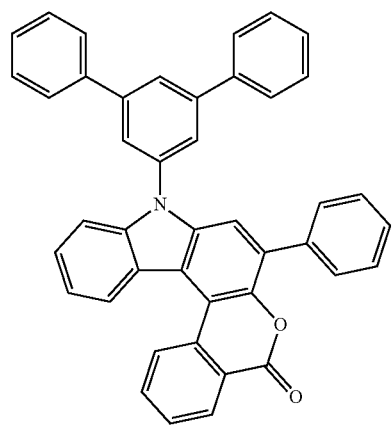 [SMILES: O=c1oc2c(-c3ccccc3)cc3c(c4ccccc4n3-c3cc(-c4ccccc4)cc(-c4ccccc4)c3)c2c2ccccc12]
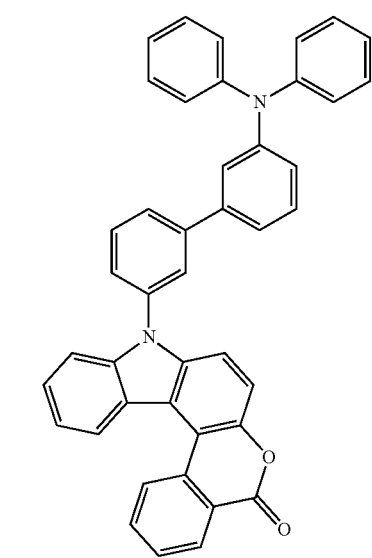 [SMILES: O=c1oc2ccc3c(c4ccccc4n3-c3cccc(-c4cccc(N(c5ccccc5)c5ccccc5)c4)c3)c2c2ccccc12]

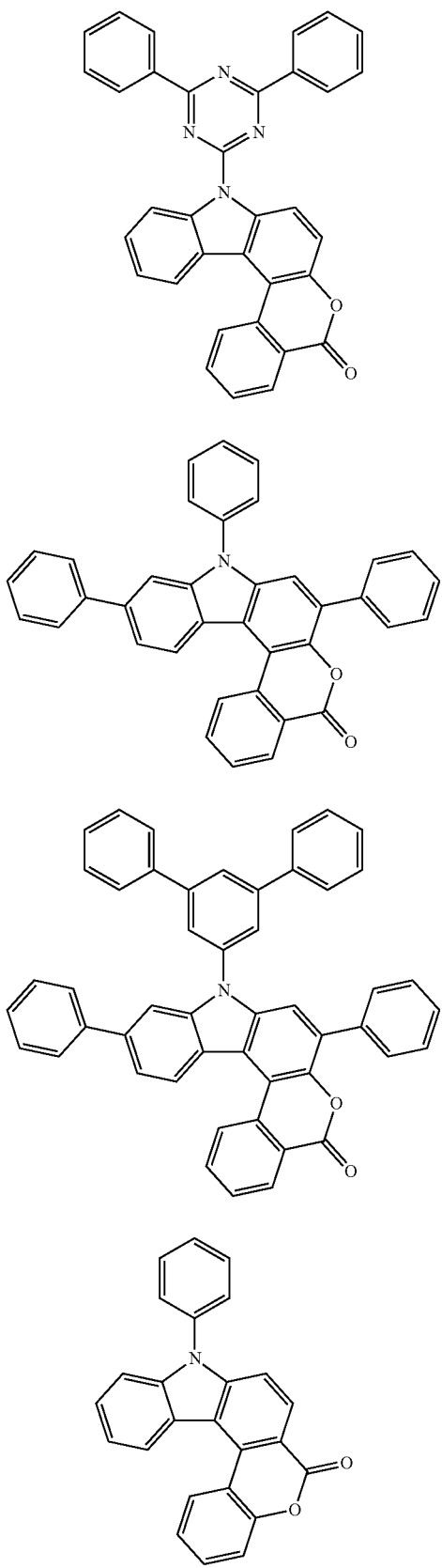
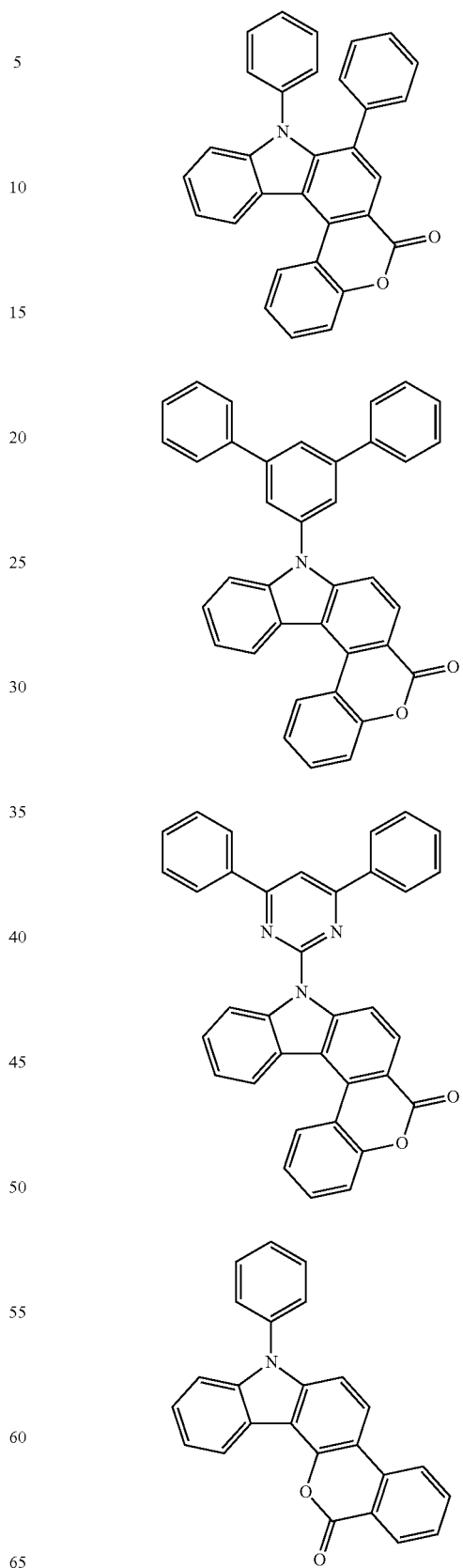

-continued
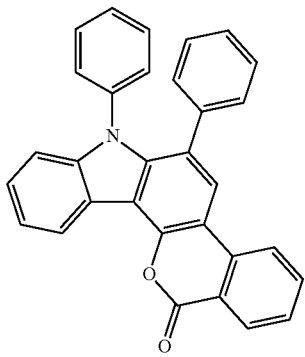 [SMILES: O=c1oc2c(cc(-c3ccccc3)c3c2c2ccccc2n3-c2ccccc2)c2ccccc12]
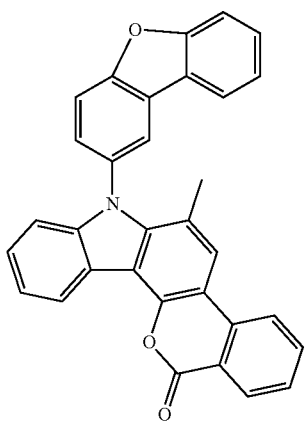 [SMILES: Cc1cc2c3ccccc3c(=O)oc2c2c3ccccc3n(-c3ccc4oc5ccccc5c4c3)c12]
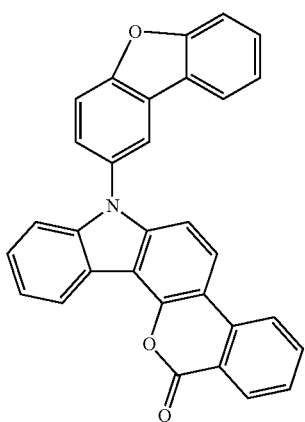 [SMILES: O=c1oc2c(ccc3c2c2ccccc2n3-c2ccc3oc4ccccc4c3c2)c2ccccc12]
-continued
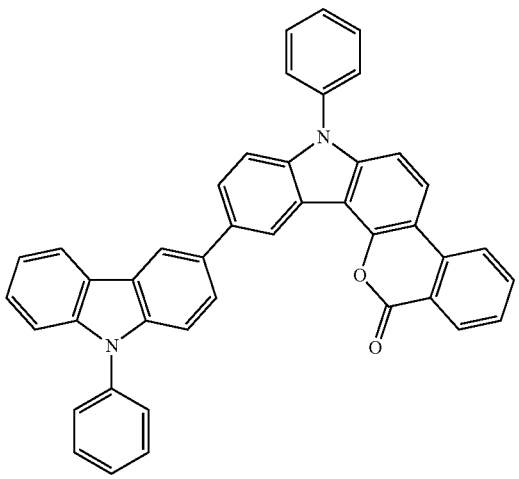 [SMILES: O=c1oc2c(ccc3c2c2cc(-c4ccc5c(c4)c4ccccc4n5-c4ccccc4)ccc2n3-c2ccccc2)c2ccccc12]
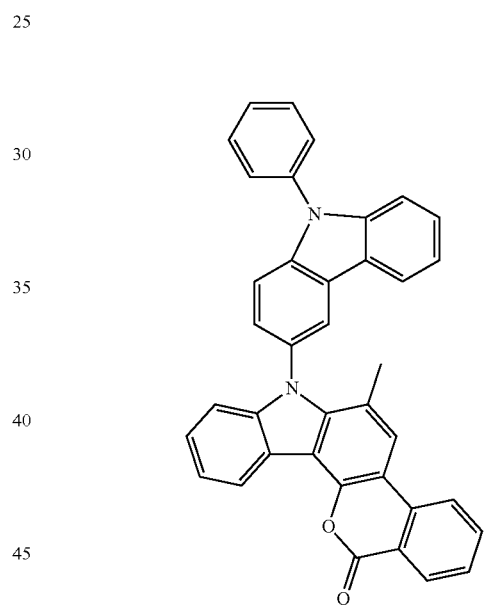
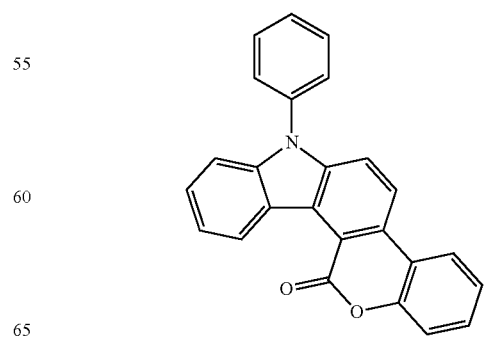

71
-continued
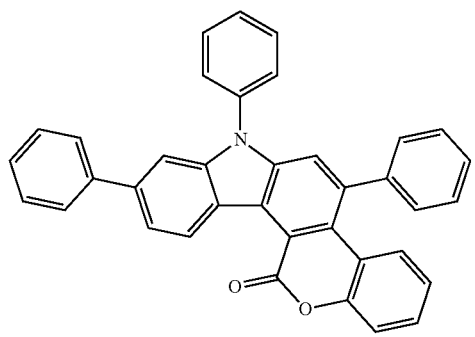 [SMILES: O=c1oc2ccccc2c2c(-c3ccccc3)cc3c(c4ccc(-c5ccccc5)cc4n3-c3ccccc3)c12]
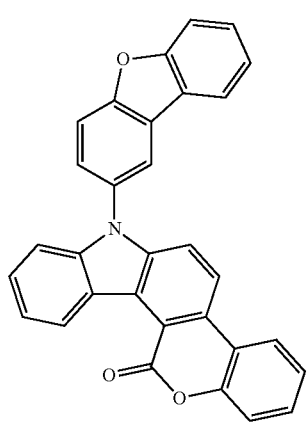 [SMILES: O=c1oc2ccccc2c2ccc3c(c4ccccc4n3-c3ccc4oc5ccccc5c4c3)c12]
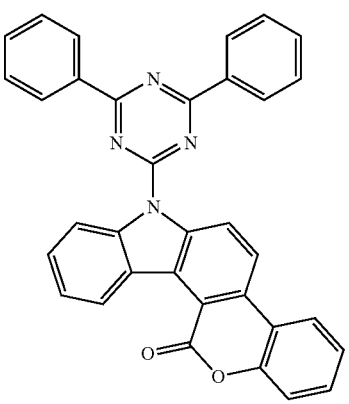 [SMILES: O=c1oc2ccccc2c2ccc3c(c4ccccc4n3-c3nc(-c4ccccc4)nc(-c4ccccc4)n3)c12]
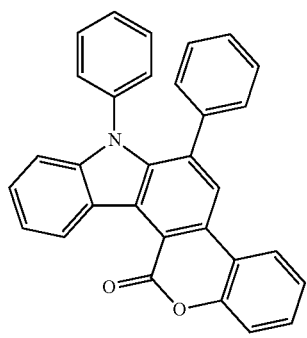 [SMILES: O=c1oc2ccccc2c2cc(-c3ccccc3)c3c(c4ccccc4n3-c3ccccc3)c12]
72
-continued
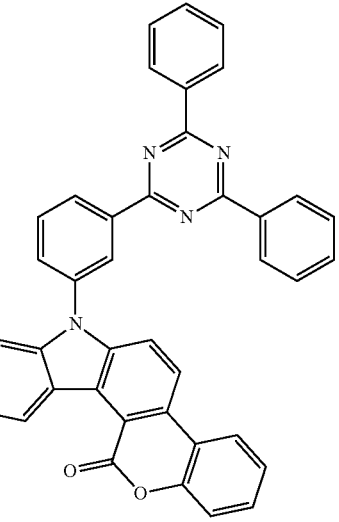
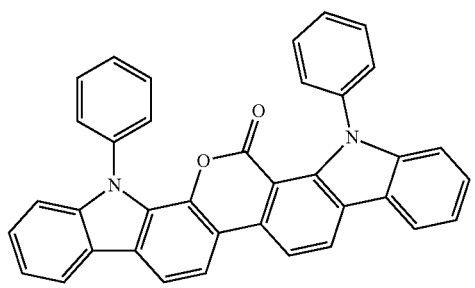 [SMILES: O=c1oc2c(ccc3c4ccccc4n(-c4ccccc4)c32)c2ccc3c4ccccc4n(-c4ccccc4)c3c12]
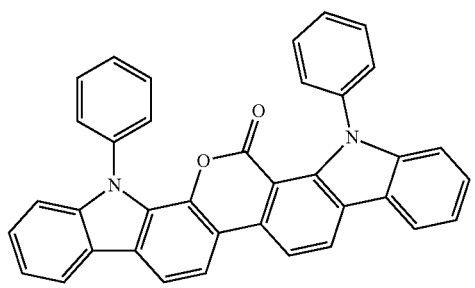 [SMILES: O=c1oc2c(ccc3c4ccccc4n(-c4ccccc4)c32)c2ccc3c4ccccc4n(-c4ccccc4)c3c12]
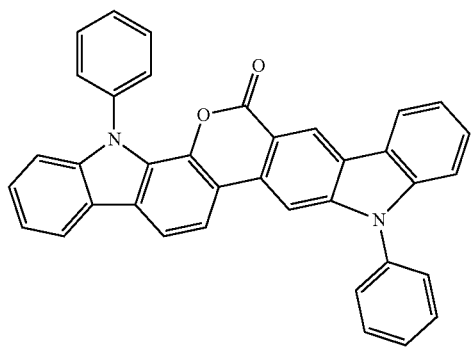 [SMILES: O=c1oc2c(ccc3c4ccccc4n(-c4ccccc4)c32)c2cc3c(cc12)c1ccccc1n3-c1ccccc1]
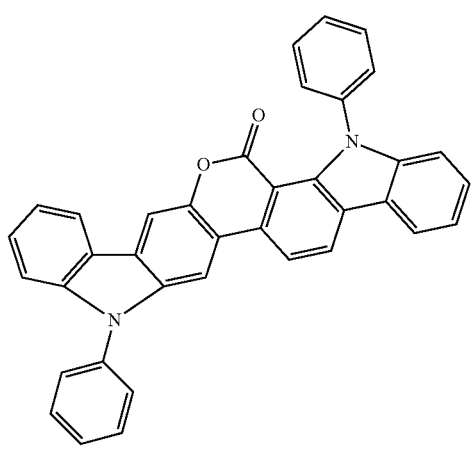 [SMILES: O=c1oc2cc3c4ccccc4n(-c4ccccc4)c3cc2c2ccc3c4ccccc4n(-c4ccccc4)c3c12]

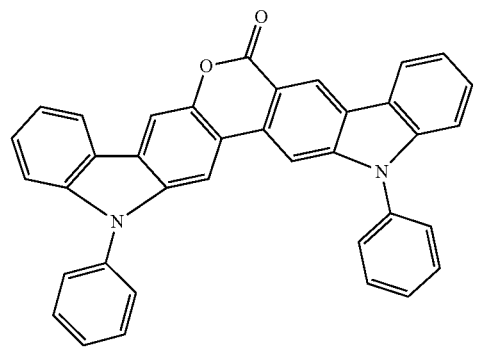 [SMILES: O=c1oc2cc3c4ccccc4n(-c4ccccc4)c3cc2c2cc3c(cc12)c1ccccc1n3-c1ccccc1]
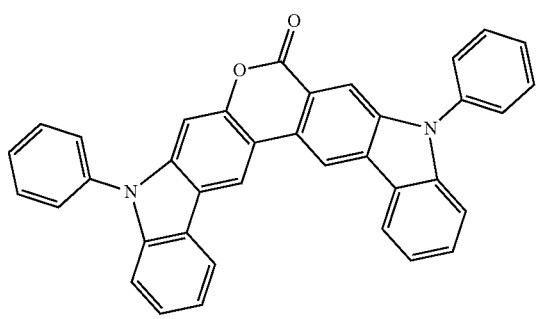 [SMILES: O=c1oc2cc3c(cc2c2cc4c5ccccc5n(-c5ccccc5)c4cc12)c1ccccc1n3-c1ccccc1]
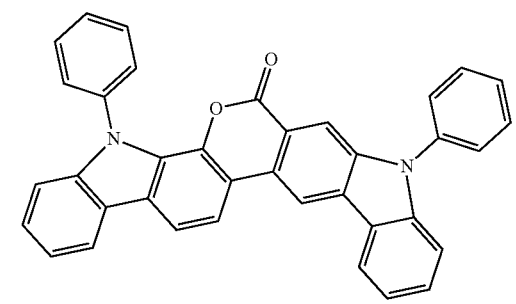 [SMILES: O=c1oc2c(ccc3c4ccccc4n(-c4ccccc4)c32)c2cc3c4ccccc4n(-c4ccccc4)c3cc12]
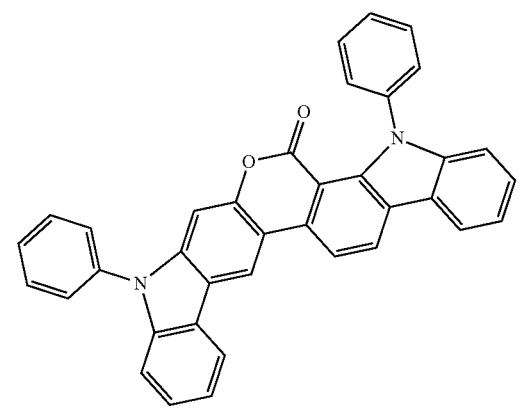 [SMILES: O=c1oc2cc3c(cc2c2ccc4c5ccccc5n(-c5ccccc5)c4c12)c1ccccc1n3-c1ccccc1]
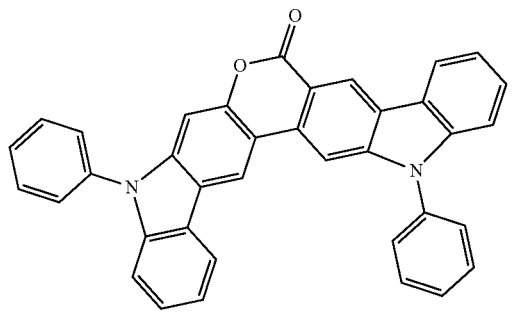 [SMILES: O=c1oc2cc3c(cc2c2cc4c(cc12)c1ccccc1n4-c1ccccc1)c1ccccc1n3-c1ccccc1]
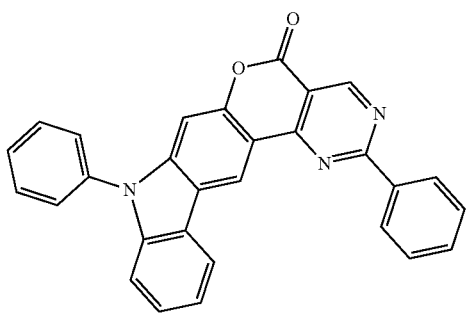 [SMILES: O=c1oc2cc3c(cc2c2nc(-c4ccccc4)ncc12)c1ccccc1n3-c1ccccc1]
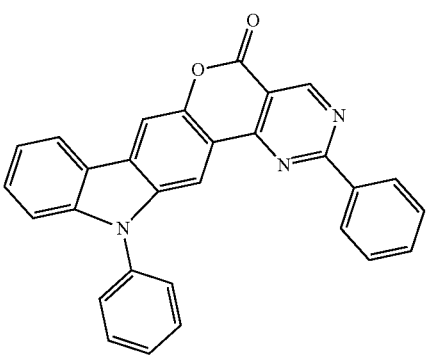 [SMILES: O=c1oc2cc3c4ccccc4n(-c4ccccc4)c3cc2c2nc(-c3ccccc3)ncc12]
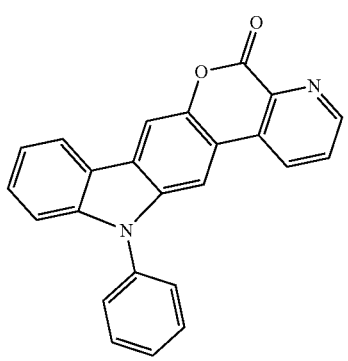 [SMILES: O=c1oc2cc3c4ccccc4n(-c4ccccc4)c3cc2c2cccnc12]
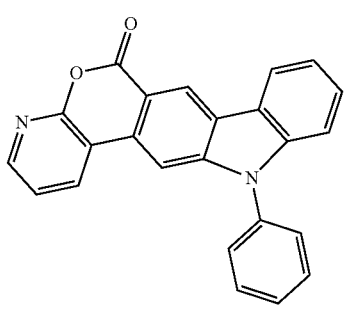 [SMILES: O=c1oc2ncccc2c2cc3c(cc12)c1ccccc1n3-c1ccccc1]

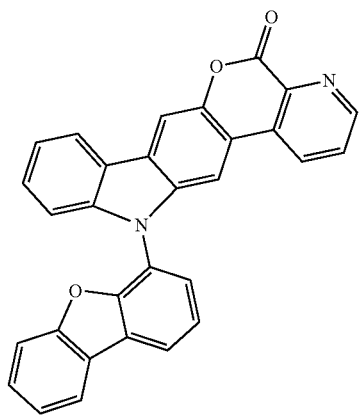 [SMILES: O=c1oc2cc3c4ccccc4n(-c4cccc5c4oc4ccccc45)c3cc2c2cccnc12]
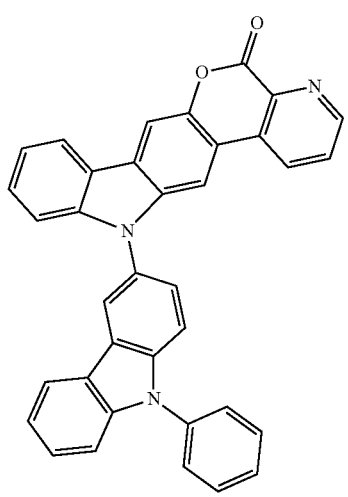 [SMILES: O=c1oc2cc3c4ccccc4n(-c4ccc5c(c4)c4ccccc4n5-c4ccccc4)c3cc2c2cccnc12]
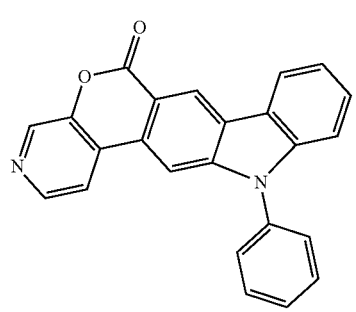 [SMILES: O=c1oc2cnccc2c2cc3c(cc12)c1ccccc1n3-c1ccccc1]
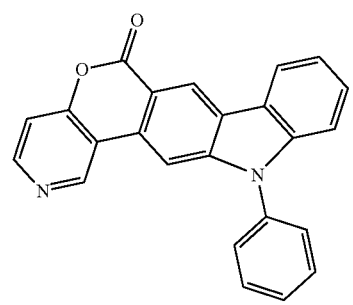 [SMILES: O=c1oc2ccncc2c2cc3c(cc12)c1ccccc1n3-c1ccccc1]
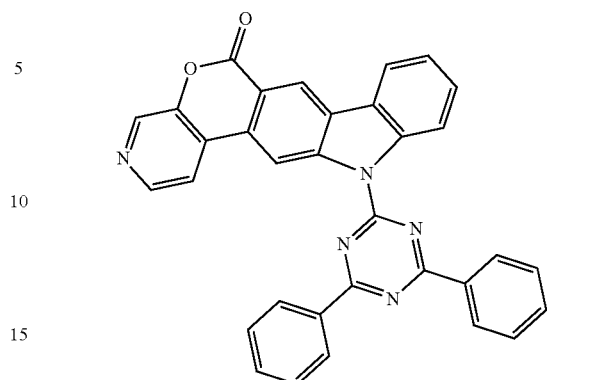
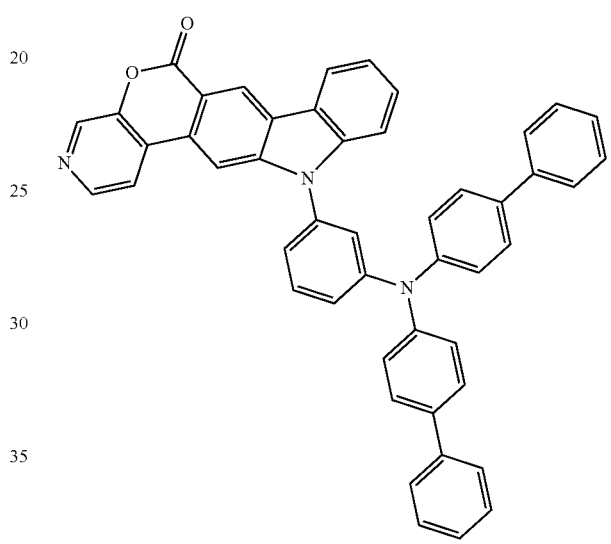
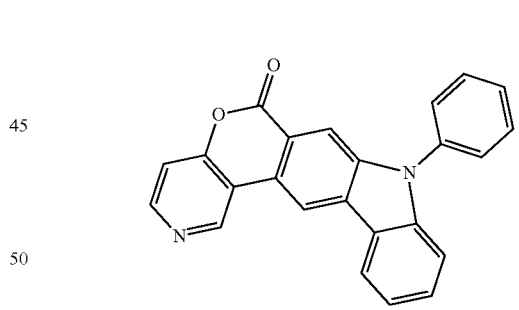
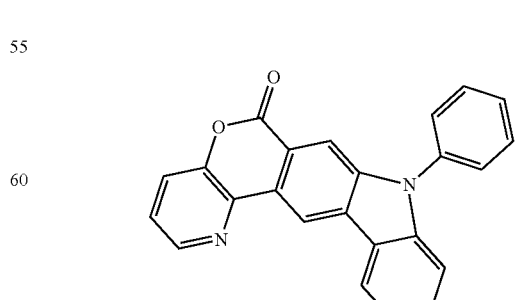

77
-continued

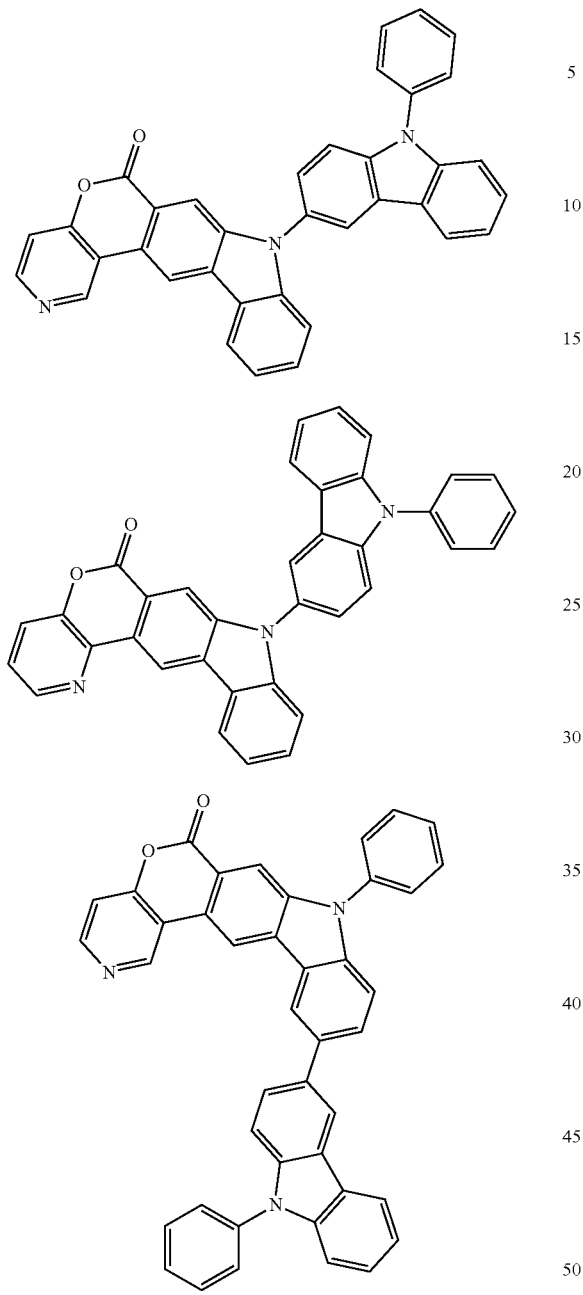

The synthesis of the base structure of the compounds of the invention and the functionalization thereof can be effected by the routes outlined hereinafter. Scheme 1 shows, as an overview, the two possible base structures, oxa-aza-indeno[1,2-b]phenanthrenone (scheme 1a) and oxa-aza-indeno[2,1-b]phenanthrenone (scheme 1 b), which differ in terms of which of the two aromatic groups of the phenan-throne (the term phenanthrone is used synonymously with dibenzopyranone) the group of the formula (3) is fused to.

Scheme 1 a) Oxa-aza-indeno[1,2-b]phenanthrenone

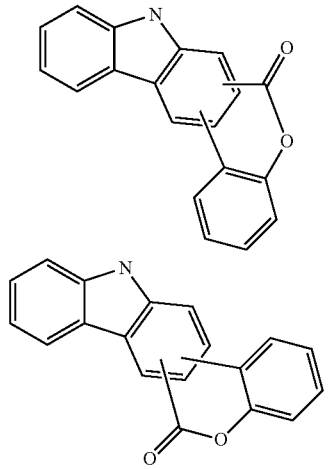

b) Oxa-aza-indeno[2,1-b]phenanthrenone

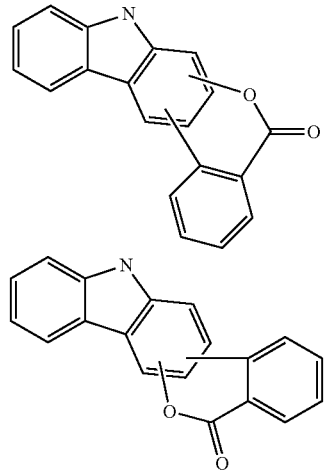

The oxa-aza-indeno[1,2-b]phenanthrenones of scheme 1a) can be prepared by oxidation of fluorenone derivatives with sodium percarbonate, subsequent Buchwald coupling and further conversion by cyclization with palladium acetate and subsequent functionalization by Ullmann coupling or a further Buchwald coupling with neutral, electron-deficient or electron-rich aromatics (scheme 2). Dibenzo[b,d]pyran-6-ones can also be prepared via Suzuki coupling (Journal of Combinatorial Chemistry, 12(5), 664-669; 2010).

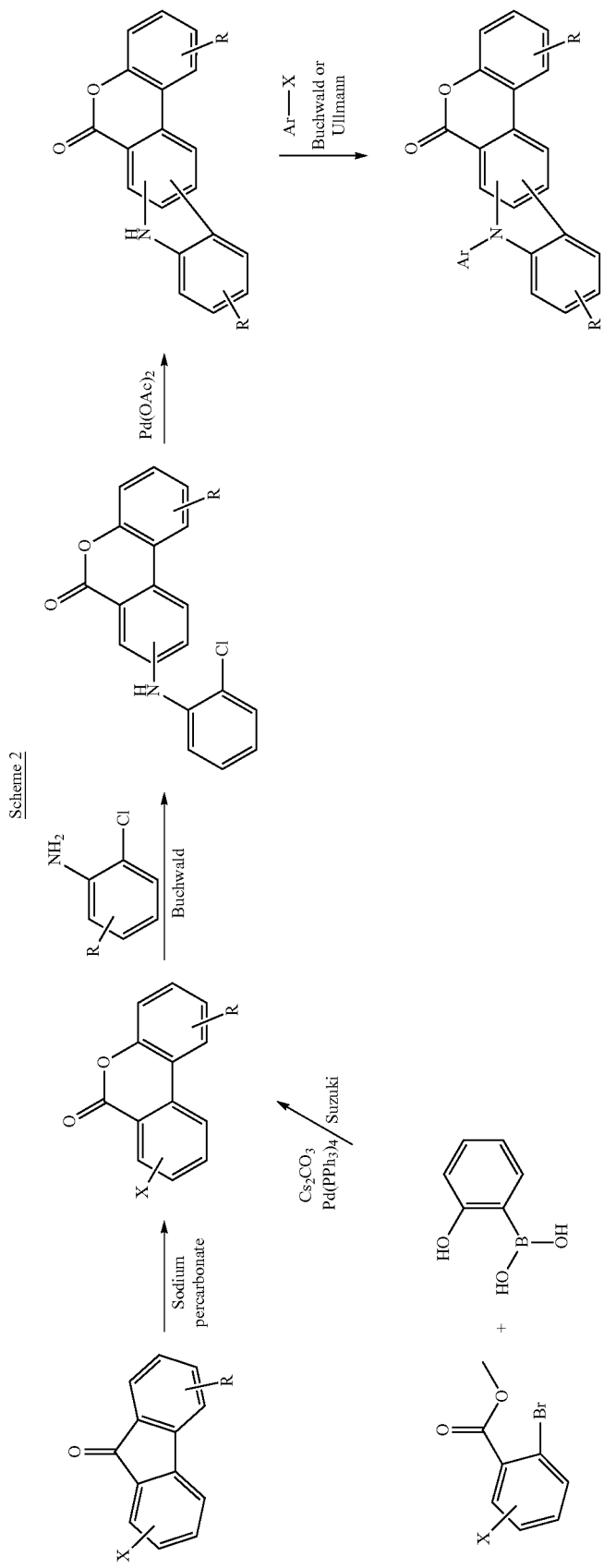

Scheme 3 shows, proceeding from the corresponding bromofluorenone derivative (scheme 3a) or from the dibromofluorenone derivative (scheme 3b), the synthesis of two specific isomers.

Scheme 3 a)

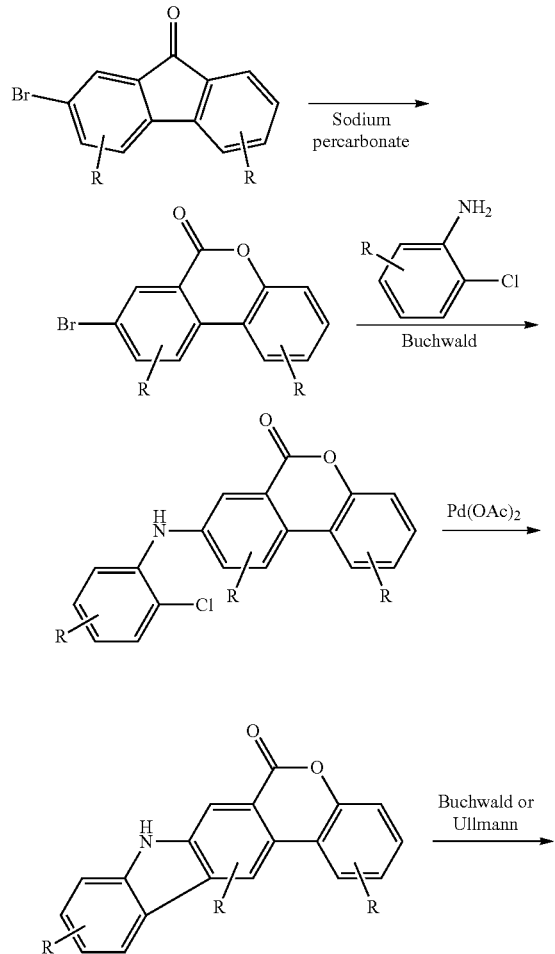

b)

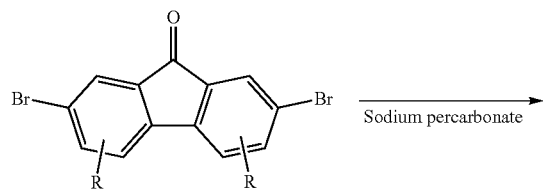

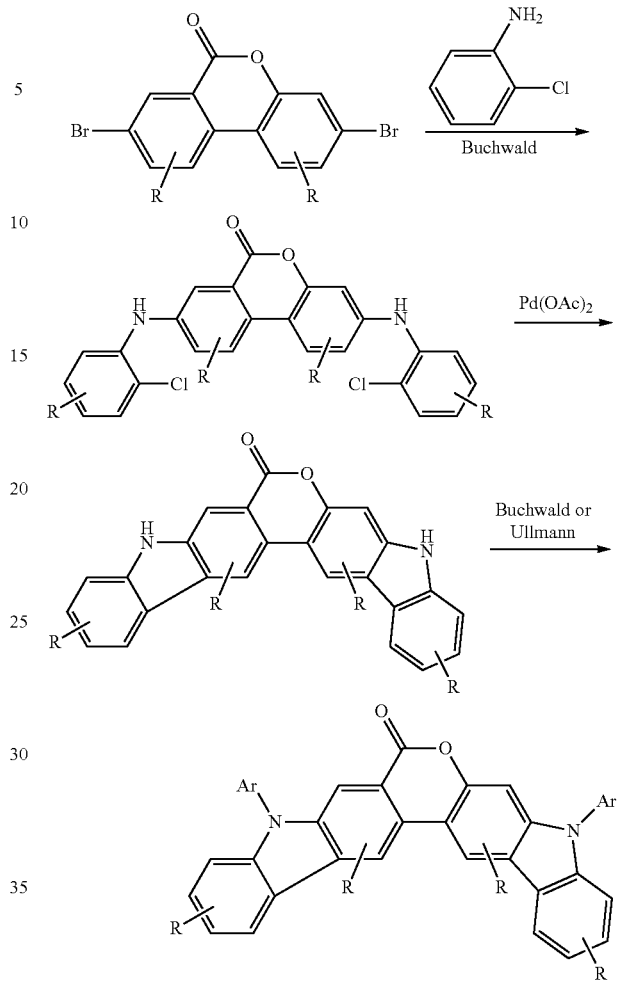

The oxa-aza-indeno[2,1-b]phenanthrenones of scheme 1 b) can be prepared by reaction of a hydroxycarbazole with an acid chloride and subsequent cyclization with palladium acetate (scheme 4) and then functionalized via Ullmann or Buchwald coupling with neutral, electron-deficient or electron-rich aromatics.

Scheme 4

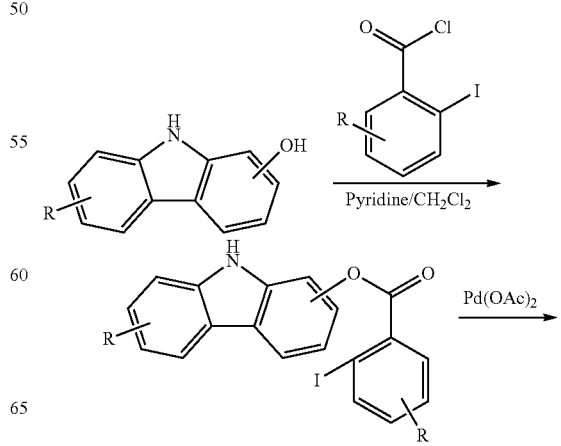

83
-continued
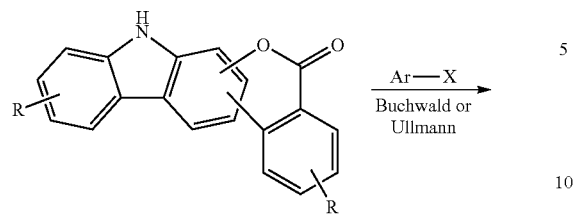
84
-continued
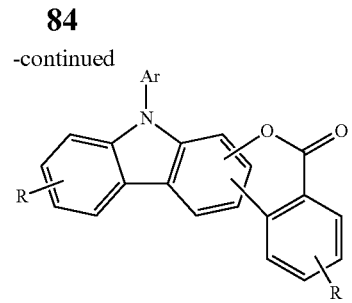
Scheme 5 shows, proceeding from 1-hydroxycarbazole (scheme 5a) or 2-hydroxycarbazole (scheme 5b), the synthesis of specific isomers.
Scheme 5
a)
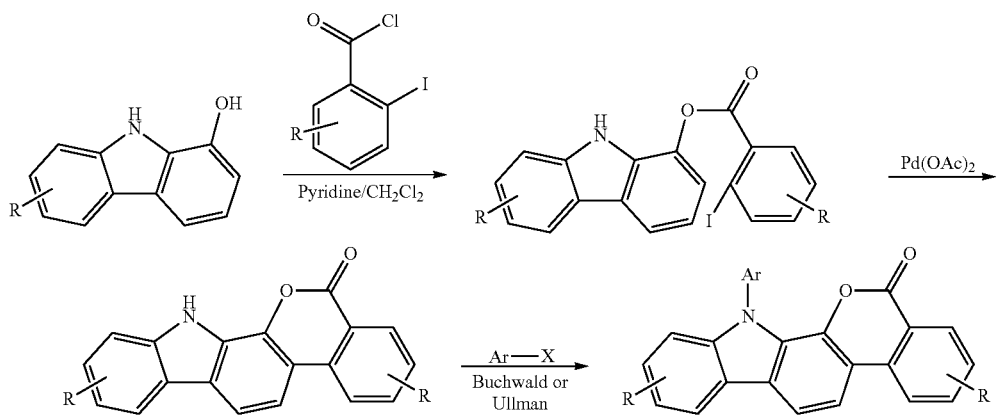
b)
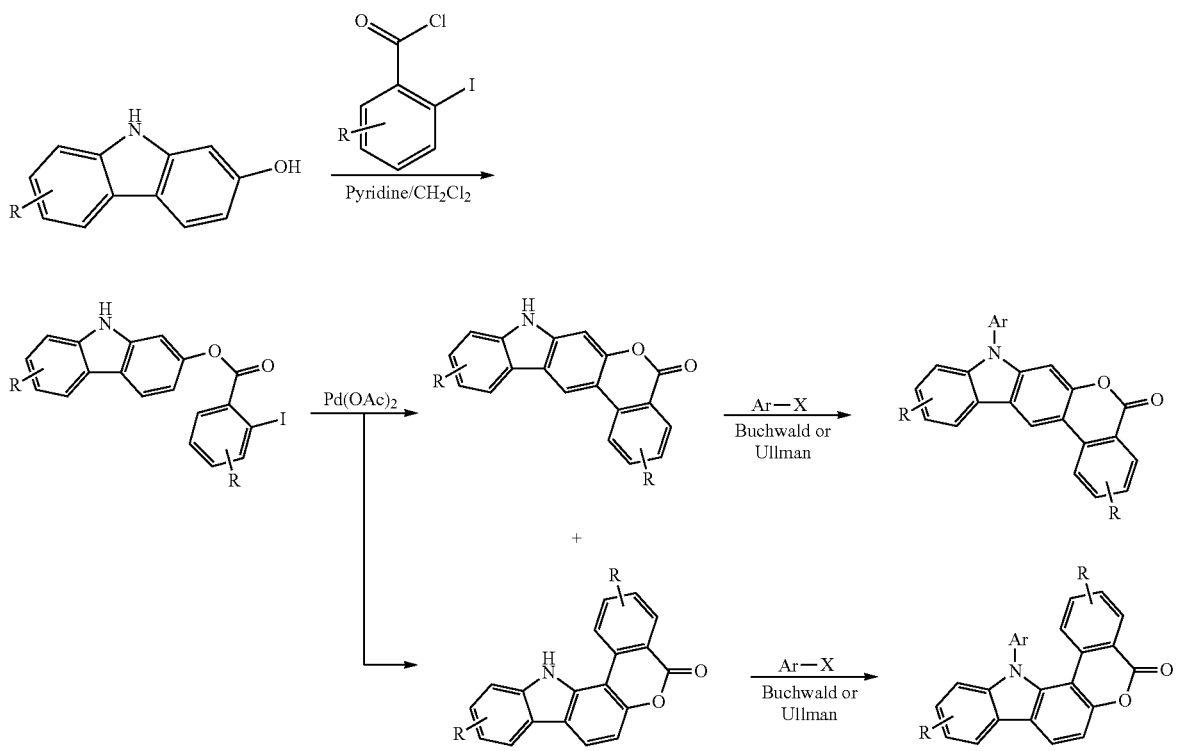

The processes shown for synthesis of the compounds of the invention should be understood by way of example. The person skilled in the art will be able to develop alternative synthesis routes within the scope of his common knowledge in the art.

The present invention further provides a process for preparing a compound of formula (1) or formula (2), comprising the reaction steps of:
a) synthesizing the base skeleton of the corresponding indolophenanthrone derivative unsubstituted on the indole nitrogen atom; and
b) introducing the substituent on the indole nitrogen atom, preferably by means of Buchwald coupling or Ullmann coupling.

The above-described compounds of the invention, especially compounds substituted by reactive leaving groups, such as bromine, iodine, chlorine, boronic acid or boronic ester, or by reactive polymerizable groups such as olefins, styrenes, acrylates, oxetanes or oxiranes, may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed compounds of the invention, wherein one or more bonds of the compound of the invention to the polymer, oligomer or dendrimer are present in place of substituents at one or more positions. According to the linkage of the compound of the invention, it forms a side chain of the oligomer or polymer or is incorporated in the main chain or forms the core of a dendrimer. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to homopolymers or copolymers wherein the units of formula (1) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/22026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units. In addition, the polymers may contain triplet emitters either in copolymerized form or mixed into a blend. Specifically the combination of the oligomers, polymers or dendrimers of the invention with triplet emitters leads to particularly good results.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropyl naphthalene, pentylbenzene, hexylbenzene, heptylbenzene, octylbenzene, 1,1-bis(3,4-dimethylphenyl)ethane or mixtures of two or more of these solvents.

The present invention therefore further provides a formulation, especially a solution or dispersion, comprising at least one compound of formula (1) or (2) or as per the preferred embodiments detailed above and/or a corresponding oligomer, polymer or dendrimer and at least one further compound, especially a solvent. In this case, the formulation, apart from the compound of formula (1) or (2) and the solvent(s), may also comprise further compounds, for example emitters.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising anode, cathode and at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction see, for example, WO 2005/011013). The organic electroluminescent device of the invention may also be a tandem OLED, especially also for white-emitting OLEDs.

The compound of the invention according to the above-detailed embodiments may be used in different layers, according to the exact structure. Preference is given to an organic electroluminescent device containing a compound of formula (1) or formula (2) or the preferred embodiments set out above as matrix material for phosphorescent or fluorescent emitters, especially for phosphorescent emitters, and/or in an electron-blocking or exciton-blocking layer and/or in a hole transport layer and/or in a hole blocker layer and/or in a hole blocker or electron transport layer, according to the exact substitution.

In a preferred embodiment of the invention, the compound of the invention is used as matrix material for a phosphorescent compound in an emitting layer. In this case, the organic electroluminescent device may contain an emitting layer, or it may contain a plurality of emitting layers, where at least one emitting layer contains at least one compound of the invention as matrix material.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material.

Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Particularly suitable matrix materials which can be used in combination with the compounds of the invention are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or the unpublished application EP 11007693.2, indolocarbazole derivatives, for example according to WO 2007/063754 or WO 2008/056746, indenocarbazole derivatives, for example according to WO 2010/136109 or WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and the unpublished application EP 11003232.3, or triphenylene derivatives, for example according to WO 2012/048781. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Suitable phosphorescent compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531 and WO 2013/020631. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of suitable phosphorescent emitters are the structures depicted in the following table:

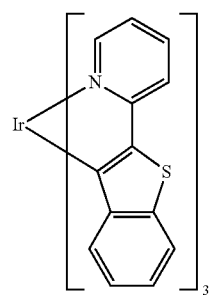
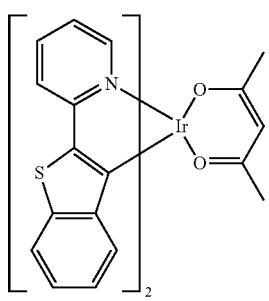
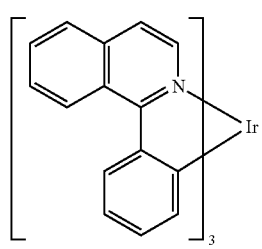
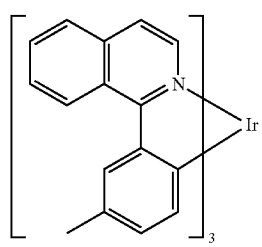
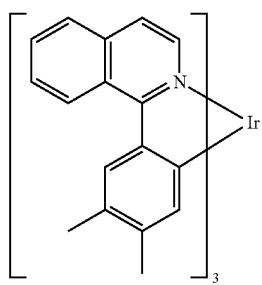
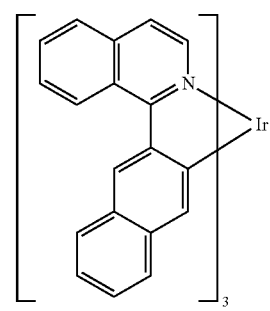
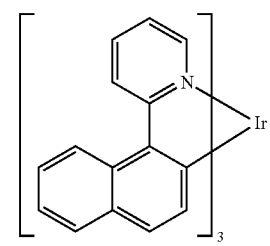
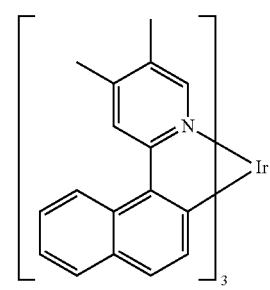
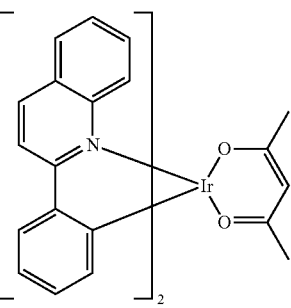
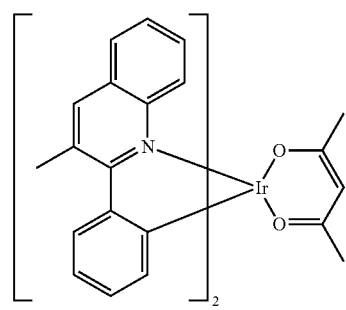

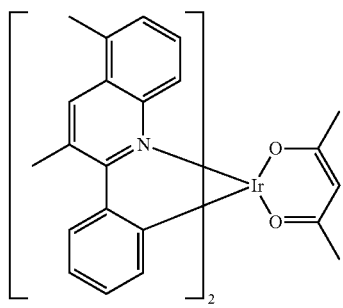
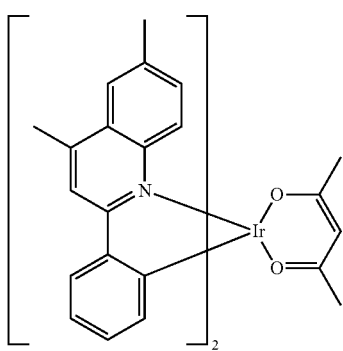
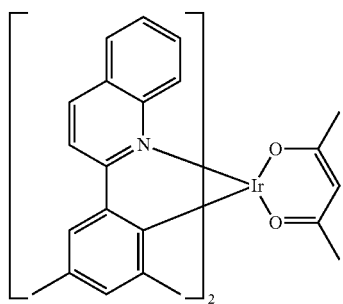
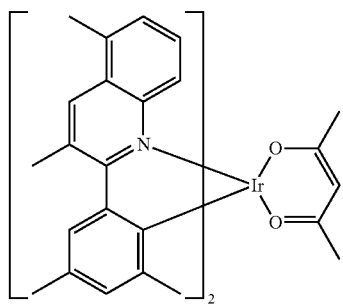
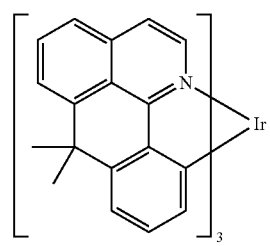
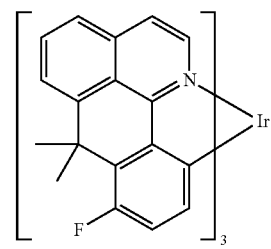
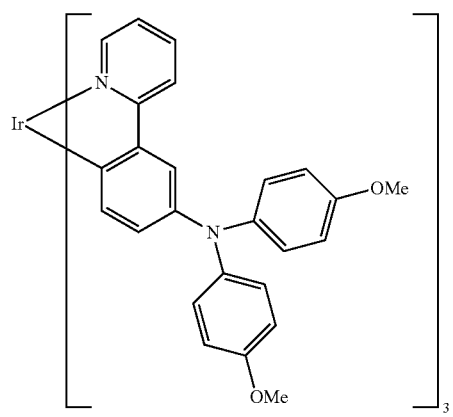
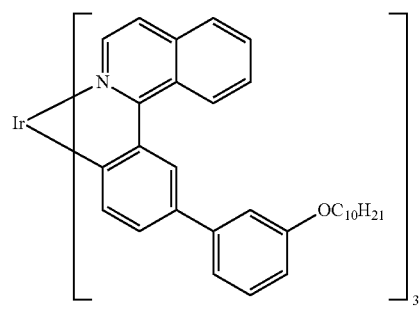
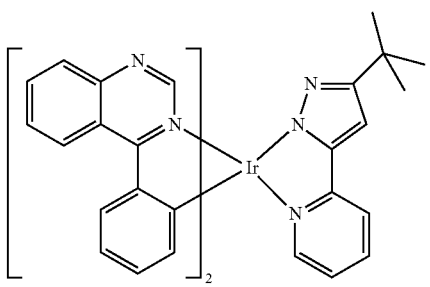
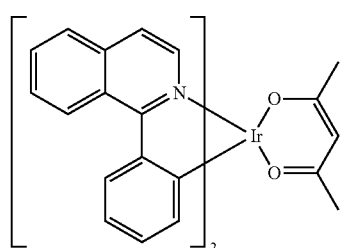

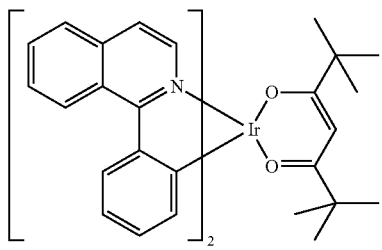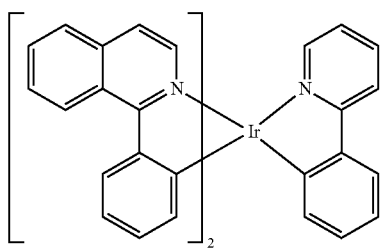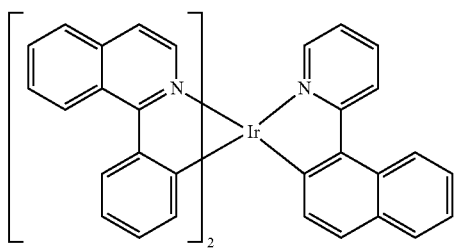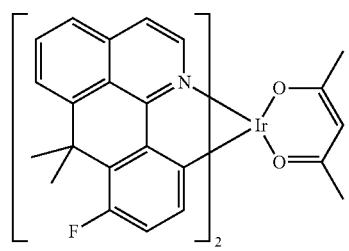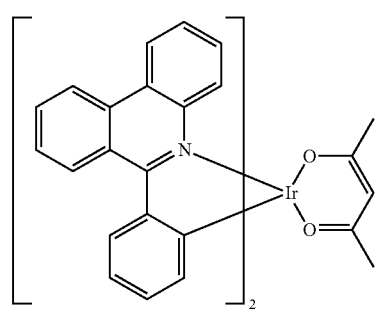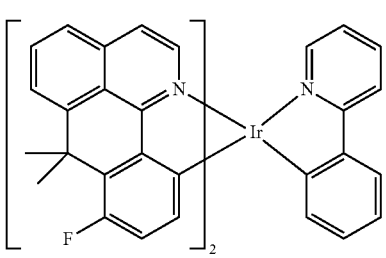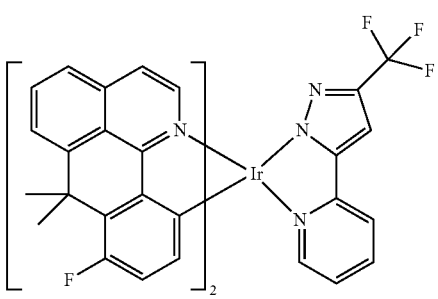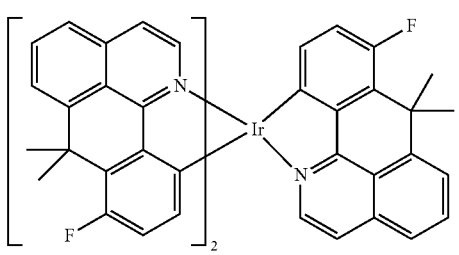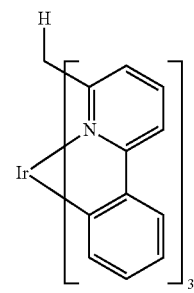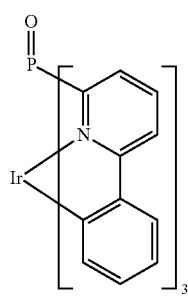

95
-continued
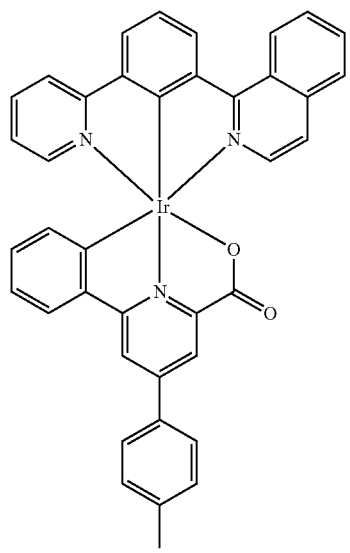
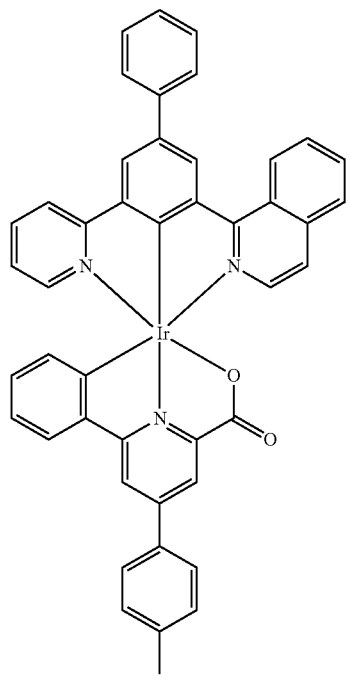
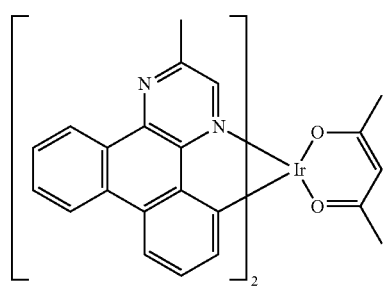
96
-continued
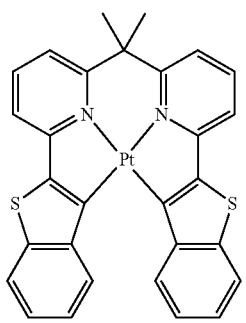
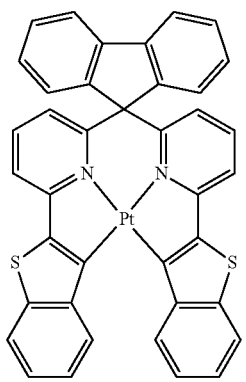
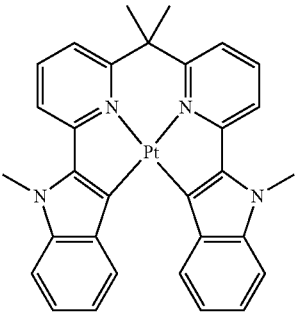
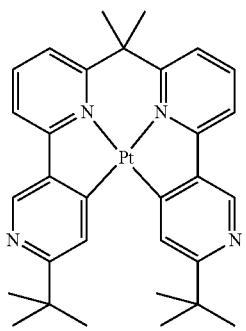

| 97 -continued | 98 -continued |
|---|---|
| 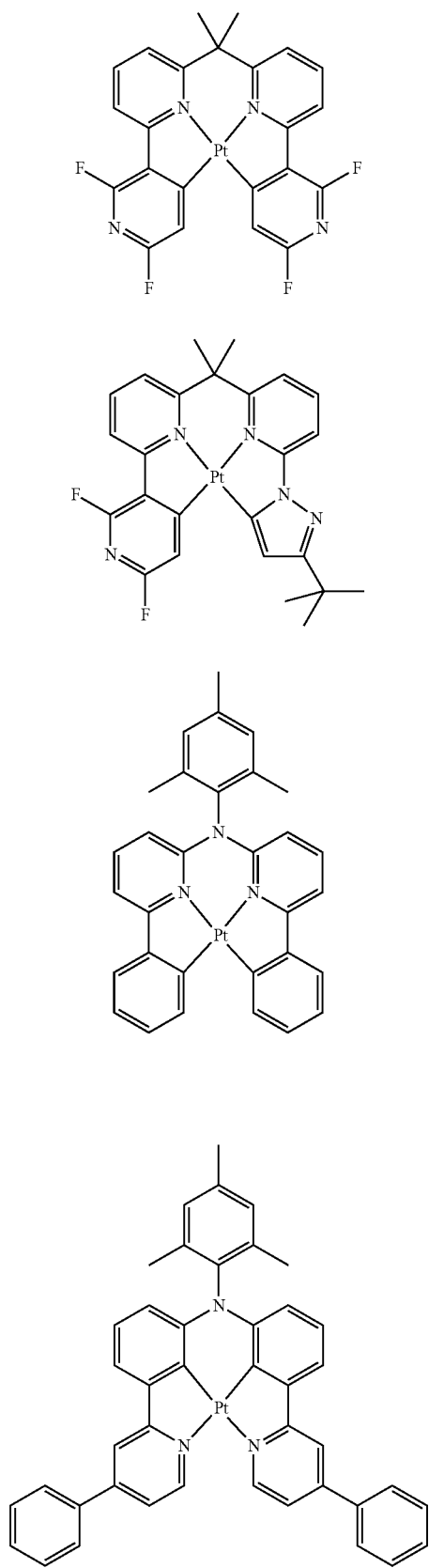 | 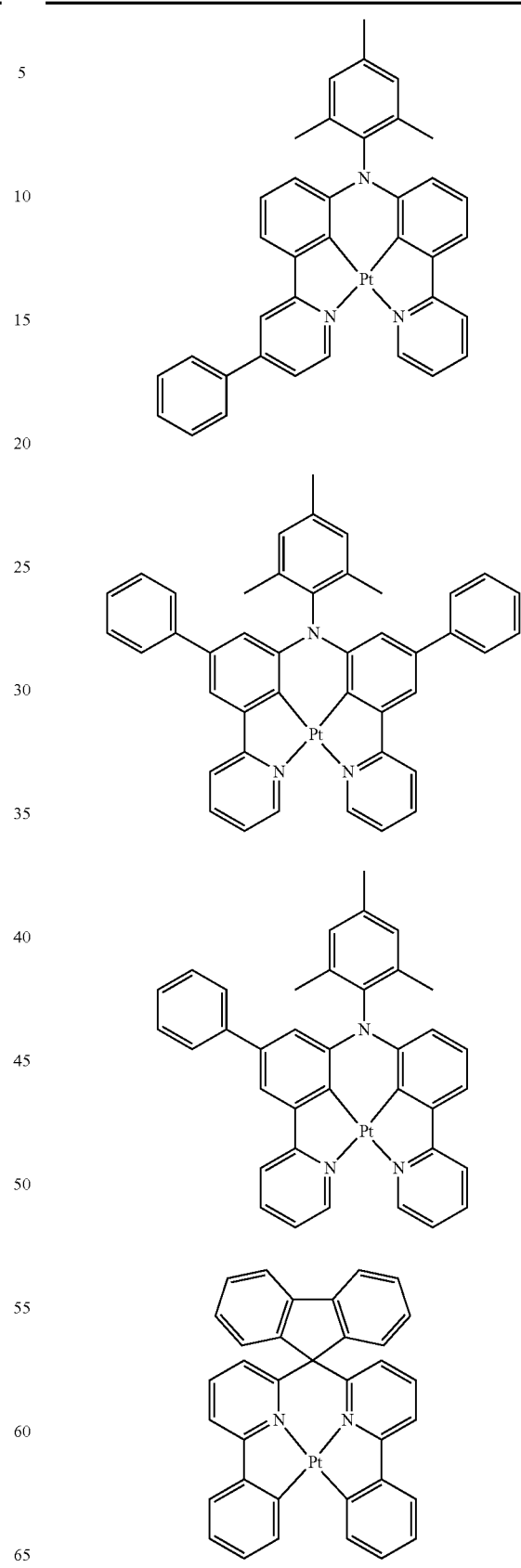 |

| 99 -continued | 100 -continued |
|---|---|
| 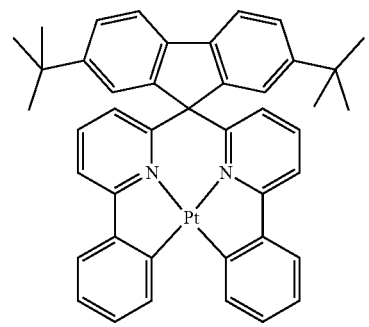 | 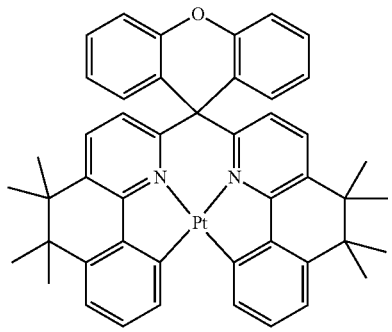 |
| 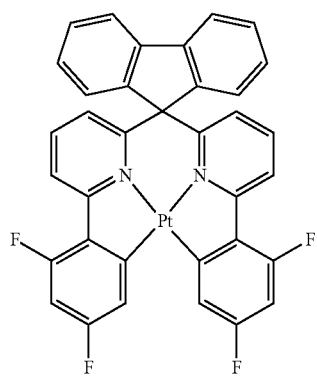 | 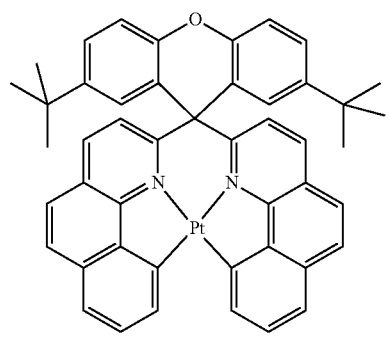 |
| 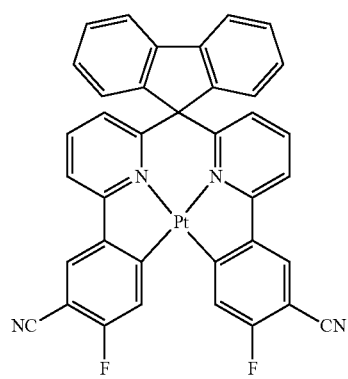 | 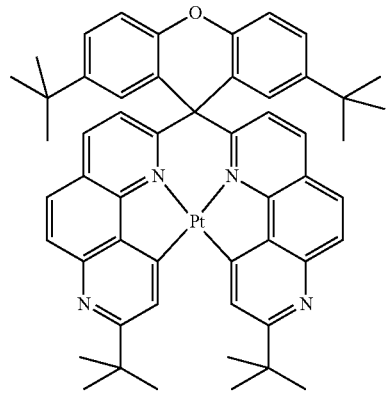 |
| 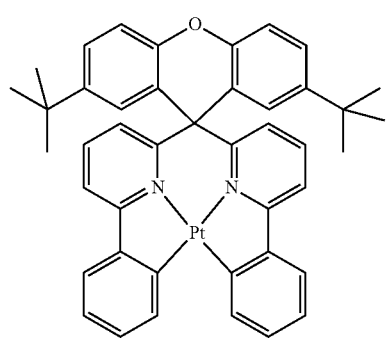 | 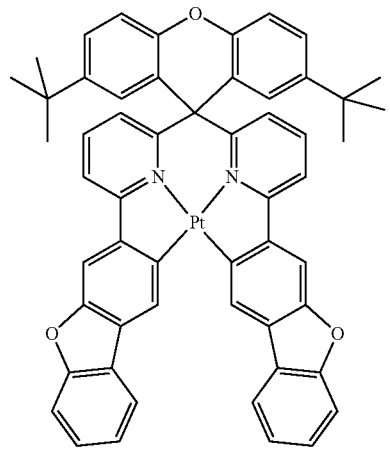 |

101
-continued
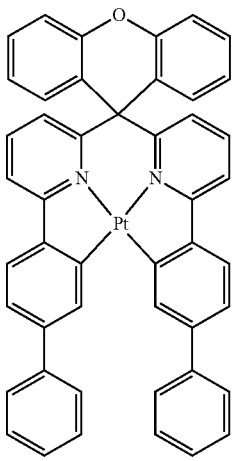
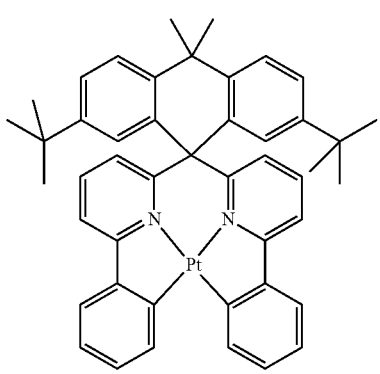
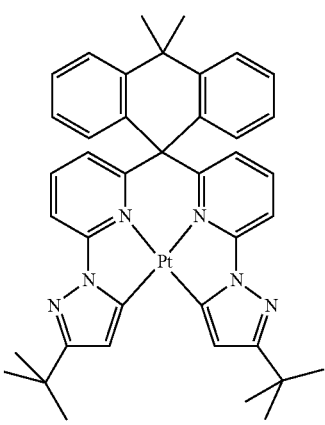
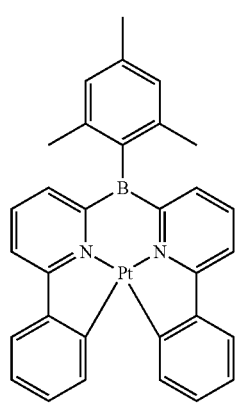
102
-continued
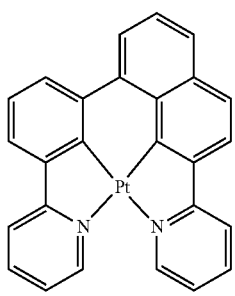
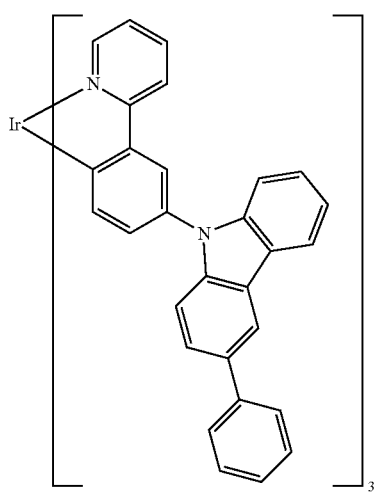
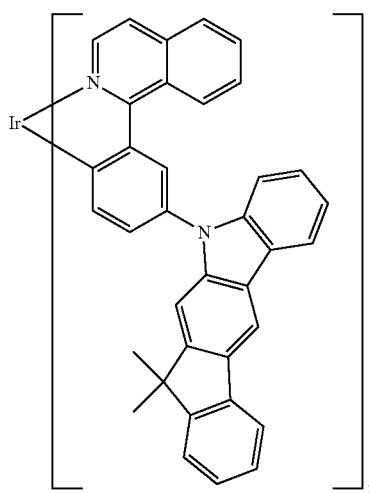
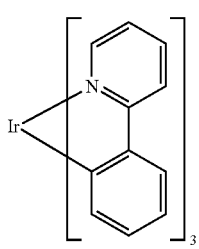

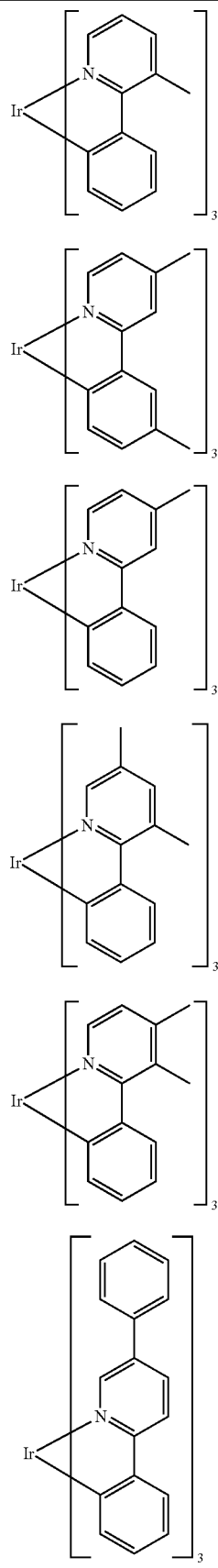
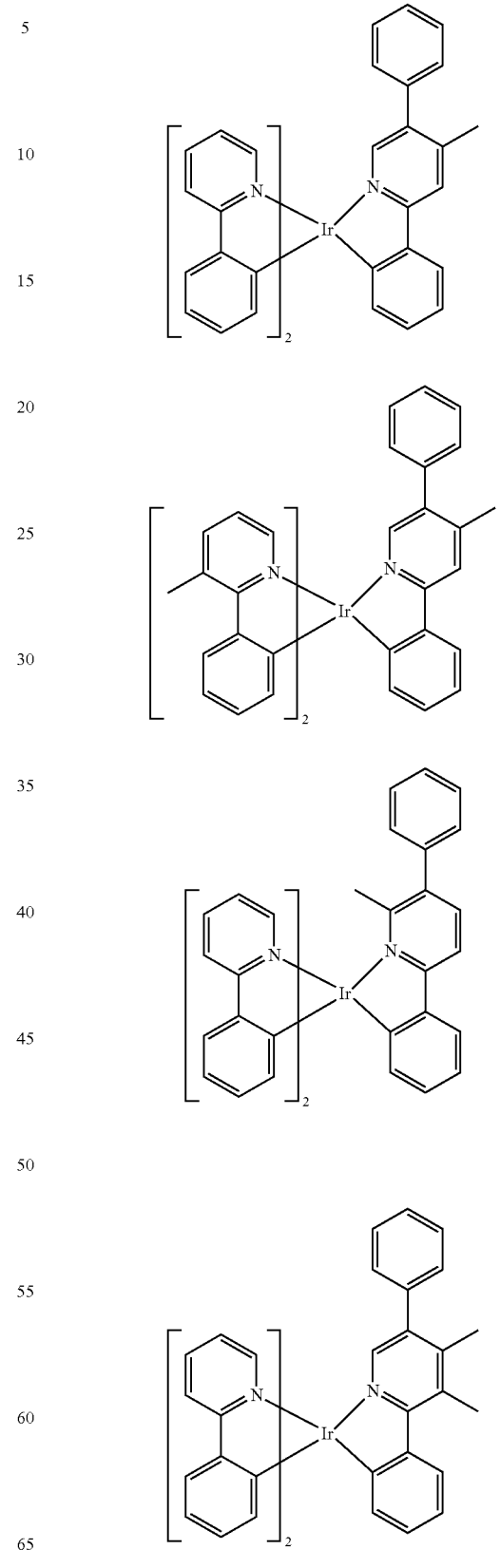

105
-continued
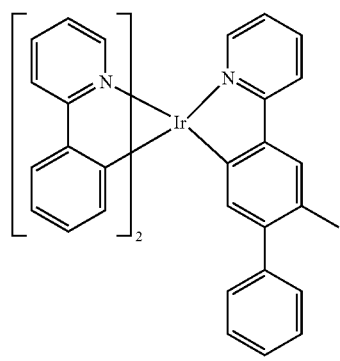
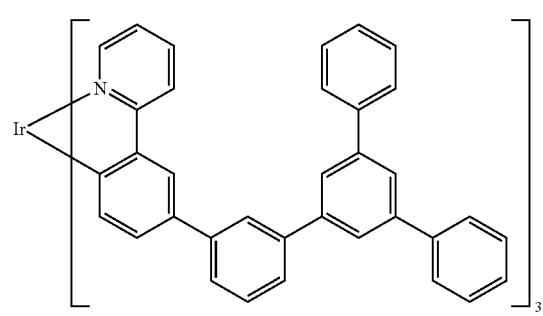
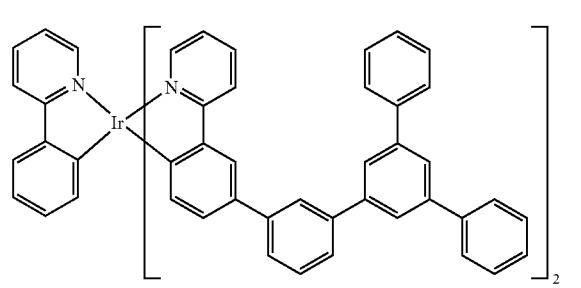
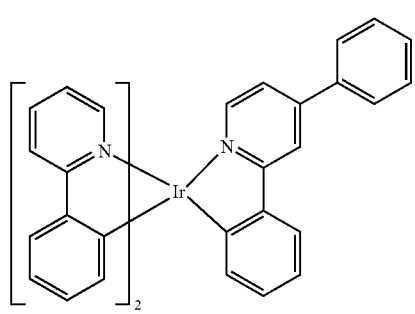
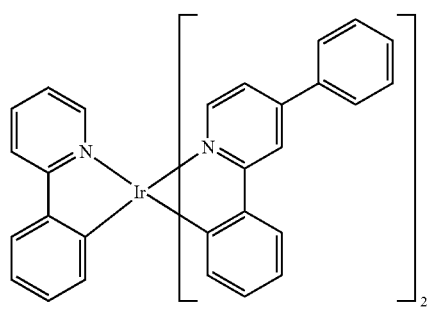
106
-continued
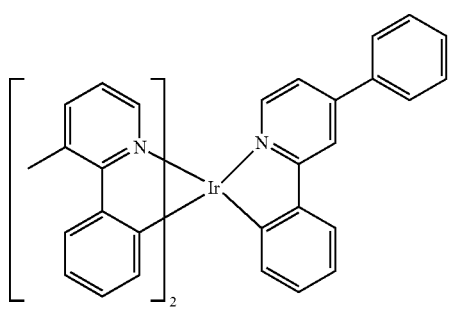
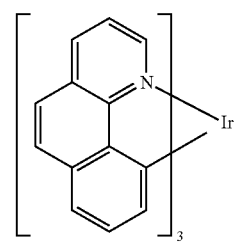
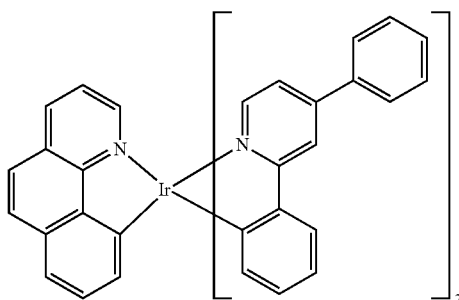
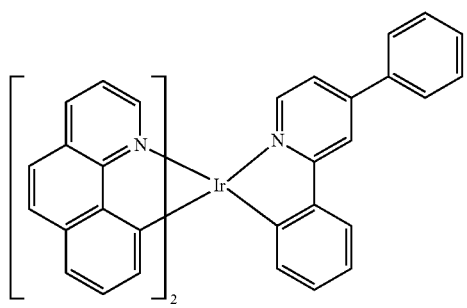
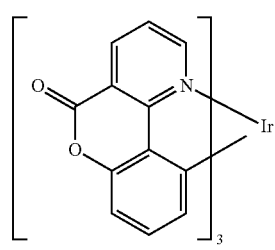

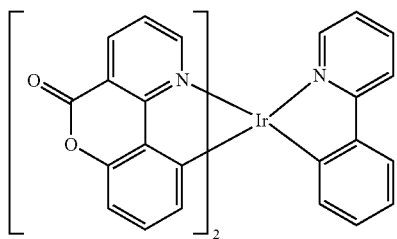
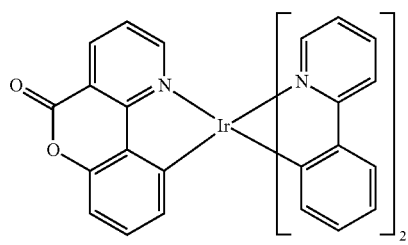
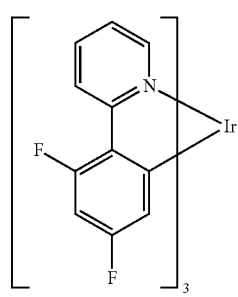
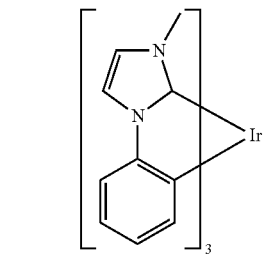
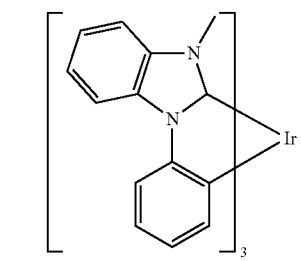
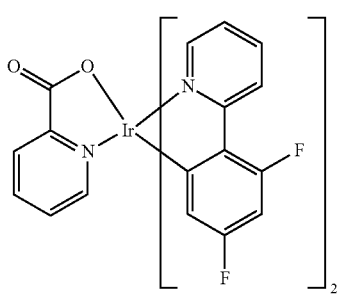
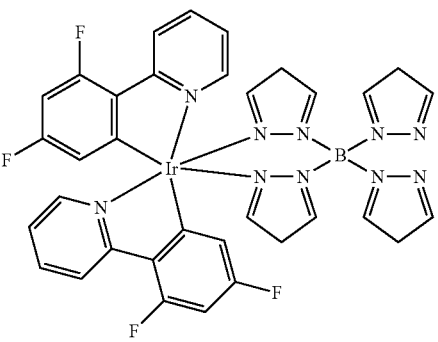
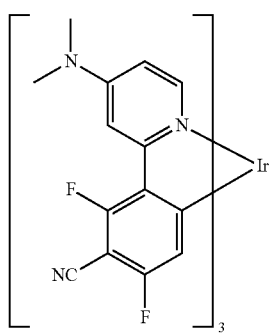
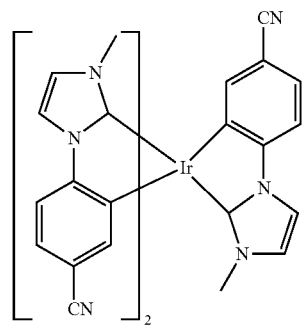

109
-continued
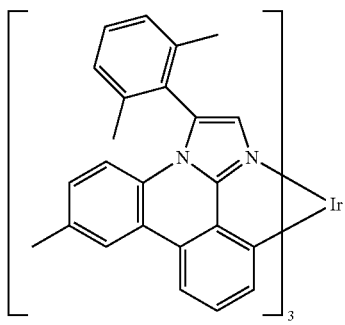
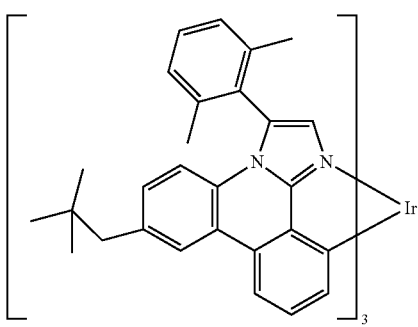
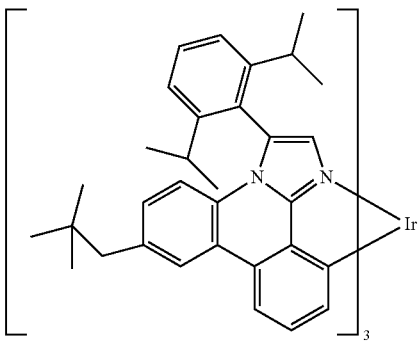
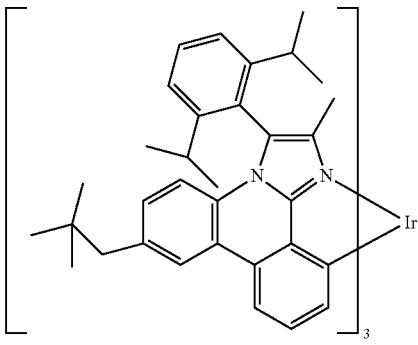
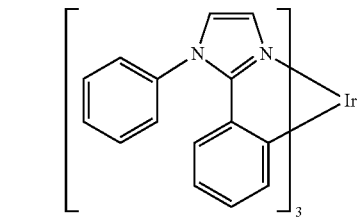
110
-continued
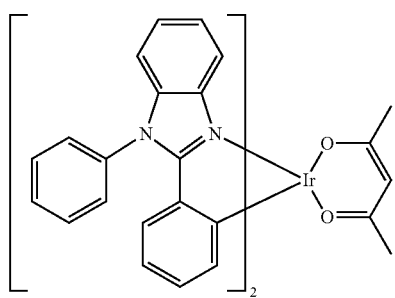
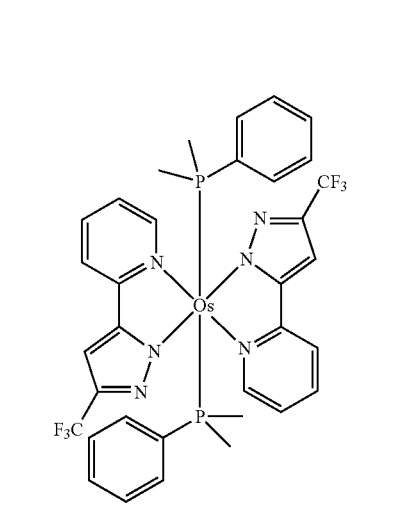
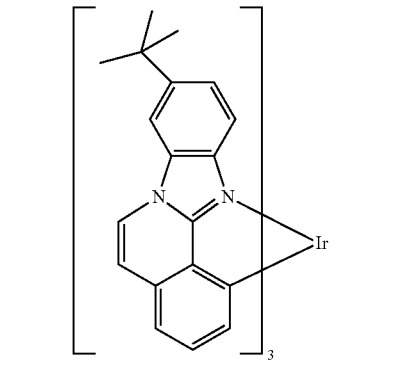
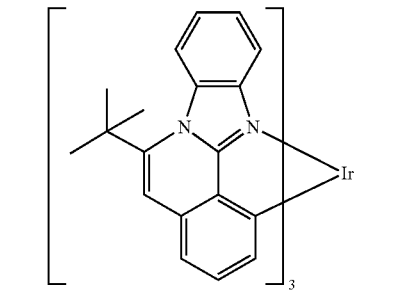

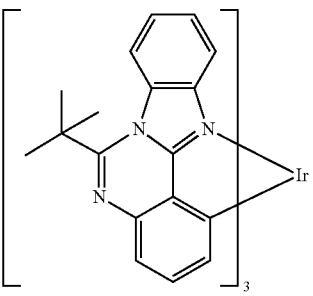

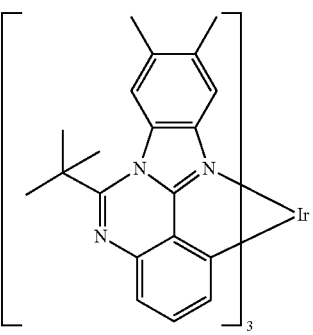

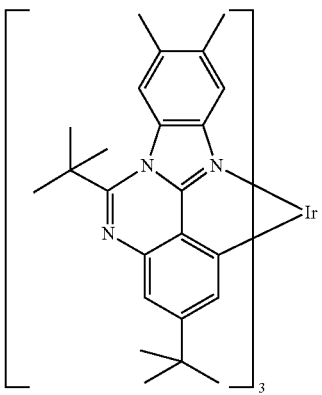

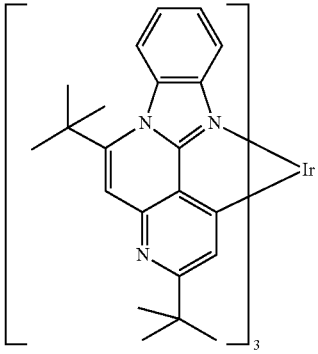

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In a further embodiment of the invention, the compound of the invention is used in a hole transport layer or in an electron blocker layer or exciton blocker layer.

In yet a further preferred embodiment of the invention, the compound of the invention is used as electron transport material in an electron transport or electron injection layer. In this case, the emitting layer may be fluorescent or phosphorescent. When the compound is used as electron transport material, it may be preferable for it to be doped, for example with alkali metal complexes, for example LiQ (lithium hydroxyquinolinate).

In yet a further preferred embodiment of the invention, the compound of the invention is used in a hole blocker layer. A hole blocker layer is understood to be a layer which directly adjoins an emitting layer on the cathode side.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:

1. The compounds of the invention, used as matrix material for fluorescent or phosphorescent emitters, lead to long lifetimes. This is especially true when the compounds are used as matrix material for a phosphorescent emitter.

2. The compounds of the invention lead to very low operating voltages. This is especially true when the compounds are used as matrix material for a phosphorescent emitter.

These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

Example 1: Synthesis of 8-bromodibenzo[b,d]pyran-6-one

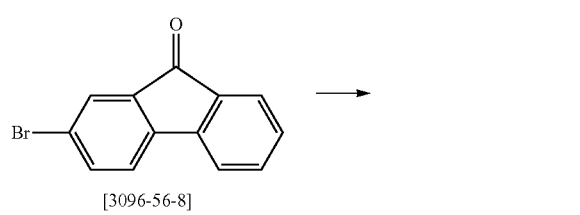

[3096-56-8]

100 g (386 mmol) of 2-bromofluorenone are initially charged in 1000 mL of trifluoroacetic acid and cooled to 0° C. Added gradually to this solution are 100 g (637 mmol) of sodium percarbonate (13%-14% active oxygen), and the reaction mixture is stirred at 10-15° C. for 1 h. Subsequently, stirring of the mixture continues at room temperature overnight. 1000 mL of water are added to the reaction mixture, and the organic phase is removed and then concentrated to dryness. The residue is triturated with heptane, filtered off with suction and dried at 50° C. under reduced pressure. Yield: 92 g (334 mmol), 86% of theory Example 2: Synthesis of 8-(2-chlorophenylamino) dibenzo[b,d]pyran-6-one

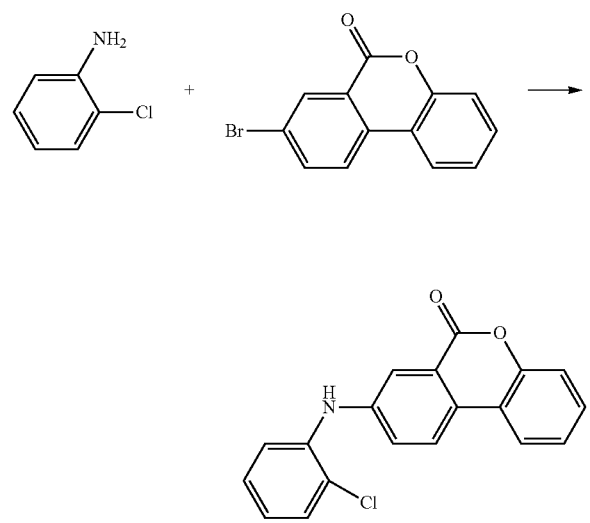

21 g (79 mmol) of 8-bromodibenzo[b,d]pyran-6-one, 10 mL (95 mmol) of 2-chloroaniline, 36.3 g (111 mmol) of cesium carbonate, 0.89 g (3.9 mmol) of palladium(II) acetate and 3.9 g (6 mmol) of 2,2'-bis(diphenylphosphanyl)-[1,1'] binaphthyl are dissolved in 500 mL of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colorless solid. Yield: 19 g (59 mmol); 76% of theory In an analogous manner, it is possible to prepare the following compounds:

| Reactant | Product | Yield |
|---|---|---|
| 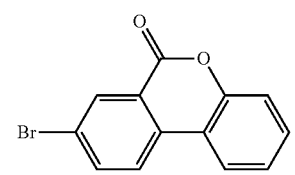 [1443434-82-9] | | 80% |

-continued
| Reactant | Product | Yield |
|---|---|---|
| 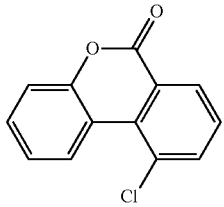<br>[1000391-25-2] | 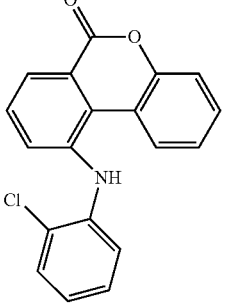 | 32% |
| 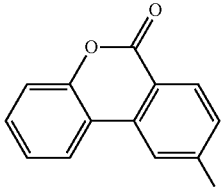<br>[145786-47-6] | 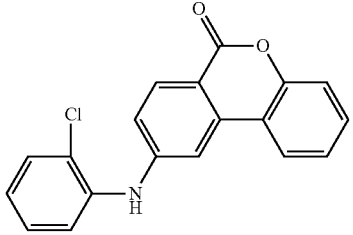 [SMILES: O=c1oc2ccccc2c2cc(Nc3ccccc3Cl)ccc12] | 87% |
| 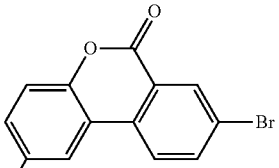<br>[100527-53-5] | 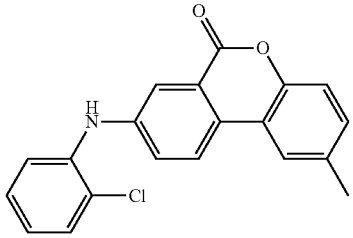 [SMILES: Cc1ccc2oc(=O)c3cc(Nc4ccccc4Cl)ccc3c2c1] | 83% |
| 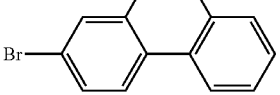<br>[1433988-13-6] | 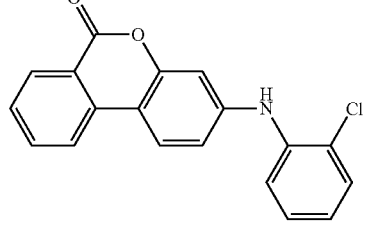 | 79% |
| 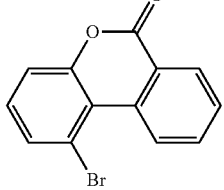<br>[928307-80-6] | 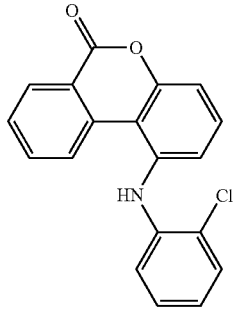 [SMILES: O=c1oc2cccc(Nc3ccccc3Cl)c2c2ccccc12] | 84% |
| 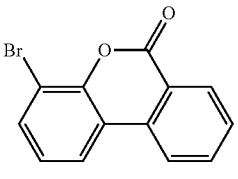<br>[158097-94-0] | 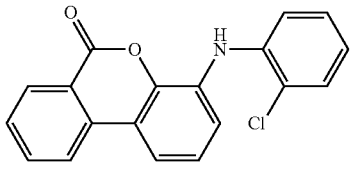 [SMILES: O=c1oc2c(Nc3ccccc3Cl)cccc2c2ccccc12] | 79% |

| Reactant | Product | Yield |
|---|---|---|
| 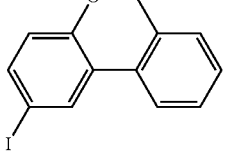 [151648-54-3] | 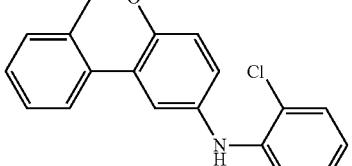 | 83% |
| 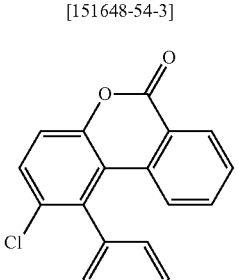 [1130141-14-8] | 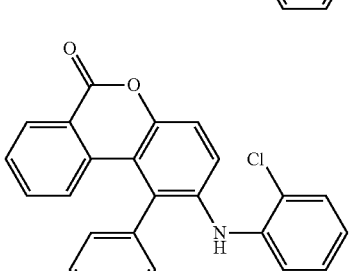 | 29% |
| 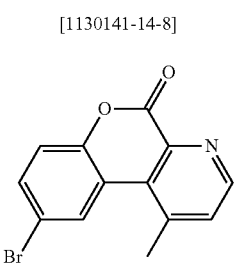 [585529-39-1] | 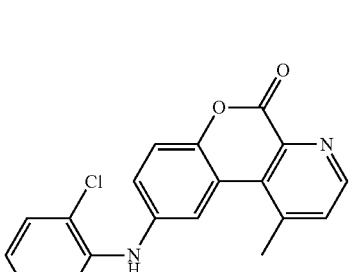 | |
| 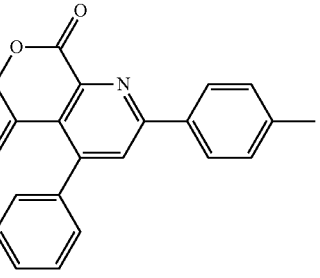 [1414381-93-3] | 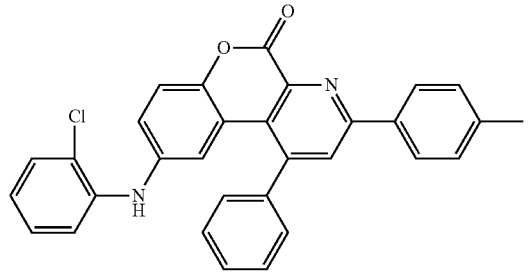 [SMILES: Cc1ccc(-c2cc(-c3ccccc3)c3c(n2)c(=O)oc2ccc(Nc4ccccc4Cl)cc23)cc1] | |
In an analogous manner, it is possible to prepare the following compound with 0.5 equivalent of dibenzo[b,d]pyran-6-one:
| Reactant 1 | Product | Yield |
|---|---|---|
| 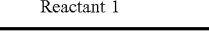 [18102-99-3] | 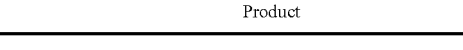 | 76% |

Example 3: Synthesis of 8H-5-oxa-8-azaindeno[2,1-b]phenanthren-6-one

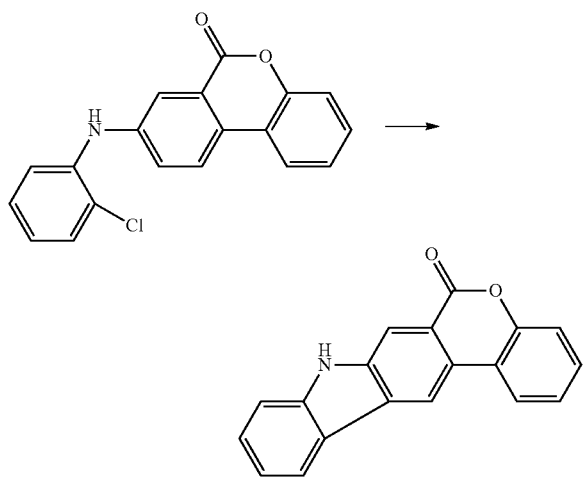

17 g (102 mmol) of 8-(2-chlorophenylamino)dibenzo[b,d]pyran-2-one, 32 g (268 mmol) of potassium carbonate, 0.6 g (2.7 mmol) of palladium(II) acetate and 4.2 mL (4.2 mmol) of tri-tert-butylphosphine are suspended in 350 mL of dimethylacetamide and stirred under reflux for 6 h. After the reaction mixture has cooled, 300 mL of water and 400 mL of ethyl acetate are added. The mixture is stirred for a further 30 min, the organic phase is separated off and filtered through a short Celite bed, and then the solvent is removed under reduced pressure. The crude product is subjected to hot extraction with toluene and recrystallized from toluene. The product is isolated as a beige solid. Yield: 13.5 g (74 mmol); 90% of theory In an analogous manner, it is possible to prepare the compounds below. In the case of formation of isomers, these can be separated by chromatography.

| Reactant 1 | Product 1 | Yield | Product 2 | Yield |
|---|---|---|---|---|
| | | 90% | | |
| | | 89% | | |
| | | 64% | | 30% |
| | | 71% | | 25% |

-continued

| Reactant 1 | Product 1 | Yield | Product 2 | Yield |
|---|---|---|---|---|
|  |  | 45% |  | 40% |
|  |  | 78% |  |  |
|  |  | 85% |  |  |
|  |  | 62% |  | 27% |

-continued

| Reactant 1 | Product 1 | Yield | Product 2 | Yield |
|---|---|---|---|---|
| | | 79% | | |
| | | 56% | | 21% |
| | | 45% | | |

In an analogous manner, it is possible to prepare the following compound with 0.5 equivalent of the chloro compound:

| Reactant 1 | Product | Yield |
|---|---|---|
|  |  | 66% |

Example 4: Synthesis of N-phenyl-8H-5-oxa-8-azaindeno[2,1-b]phenanthren-6-one

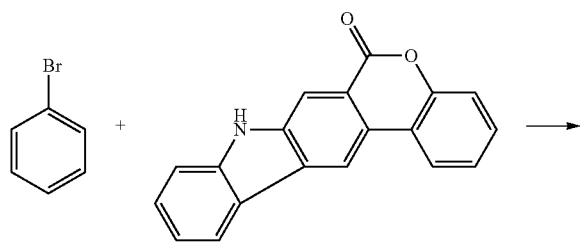

→

-continued

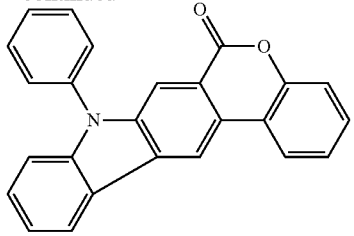

30 g (106 mmol) of 8H-5-oxa-8-azaindeno[2,1-b]phenanthren-6-one, 17.9 g (114 mmol) of bromobenzene and 30.5 g of NaOtBu are suspended in 1.5 L of p-xylene. To this suspension are added 0.5 g (2.11 mmol) of Pd(OAc)$_2$ and 6 mL of a 1M tri-tert-butylphosphine (1 M solution in toluene). The reaction mixture is heated under reflux for 16 h. After cooling, the organic phase is removed, washed three times with 200 mL each time of water and then concentrated to dryness. The residue is hot-extracted with toluene, recrystallized from toluene and finally sublimed under high vacuum; purity is 99.9% at a yield of 15 g (42 mmol; 56%).

In an analogous manner, it is possible to prepare the compounds below:

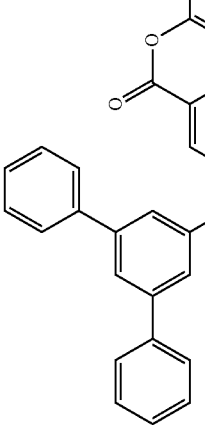

| Reactant 1 | Reactant 2 | Product | Yield |
|---|---|---|---|
| 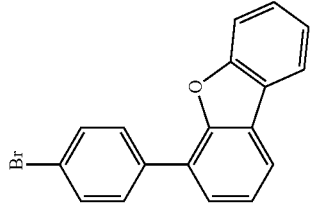 | 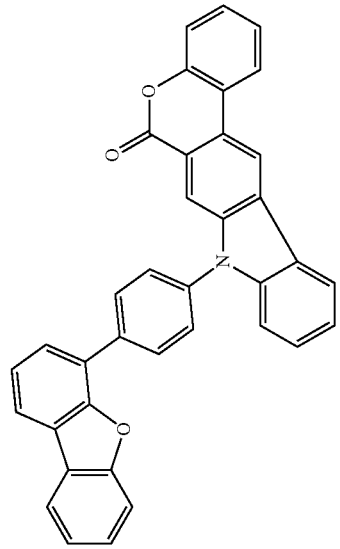 [955959-84-9] | 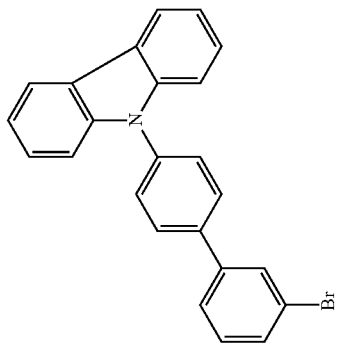 | 84% |
| 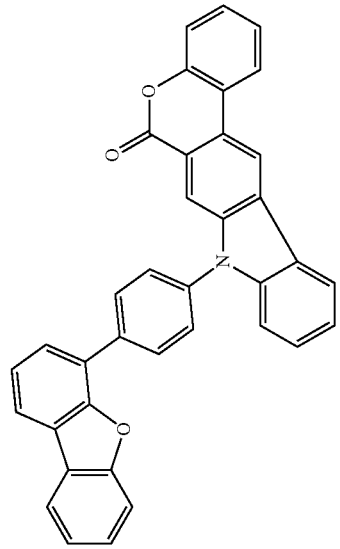 | 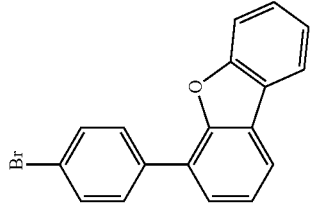 [854952-47-9] | 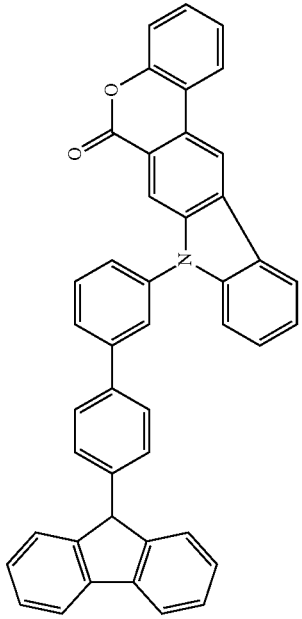 | 87% |

| Reactant 1 | Reactant 2 | Product | Yield |
|---|---|---|---|
| (chromeno-carbazolone) | N-phenyl-dimethylfluorene-carbazole bromide [1257220-44-2] | | 87% |
| (chromeno-carbazolone) | N-(biphenyl)-N-(3-bromophenyl)-biphenylamine [952431-31-1] | | 83% |

-continued

| Reactant 1 | Reactant 2 | Product | Yield |
|---|---|---|---|
| (chromeno-indole lactone, NH) | 3-bromo-9-phenylcarbazole [1153-85-1] | | 82% |
| (chromeno-indole lactone, NH) | 2-(3-bromophenyl)-4,6-diphenyl-1,3,5-triazine [864377-31-1] | | 83% |

| Reactant 1 | Reactant 2 | Product | Yield |
|---|---|---|---|
| 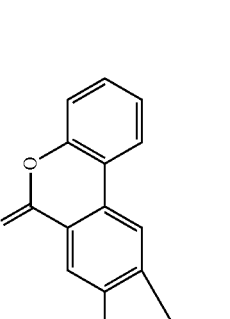 | 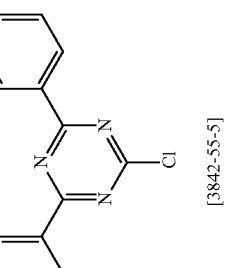 [3842-55-5] | 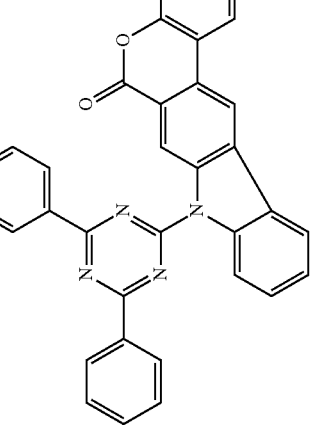 | 80% |
| 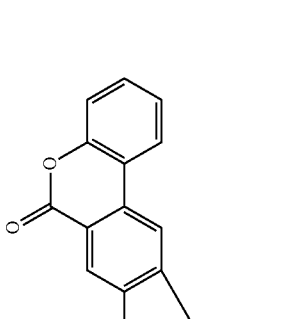 | 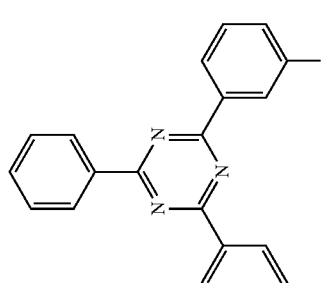 [1269508-31-7] | 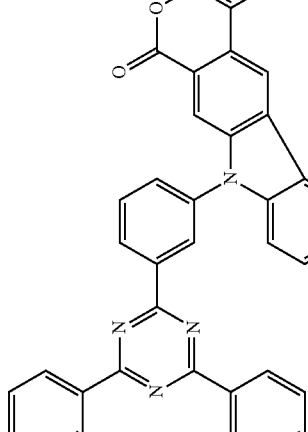 | 85% |

| Reactant 1 | Reactant 2 | Product | Yield |
|---|---|---|---|
| 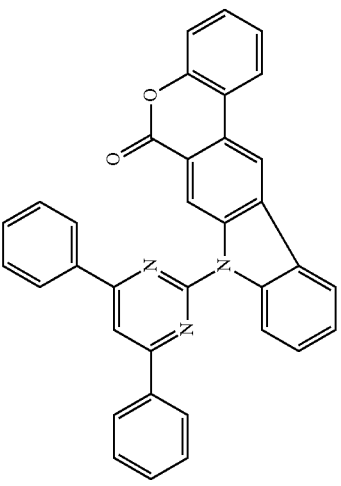 | 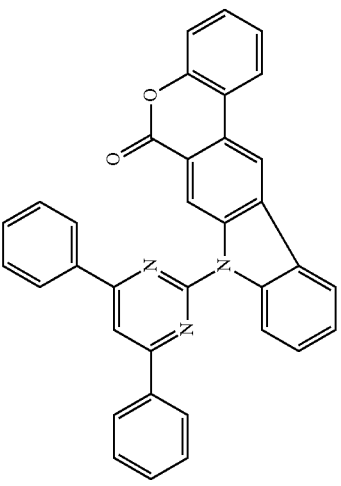 [56181-49-8] | 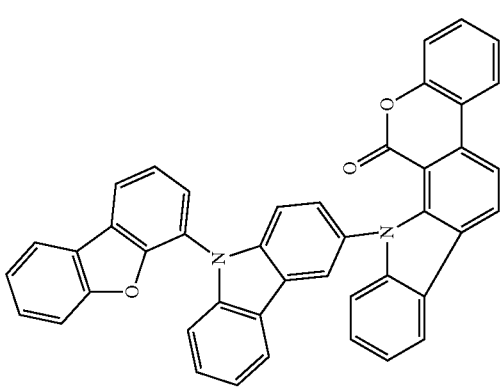 | 84% |
| 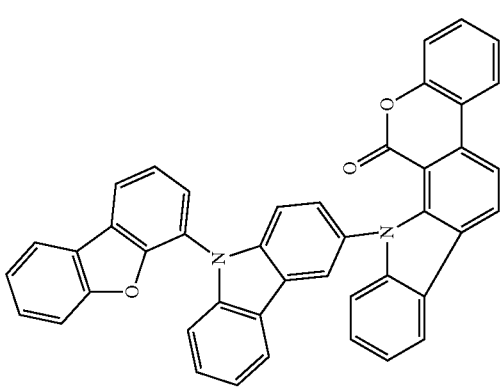 | 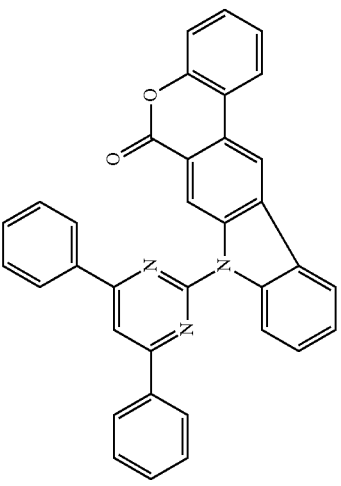 [1345970-20-8] | 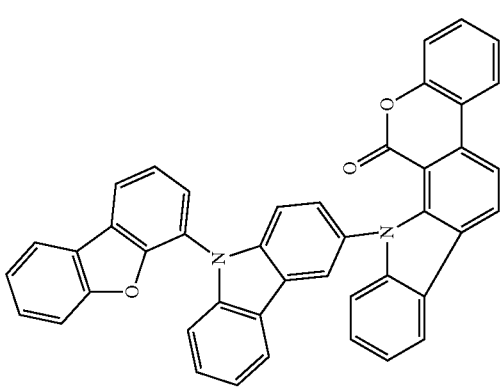 | 88% |

| Reactant 1 | Reactant 2 | Product | Yield |
|---|---|---|---|
| | 864377-28-6 | | 82% |
| | [63524-03-8] | | 84% |

| Reactant 1 | Reactant 2 | Product | Yield |
|---|---|---|---|
| 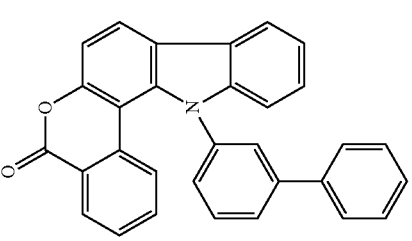 | 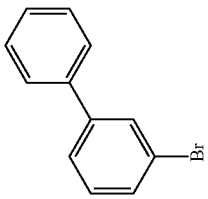 [21113-57-7] | 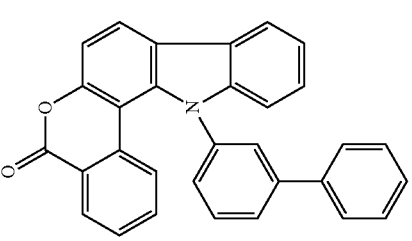 | 80% |
| 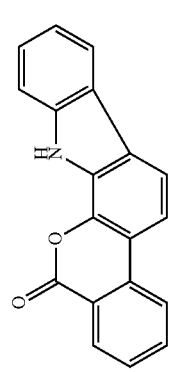 | 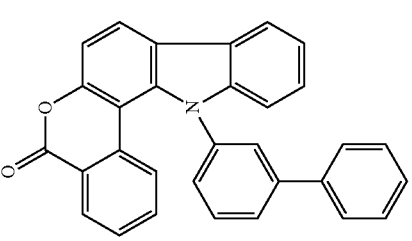 [21113-57-7] | 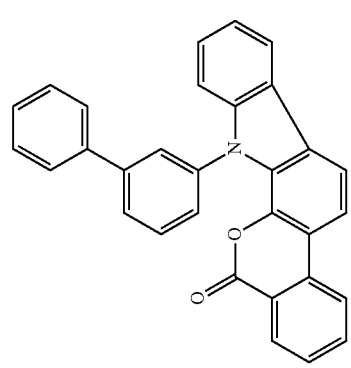 | 81% |

-continued
| Reactant 1 | Reactant 2 | Product | Yield |
|---|---|---|---|
| 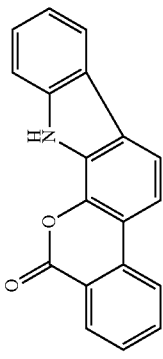 | 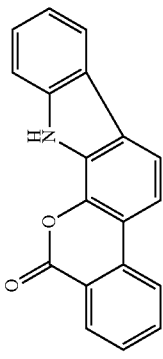 [3842-55-5] | 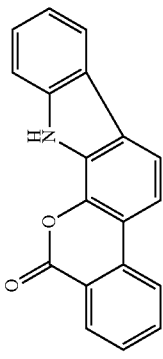 | 86% |
| 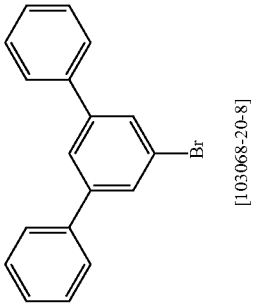 | 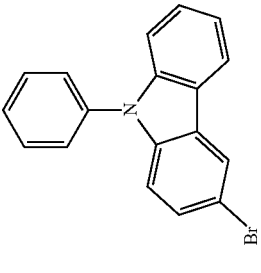 [1153-85-1] | 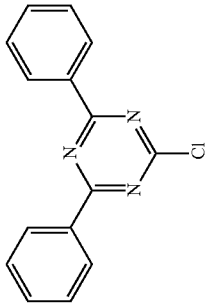 | 87% |
| 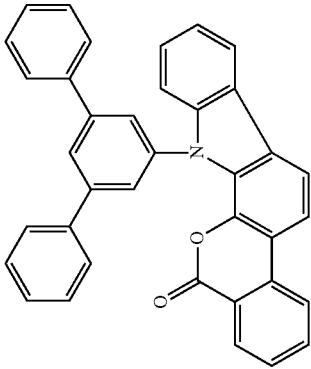 | 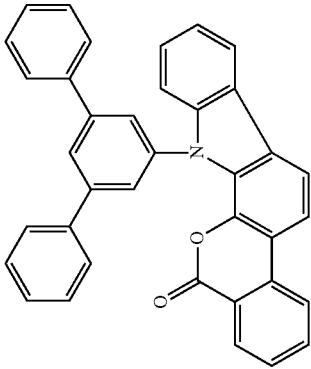 [103068-20-8] | 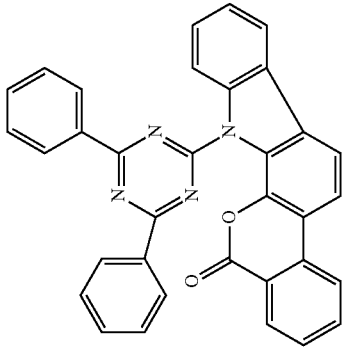 | 87% |

-continued
| Reactant 1 | Reactant 2 | Product | Yield |
|---|---|---|---|
| 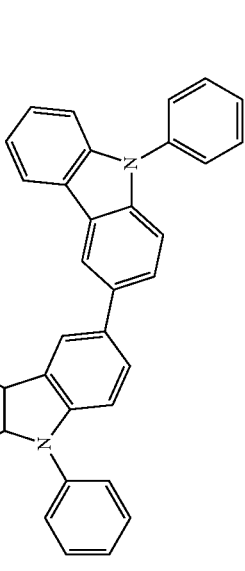 | 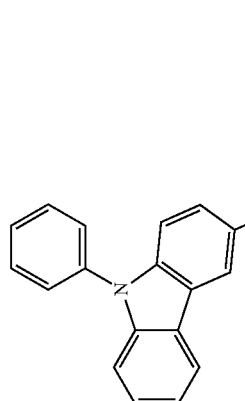 [918137-84-5] | 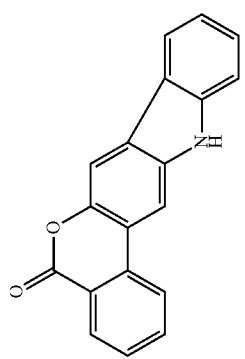 | 83% |
| 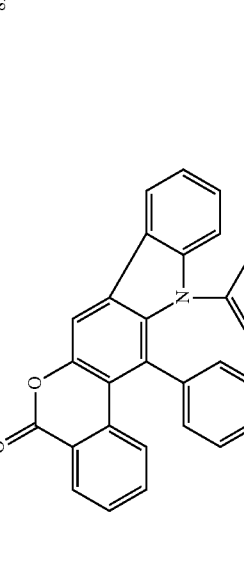 | 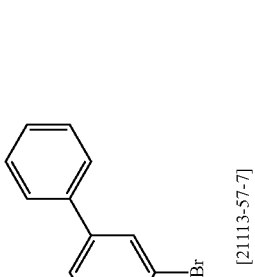 [211113-57-7] | 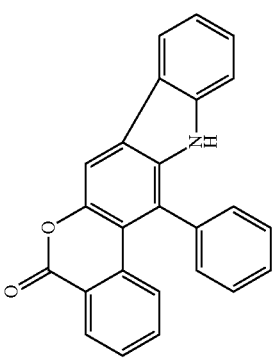 | 82% |

-continued

| Reactant 1 | Reactant 2 | Product | Yield |
|---|---|---|---|
| (indolo-chromenone NH compound) | dibenzofuran-Br [86-76-0] | N-(dibenzofuranyl) product | 88% |
| (indolo-chromenone NH compound) | 3,5-diphenylbromobenzene [103068-20-8] | N-(3,5-diphenylphenyl) product | 85% |
| (indolo-chromenone NH compound) | Ph–Br | N-phenyl product | 73% |

| Reactant 1 | Reactant 2 | Product | Yield |
|---|---|---|---|
| 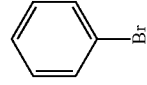 | 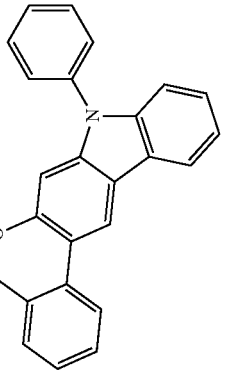 | 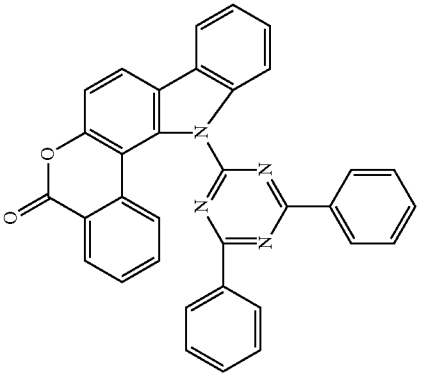 | 89% |
| 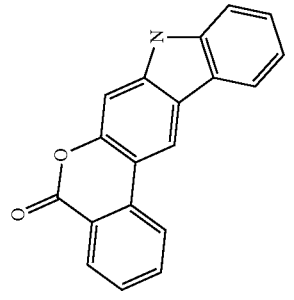 | 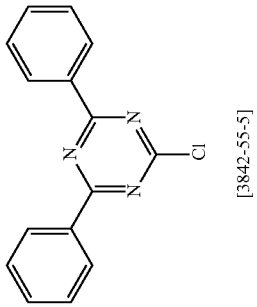 [3842-55-5] | 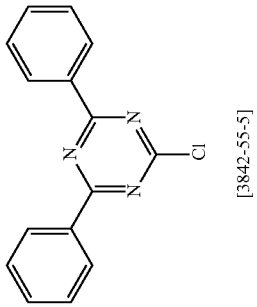 | 80% |

-continued
| Reactant 1 | Reactant 2 | Product | Yield |
|---|---|---|---|
| 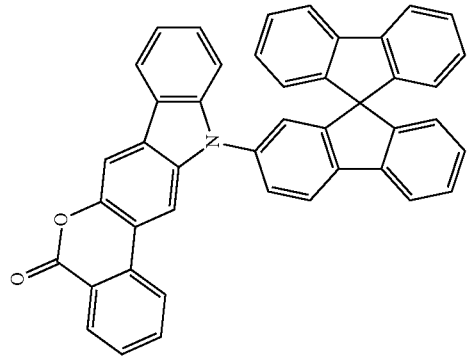 | 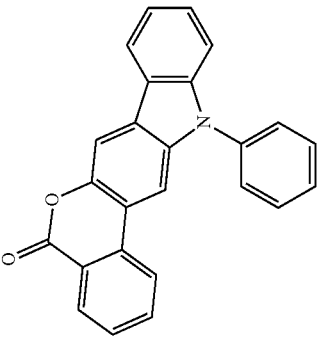 | 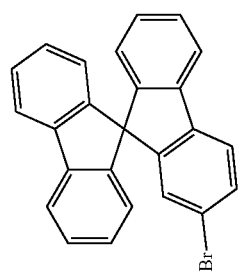 | 84% |
| 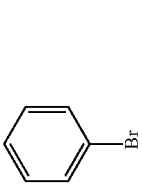 | Ph-Br | | 87% |

| Reactant 1 | Reactant 2 | Product | Yield |
|---|---|---|---|
| 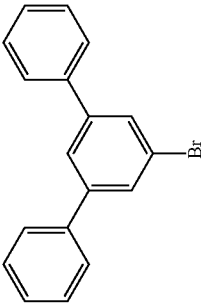 | 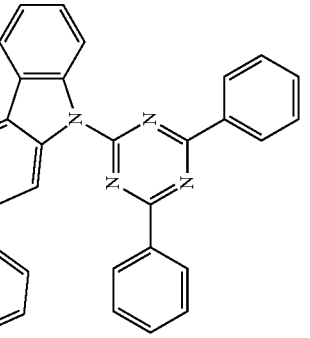 [3842-55-5] | 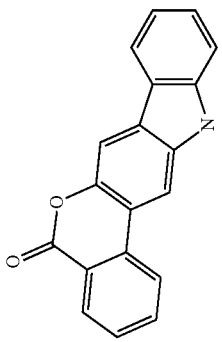 | 86% |
| 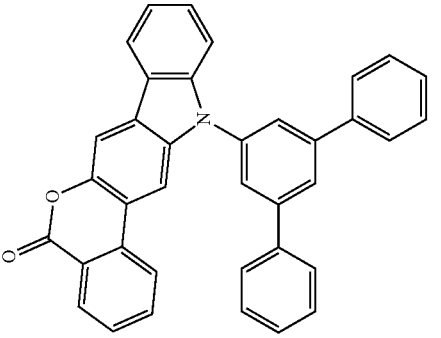 | 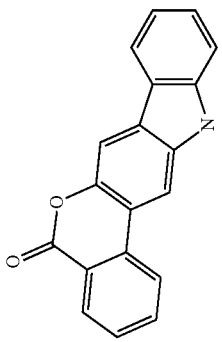 [103068-20-8] | 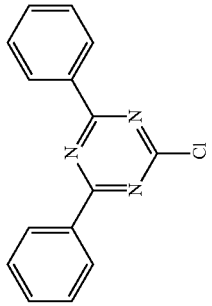 | 87% |

-continued

| Reactant 1 | Reactant 2 | Product | Yield |
|---|---|---|---|
| [1351633-06-1] | [103068-20-8] | | 88% |
| [1351633-06-1] | [1153-85-1] | | 80% |

| Reactant 1 | Reactant 2 | Product | Yield |
|---|---|---|---|
| (structure) | (structure) [103068-20-8] | (structure) | 76% |
| (structure) | (structure) | (structure) | 65% |

In an analogous manner, it is possible to prepare the following compounds with 0.5 equivalent of the chloro compound:

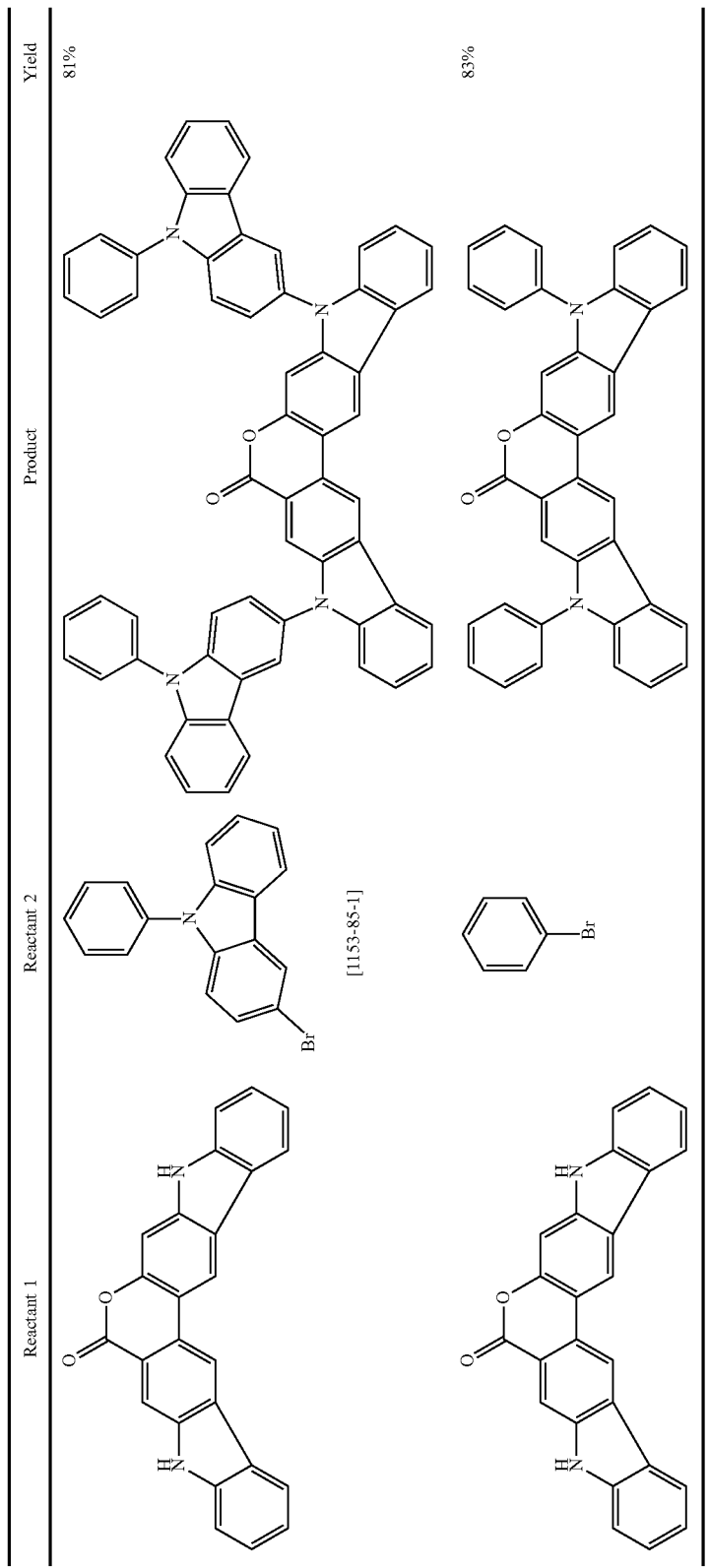

In an analogous manner, it is possible to prepare the following compounds with 0.5 equivalent of the haloaromatic compound:

| Reactant 1 | | Product | Yield |
|---|---|---|---|
| | [108-36-1] | | 75% |
| | | | 72% |

Example 5: Synthesis of 8-(4-bromophenyl)-8H-5-oxa-8-azaindeno[2,1-b]phenanthren-6-one

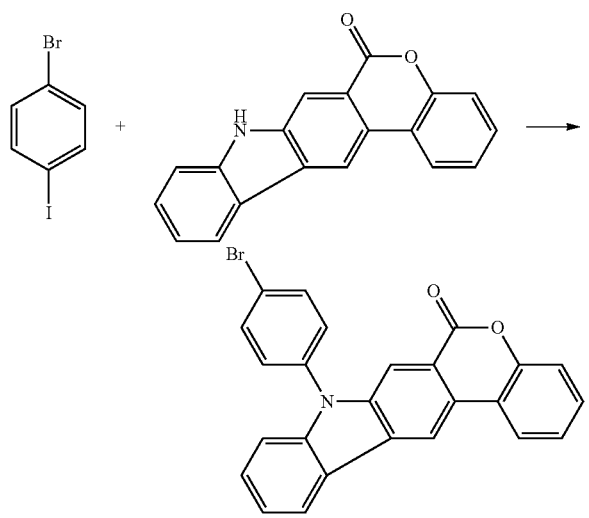

23 g (81 mmol) of 8H-5-oxa-8-azaindeno[2,1-b]phenanthren-6-one, 115 g (406 mmol) of 1-bromo-4-iodobenzene, 22.4 g (162 mmol) of potassium carbonate, 1.84 g (8.1 mmol) of 1,3-di(2-pyridyl)propane-1,3-dione, 1.55 g (8.1 mmol) of copper iodide and 1000 mL of DMF are heated under reflux for 30 h. Subsequently, the reaction mixture is concentrated to dryness on a rotary evaporator. The residue is dissolved in THF and filtered through a short silica gel bed, then the solvent is removed under reduced pressure. Subsequently, the solid material is recrystallized from heptane/THF and hot-extracted with heptane/toluene over alumina. The solid material that precipitates out in the course of cooling is filtered and dried. Yield: 28 g (64 mmol), 80%

In an analogous manner, it is possible to prepare the following compounds:

| Reactant 1 | Reactant 2 | Product | Yield |
|---|---|---|---|
| | 583-55-1 | | 74% |

| Reactant 1 | Reactant 2 | Product | Yield |
|---|---|---|---|
| | | | 69% |

Example 6: Synthesis of 8H-5-oxa-8-azaindeno[2,1-b]phenanthren-6-one-8-[4-phenylboronic acid]

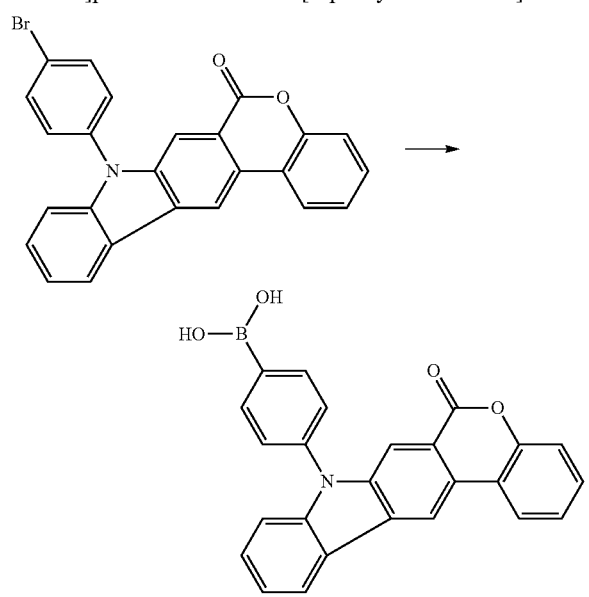

To a solution, cooled to −78° C., of 57 g (130 mmol) of 8-(4-bromophenyl)-8H-5-oxa-8-azaindeno[2,1-b]phenanthren-6-one in 1500 mL of THF are added dropwise 55 mL (138 mmol) of n-butyllithium (2.5 M in hexane). The reaction mixture is stirred at −78° C. for 30 min. The mixture is allowed to come to room temperature and cooled again to −78° C., and then a mixture of 20 mL (176 mmol) of trimethyl borate in 50 mL of THF is added rapidly. After warming to −10° C., hydrolysis is effected with 135 mL of 2 N hydrochloric acid. The organic phase is removed, washed with water, dried over sodium sulfate and concentrated to dryness. The residue is taken up in 300 mL of n-heptane, and the colorless solid is filtered off with suction, washed with n-heptane and dried under reduced pressure. Yield: 49 g (122 mmol), 95% of theory In an analogous manner, it is possible to prepare the following compounds:

| Reactant 1 | Product | Yield |
|---|---|---|
| | | 71% |
| | | 63% |

Example 7: Synthesis of 8-[4-(4,6-diphenyl-[1,3,5]triazin-2-yl)phenyl]-8H-5-oxa-8-azaindeno[2,1-b]phenanthren-6-one

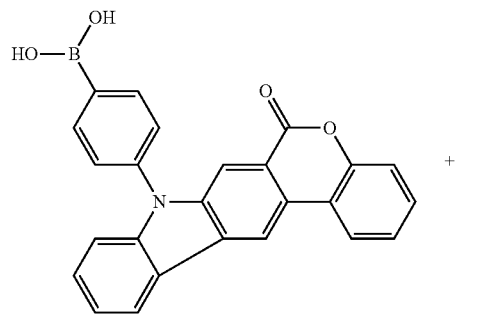

+

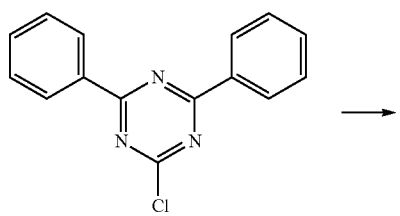

→

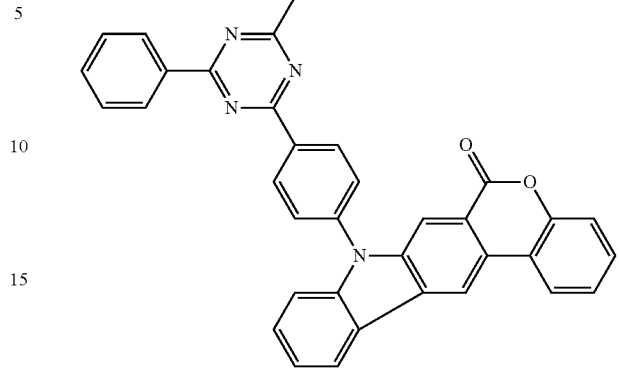

44 g (110 mmol) of 8H-5-oxa-8-azaindeno[2,1-b]phenanthren-6-one-8-[4-phenylboronic acid], 29.5 g (110.0 mmol) of 2-chloro-4,6-diphenyl-1,3,5-triazine and 44.6 g (210.0 mmol) of tripotassium phosphate are suspended in 500 mL of toluene, 500 mL of dioxane and 500 mL of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 mL of water and then concentrated to dryness. The residue is recrystallized from toluene/heptane and finally sublimed under high vacuum ($p=5\times10^{-5}$ mbar, T=377° C.). The yield is 44 g (75 mmol), corresponding to 69% of theory.

In an analogous manner, it is possible to prepare the following compounds:

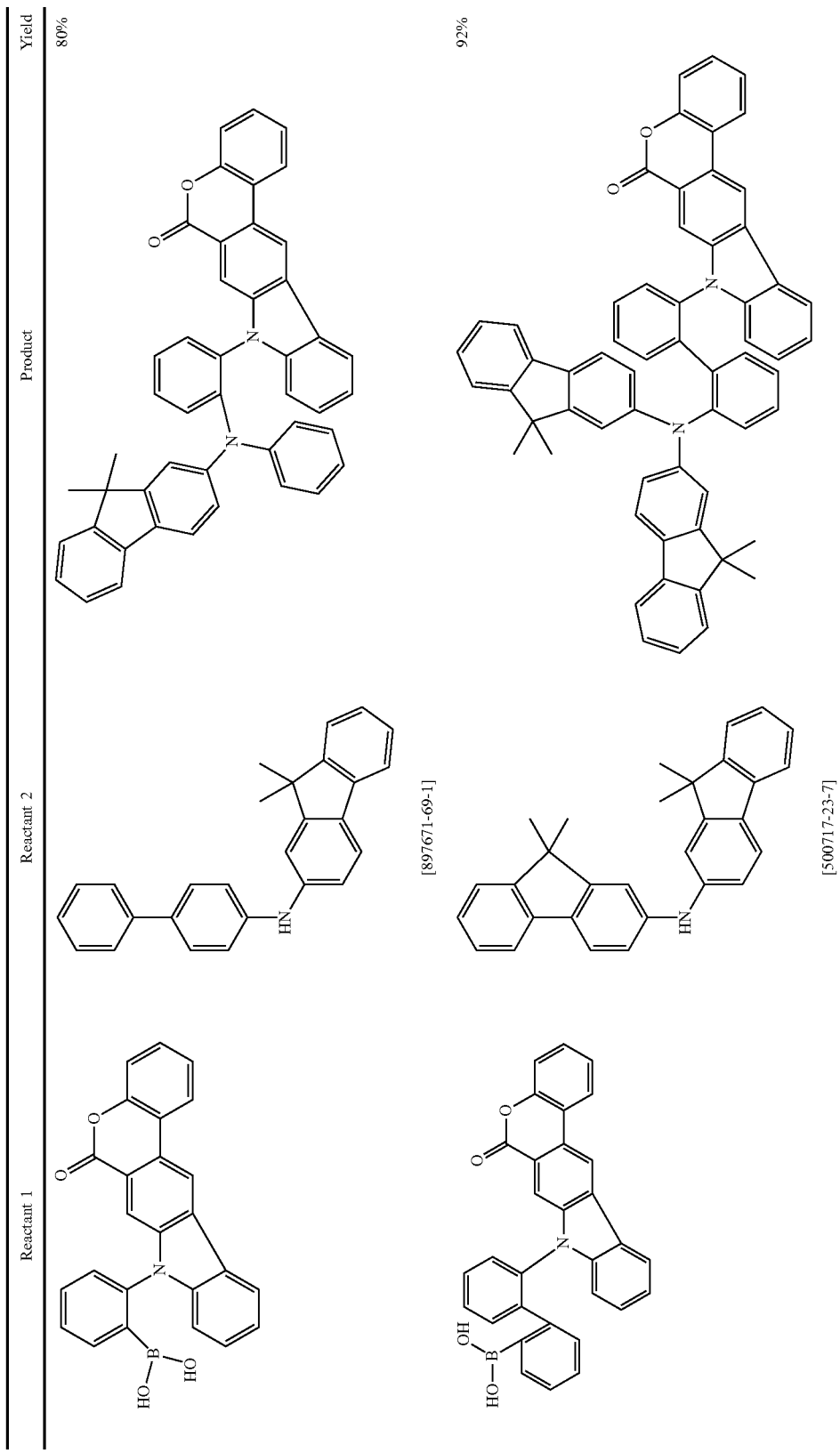

| Reactant 1 | Reactant 2 | Product | Yield |
|---|---|---|---|
| (structure with boronic acid) | (structure with Br) [1246562-40-2] | (coupled product) | 79% |

Example 8: Synthesis of 11-bromo-8-phenyl-8H-5-oxa-8-azaindeno[2,1-b]phenanthren-6-one

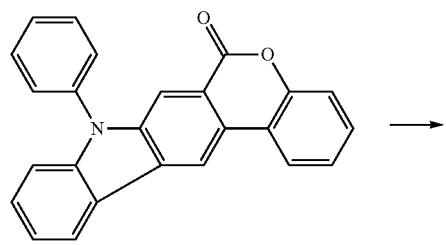

→

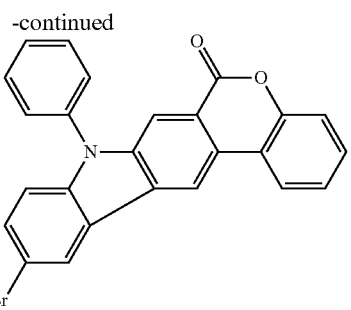

14.4 g (40.18 mmol) of 8H-5-oxa-8-azaindeno[2,1-b]phenanthren-6-one are suspended in 800 mL of acetonitrile and, at −20° C., 7.15 g (40.18 mmol) of N-bromosuccinimide are added in portions, in such a way that the reaction temperature does not rise above −20° C. The mixture is stirred for a further 18 h, in the course of which the temperature is allowed to come to room temperature. The reaction mixture is then concentrated by rotary evaporation, dissolved in dichloromethane and washed with water. The product is dried, concentrated and then recrystallized from toluene up to a purity of 99.0%. 13.9 g (79%) of the product are obtained as a white solid.

In an analogous manner, it is possible to prepare the following compounds:

| Reactant 1 | Product | Yield |
|---|---|---|
|  |  | 76% |
|  |  | 79% |

| Reactant 1 | Product | Yield |
|---|---|---|
| 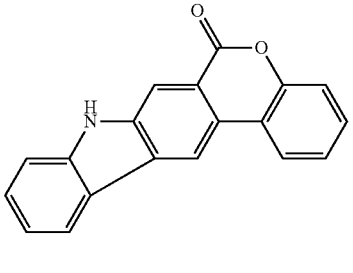 [SMILES: O=c1oc2ccccc2c2cc3c(cc12)[nH]c1ccccc13] | 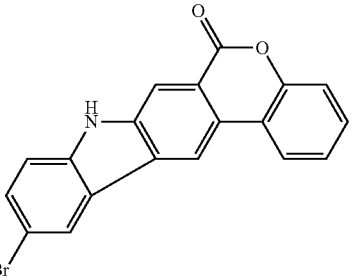 | 83% |

Example 9: Synthesis of 8-phenyl-11-(9-phenyl-9H-carbazol-3-yl)-8H-5-oxa-8-azaindeno[2,1-b]phenanthren-6-one

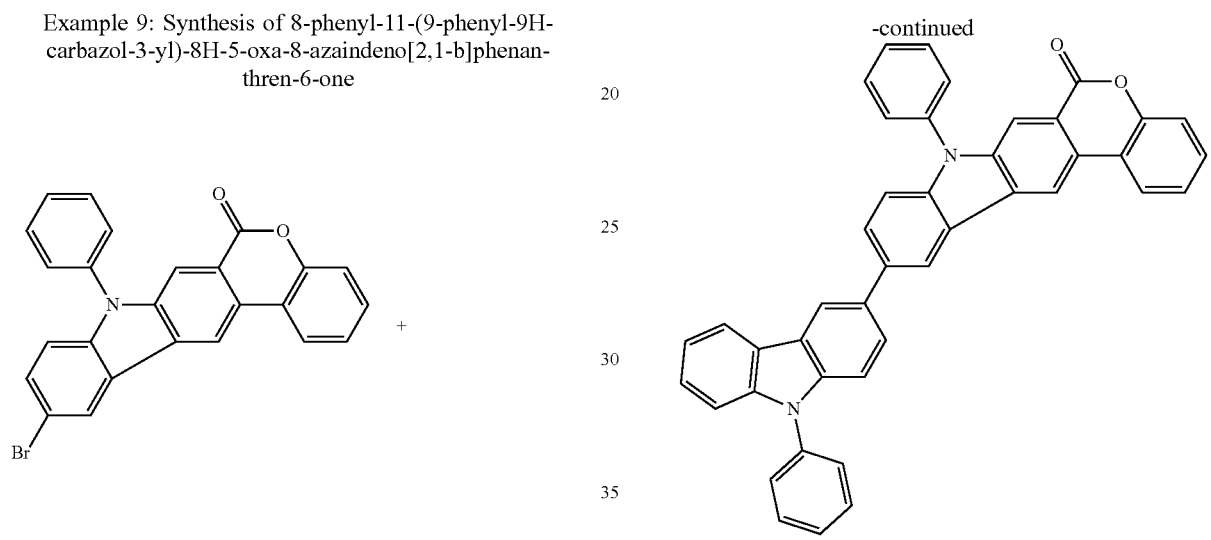

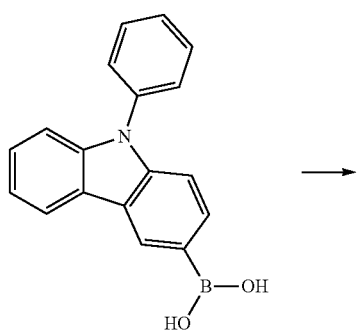

19 g (43.3 mmol) of 11-bromo-8-phenyl-8H-5-oxa-8-azaindeno[2,1-b]phenanthren-6-one and 13.7 g (48 mmol) of 9-phenyl-9H-carbazole-3-boronic acid are dissolved in 80 mL of toluene and degassed. 281 mL of degassed 2M $K_2CO_3$ and 2.5 g (2.2 mmol) of $Pd(OAc)_2$ are added. The reaction mixture is then stirred under a protective gas atmosphere at 80° C. for 48 h. The cooled solution is supplemented with toluene, washed repeatedly with water, dried and concentrated. The product is purified via column chromatography on silica gel with toluene/heptane (1:2) and finally sublimed under high vacuum (p=$5\times10^{-7}$ mbar). The purity is 99.9%. Yield: 21 g (35 mmol), 81% of theory In an analogous manner, it is possible to prepare the following compounds:

| Reactant 1 | Reactant 2 | Product | Yield |
|---|---|---|---|
| | 1001911-63-2 | | 83% |
| | 1338488-91-7 | | 89% |

-continued

| Reactant 1 | Reactant 2 | Product | Yield |
|---|---|---|---|
| | 918137-86-7 | | 83% |
| | | | 82% |

| Reactant 1 | Reactant 2 | Product | Yield |
|---|---|---|---|
| 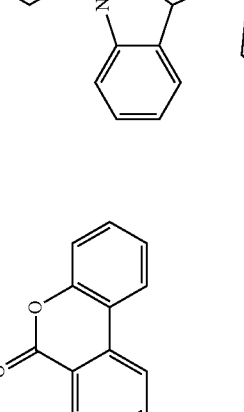 |  | 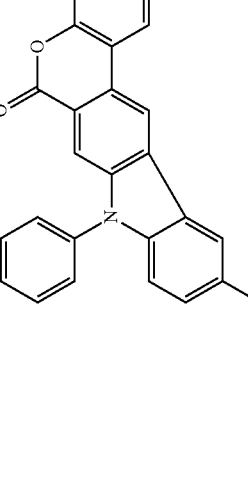 | 76% |

| Reactant 1 | Reactant 2 | Product | Yield |
|---|---|---|---|
| (bromo-pyrido-lactone-carbazole intermediate) | (dimethylfluorenyl-biphenyl-aminophenyl boronic acid) [1265177-27-2] | (coupled product) | 83% |
| (bromo-pyrido-lactone-carbazole intermediate) | (3-(4,6-diphenyl-1,3,5-triazin-2-yl)phenyl boronic acid) [1269508-31-7] | (coupled product) | 77% |

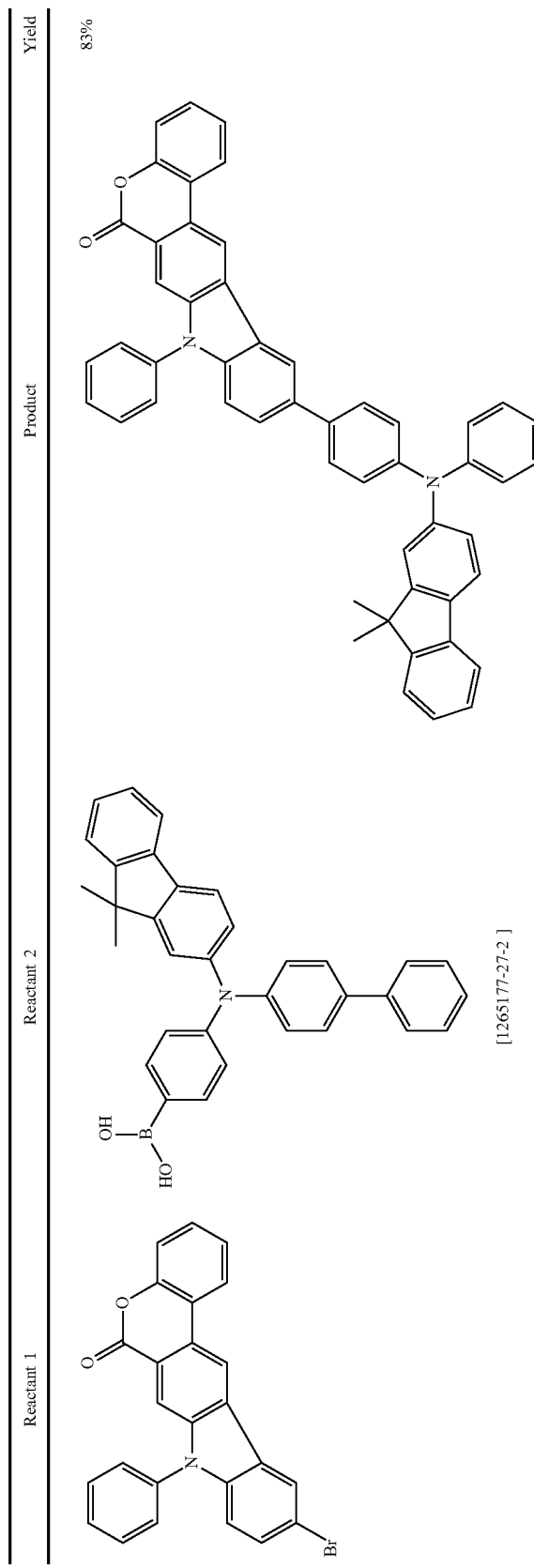

-continued

| Reactant 1 | Reactant 2 | Product | Yield |
|---|---|---|---|
| (structure) | (structure) [1153-85-1] | (structure) | 87% |

Example 10: 8,11-Bis-(9-phenyl-9H-carbazol-3-yl)-
8H-5-oxa-8-azaindeno[2,1-b]phenanthren-6-one

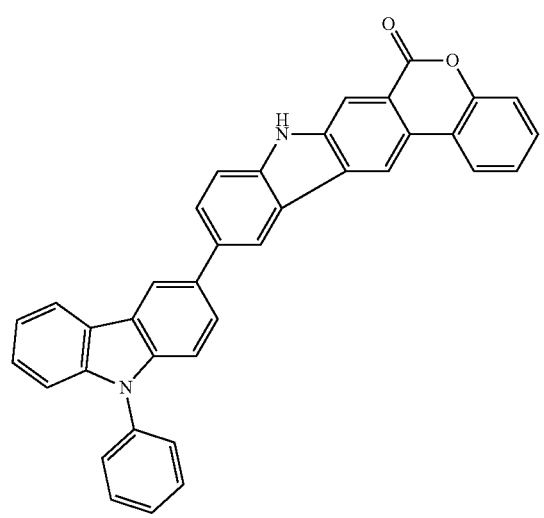

+

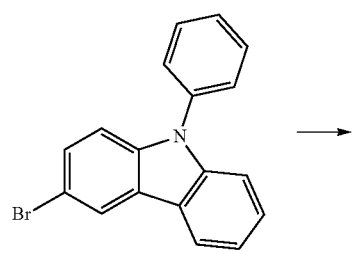

→

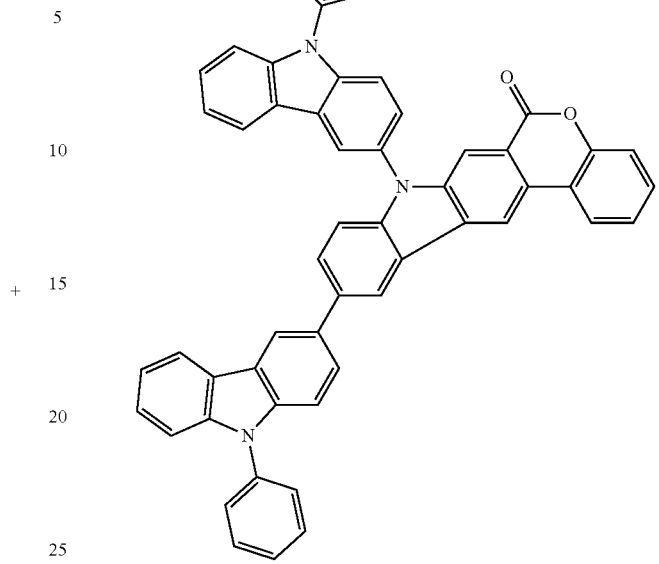

54 g (106 mmol) of 11-(9-phenyl-9H-carbazol-3-yl)-8H-5-oxa-8-azaindeno[2,1-b]phenanthren-6-one, 36.7 g (114 mmol) of bromobenzene and 30.5 g of NaOtBu are suspended in 1.5 L of p-xylene. To this suspension are added 0.5 g (2.11 mmol) of Pd(OAc)$_2$ and 6 mL of a 1M tri-tert-butylphosphine (1 M solution in toluene). The reaction mixture is heated under reflux for 16 h. After cooling, the organic phase is removed, washed three times with 200 mL each time of water and then concentrated to dryness. The residue is hot-extracted with toluene, recrystallized from toluene and finally sublimed under high vacuum; purity is 99.9% at a yield of 44 g (57 mmol; 55%).

In an analogous manner, it is possible to prepare the following compounds:

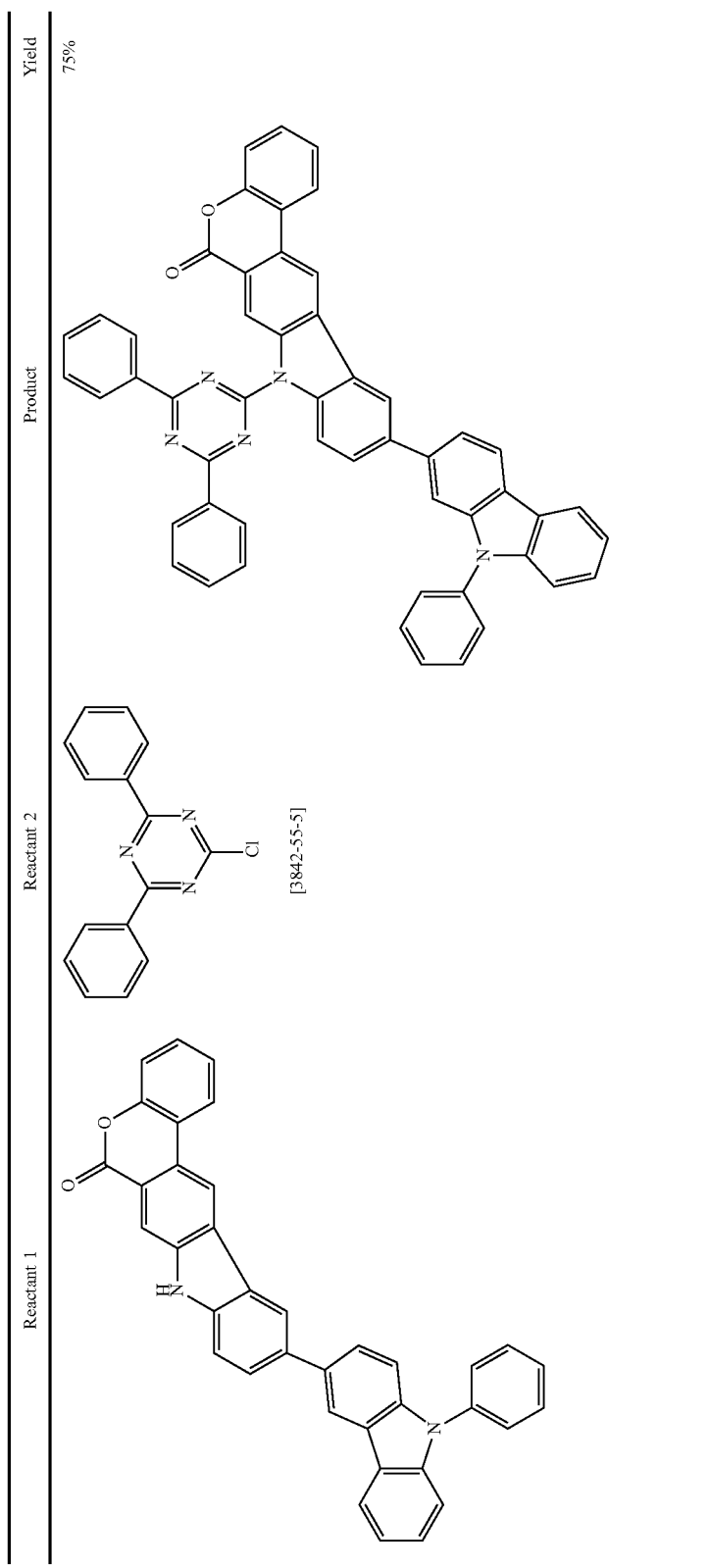

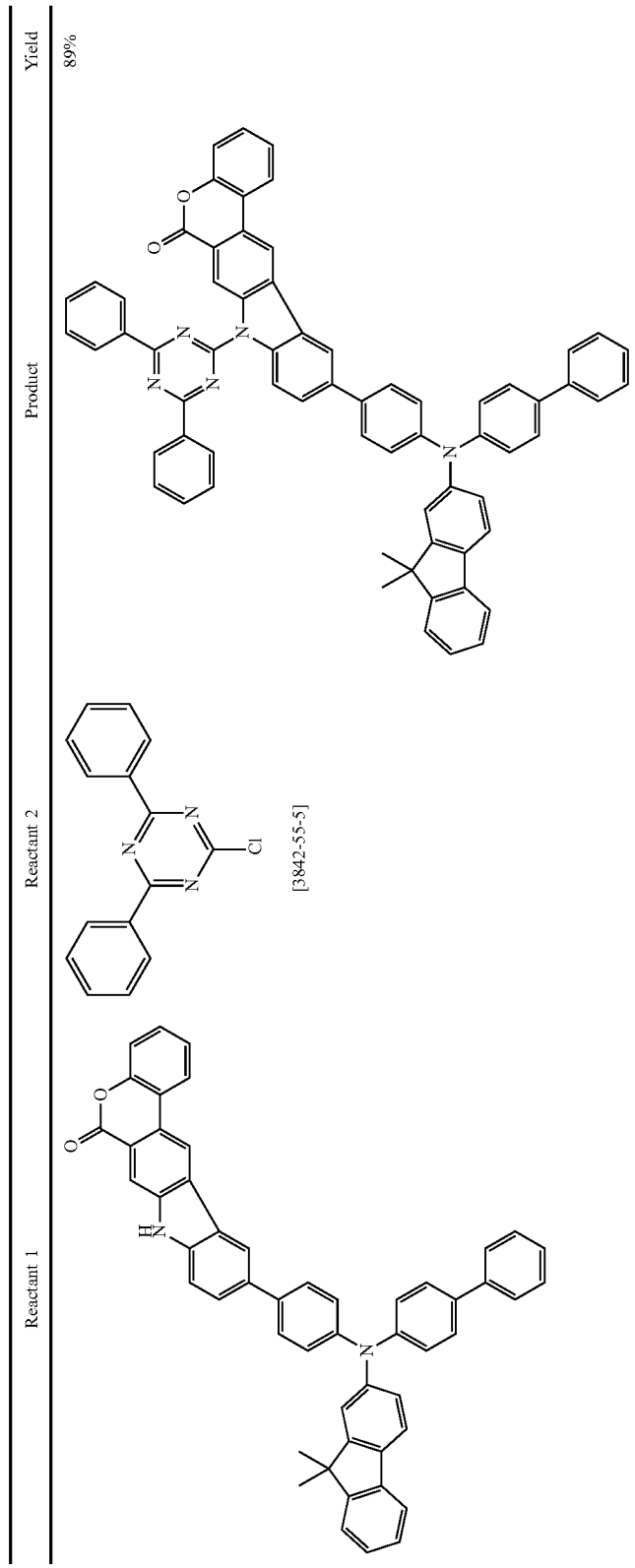

| Reactant 1 | Reactant 2 | Product | Yield |
|---|---|---|---|
| (structure) | (structure) [1153-85-1] | (structure) | 66% |

Production of the OLEDs

In examples I1 to I38 which follow (see Tables 1 and 2), the data of various OLEDs are presented. Cleaned glass plates (cleaning in laboratory washer, Merck Extran detergent) coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP Al 4083 from Heraeus Precious Metals GmbH Deutschland, spun on from aqueous solution) and baked at 180° C. for 10 min. These coated glass plates form the substrates to which the OLEDs are applied.

The OLEDs basically have the following layer structure: substrate/hole transport layer (HTL)/interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1. The materials required for production of the OLEDs are shown in Table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IP1:IC2:TEG2 (59%:29%:12%) mean here that the material IP1 is present in the layer in a proportion by volume of 59%, IC2 in a proportion of 29% and TEG2 in a proportion of 12%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are determined as a function of luminance, calculated from current-voltage-luminance characteristics (IUL characteristics) assuming Lambertian radiation characteristics. The electroluminescence spectra are determined at a luminance of 1000 cd/m², and the CIE 1931 x and y color coordinates are calculated therefrom. The parameter U1000 in Table 2 refers to the voltage which is required for a luminance of 1000 cd/m². CE1000 and PE1000 respectively refer to the current and power efficiencies which are achieved at 1000 cd/m². Finally, EQE1000 refers to the external quantum efficiency at an operating luminance of 1000 cd/m². The data for the various OLEDs are collated in Table 2. It is observed that excellent performance data can be achieved with the materials of the invention when they are used as matrix material for phosphorescent emitters, and when they are used as electron transport material.

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| I1 | HATCN 5 nm | SpMA1 50 nm | SpMA2 10 nm | IP1:TEG2 (83%:17%) 30 nm | ST2 10 nm | ST2:LiQ (50%:50%) 30 nm | — |
| I2 | HATCN 5 nm | SpMA1 50 nm | SpMA2 10 nm | IP1:IC2:TEG2 (59%:29%:12%) 30 nm | ST2 10 nm | ST2:LiQ (50%:50%) 30 nm | — |
| I3 | HATCN 5 nm | SpMA1 50 nm | SpMA2 10 nm | IP1:IC1:TEG2 (44%:44%:12%) 30 nm | ST2 10 nm | ST2:LiQ (50%:50%) 30 nm | — |
| I4 | HATCN 5 nm | SpMA1 50 nm | SpMA2 10 nm | IP2:TEG2 (83%:17%) 30 nm | — | ST2:LiQ (50%:50%) 40 nm | — |
| I5 | HATCN 5 nm | SpMA1 50 nm | SpMA2 10 nm | IP3:TEG2 (83%:17%) 30 nm | ST2 10 nm | ST2:LiQ (50%:50%) 30 nm | — |
| I6 | HATCN 5 nm | SpMA1 50 nm | SpMA2 10 nm | IP4:TEG2 (83%:17%) 30 nm | ST2 10 nm | ST2:LiQ (50%:50%) 30 nm | — |
| I7 | HATCN 5 nm | SpMA1 50 nm | SpMA2 10 nm | IP5:IC1:TEG2 (44%:44%:12%) 30 nm | ST2 10 nm | ST2:LiQ (50%:50%) 30 nm | — |
| I8 | HATCN 5 nm | SpMA1 50 nm | SpMA2 10 nm | IP6:TEG2 (83%:17%) 30 nm | ST2 10 nm | ST2:LiQ (50%:50%) 30 nm | — |
| I9 | HATCN 5 nm | SpMA1 50 nm | SpMA2 10 nm | IP7:TEG2 (83%:17%) 30 nm | ST2 10 nm | ST2:LiQ (50%:50%) 30 nm | — |
| I10 | HATCN 5 nm | SpMA1 50 nm | SpMA2 10 nm | IP8:TEG2 (83%:17%) 30 nm | ST2 10 nm | ST2:LiQ (50%:50%) 30 nm | — |
| I11 | HATCN 5 nm | SpMA1 50 nm | SpMA2 10 nm | IP9:TEG2 (83%:17%) 30 nm | ST2 10 nm | ST2:LiQ (50%:50%) 30 nm | — |
| I12 | HATCN 5 nm | SpMA1 50 nm | SpMA2 10 nm | IP10:TEG2 (83%:17%) 30 nm | ST2 10 nm | ST2:LiQ (50%:50%) 30 nm | — |
| I13 | HATCN 5 nm | SpMA1 50 nm | SpMA2 10 nm | IC1:TEG2 (83%:17%) 30 nm | — | IP11 40 nm | LiQ 3 nm |
| I14 | HATCN 5 nm | SpMA1 50 nm | SpMA2 10 nm | IP12:IC1:TEG2 (44%:44%:12%) 30 nm | ST2 10 nm | ST2:LiQ (50%:50%) 30 nm | — |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| I15 | HATCN 5 nm | SpMA1 50 nm | SpMA2 10 nm | IP13:L1:TEG2 (44%:44%:12%) 30 nm | ST2 10 nm | ST2:LiQ (50%:50%) 30 nm | — |
| I16 | HATCN 5 nm | SpMA1 50 nm | SpMA2 10 nm | IP14:TEG2 (83%:17%) 30 nm | ST2 10 nm | ST2:LiQ (50%:50%) 30 nm | — |
| I17 | HATCN 5 nm | SpMA1 50 nm | SpMA2 10 nm | IP15:TEG2 (83%:17%) 30 nm | ST2 10 nm | ST2:LiQ (50%:50%) 30 nm | — |
| I18 | HATCN 5 nm | SpMA1 50 nm | SpMA2 10 nm | IP16:IC1:TEG2 (44%:44%:12%) 30 nm | ST2 10 nm | ST2:LiQ (50%:50%) 30 nm | — |
| I19 | HATCN 5 nm | SpMA1 50 nm | SpMA2 10 nm | IP17:TEG2 (83%:17%) 30 nm | ST2 10 nm | ST2:LiQ (50%:50%) 30 nm | — |
| I20 | HATCN 5 nm | SpMA1 50 nm | SpMA2 10 nm | IC1:TEG2 (83%:17%) 30 nm | — | IP18 40 nm | LiQ 3 nm |
| I21 | HATCN 5 nm | SpMA1 50 nm | SpMA2 10 nm | IP18:L1:TEG2 (44%:44%:12%) 30 nm | ST2 10 nm | ST2:LiQ (50%:50%) 30 nm | — |
| I22 | SpA1 90 nm | HATCN 5 nm | SpMA1 130 nm | IP19:TER3 (92%:8%) 40 nm | — | ST2:LiQ (50%:50%) 40 nm | — |
| I23 | HATCN 5 nm | SpMA1 50 nm | SpMA2 10 nm | IP20:TEG1 (83%:17%) 30 nm | ST2 10 nm | ST2:LiQ (50%:50%) 30 nm | — |
| I24 | HATCN 5 nm | SpMA1 50 nm | SpMA2 10 nm | IP21:TEG2 (83%:17%) 30 nm | ST2 10 nm | ST2:LiQ (50%:50%) 30 nm | — |
| I25 | HATCN 5 nm | SpMA1 50 nm | SpMA2 10 nm | IP22:TEG2 (83%:17%) 30 nm | ST2 10 nm | ST2:LiQ (50%:50%) 30 nm | — |
| I26 | HATCN 5 nm | SpMA1 50 nm | SpMA2 10 nm | IP23:L1:TEG2 (44%:44%:12%) 30 nm | ST2 10 nm | ST2:LiQ (50%:50%) 30 nm | — |
| I27 | SpA1 90 nm | HATCN 5 nm | SpMA1 130 nm | IC1:IP24:TER3 (40%:50%:10%) 40 nm | IC2 5 nm | ST2:LiQ (50%:50%) 35 nm | — |
| I28 | HATCN 5 nm | SpMA1 50 nm | SpMA2 10 nm | IP25:IC2:TEG2 (60%:25%:15%) 30 nm | ST2 10 nm | ST2:LiQ (50%:50%) 30 nm | — |
| I29 | HATCN 5 nm | SpMA1 50 nm | SpMA2 10 nm | IP26:TEG2 (83%:17%) 30 nm | ST2 10 nm | ST2:LiQ (50%:50%) 30 nm | — |
| I30 | HATCN 5 nm | SpMA1 50 nm | SpMA2 10 nm | IP27:IC1:TEG2 (50%:35%:15%) 30 nm | ST2 10 nm | ST2:LiQ (50%:50%) 30 nm | — |
| I31 | HATCN 5 nm | SpMA1 50 nm | SpMA2 10 nm | IP28:IC1:TEG2 (50%:35%:15%) 30 nm | ST2 10 nm | ST2:LiQ (50%:50%) 30 nm | — |
| I32 | HATCN 5 nm | SpMA1 50 nm | SpMA2 10 nm | IP29:IC1:TEG2 (44%:44%:12%) 30 nm | ST2 10 nm | ST2:LiQ (50%:50%) 30 nm | — |
| I33 | HATCN 5 nm | SpMA1 50 nm | SpMA2 10 nm | IP30:L2:TEG2 (44%:44%:12%) 30 nm | ST2 10 nm | ST2:LiQ (50%:50%) 30 nm | — |
| I34 | HATCN 5 nm | SpMA1 50 nm | SpMA2 10 nm | IP31:IC1:TEG2 (58%:30%:12%) 30 nm | ST2 10 nm | ST2:LiQ (50%:50%) 30 nm | — |
| I35 | HATCN 5 nm | SpMA1 50 nm | SpMA2 10 nm | IP32:TEG2 (83%:17%) 30 nm | ST2 10 nm | ST2:LiQ (50%:50%) 30 nm | — |
| I36 | HATCN 5 nm | SpMA1 50 nm | SpMA2 10 nm | IP33:IC1:TEG2 (50%:35%:15%) 30 nm | ST2 10 nm | ST2:LiQ (50%:50%) 30 nm | — |
| I37 | HATCN 5 nm | SpMA1 50 nm | SpMA2 10 nm | IP34:IC1:TEG2 (44%:44%:12%) 30 nm | ST2 10 nm | ST2:LiQ (50%:50%) 30 nm | — |
| I38 | HATCN 5 nm | SpMA1 50 nm | SpMA2 10 nm | IP35:TEG2 (83%:17%) 30 nm | ST2 10 nm | ST2:LiQ (50%:50%) 30 nm | — |

TABLE 2
Data of the OLEDs
| Ex. | U1000 (V) | CE1000 (cd/A) | PE1000 (lm/W) | EQE 1000 | CIE x/y at 1000 cd/m² |
|---|---|---|---|---|---|
| I1 | 3.5 | 75 | 68 | 20.5% | 0.35/0.62 |
| I2 | 3.6 | 68 | 60 | 18.1% | 0.34/0.63 |
| I3 | 3.2 | 70 | 69 | 18.8% | 0.34/0.62 |
| I4 | 3.2 | 68 | 68 | 18.5% | 0.34/0.62 |
| I5 | 3.4 | 70 | 63 | 18.7% | 0.35/0.62 |
| I6 | 3.8 | 57 | 47 | 15.4% | 0.34/0.62 |
| I7 | 3.1 | 65 | 65 | 17.6% | 0.35/0.61 |
| I8 | 3.4 | 61 | 58 | 16.6% | 0.33/0.63 |
| I9 | 3.6 | 76 | 66 | 20.7% | 0.35/0.62 |
| I10 | 3.8 | 71 | 58 | 19.1% | 0.34/0.62 |
| I11 | 3.1 | 56 | 57 | 15.2% | 0.35/0.62 |
| I12 | 3.2 | 72 | 71 | 19.8% | 0.35/0.62 |
| I13 | 4.4 | 65 | 47 | 17.7% | 0.35/0.62 |
| I14 | 3.4 | 63 | 59 | 17.0% | 0.35/0.62 |
| I15 | 3.5 | 56 | 51 | 15.2% | 0.34/0.62 |
| I16 | 3.0 | 67 | 70 | 18.0% | 0.34/0.62 |
| I17 | 3.4 | 68 | 64 | 18.4% | 0.34/0.62 |
| I18 | 3.3 | 64 | 62 | 17.3% | 0.35/0.62 |
| I19 | 3.6 | 58 | 51 | 15.8% | 0.35/0.62 |
| I20 | 3.5 | 68 | 61 | 18.3% | 0.33/0.63 |
| I21 | 3.1 | 62 | 63 | 16.7% | 0.34/0.62 |
| I22 | 4.3 | 10.3 | 7.5 | 11.1% | 0.67/0.33 |
| I23 | 3.5 | 69 | 63 | 18.8% | 0.36/0.61 |
| I24 | 3.5 | 69 | 62 | 18.5% | 0.33/0.62 |
| I25 | 3.4 | 52 | 48 | 14.3% | 0.35/0.61 |
| I26 | 3.1 | 64 | 65 | 17.4% | 0.35/0.62 |
| I27 | 4.3 | 11.7 | 8.6 | 12.7% | 0.67/0.33 |
| I28 | 3.0 | 75 | 78 | 20.2% | 0.35/0.62 |
| I29 | 3.6 | 63 | 55 | 16.9% | 0.34/0.62 |
| I30 | 3.3 | 70 | 67 | 19.0% | 0.34/0.62 |
| I31 | 3.2 | 73 | 73 | 19.8% | 0.33/0.63 |
| I32 | 3.2 | 72 | 70 | 19.4% | 0.34/0.62 |
| I33 | 3.5 | 65 | 60 | 17.8% | 0.35/0.61 |
| I34 | 3.7 | 60 | 51 | 16.3% | 0.36/0.61 |
| I35 | 3.0 | 64 | 67 | 17.3% | 0.34/0.62 |
| I36 | 3.2 | 67 | 66 | 18.1% | 0.35/0.62 |
| I37 | 3.3 | 63 | 59 | 17.0% | 0.35/0.62 |
| I38 | 3.1 | 64 | 65 | 17.3% | 0.34/0.62 |
TABLE 3
Structural formulae of the materials for the OLEDs
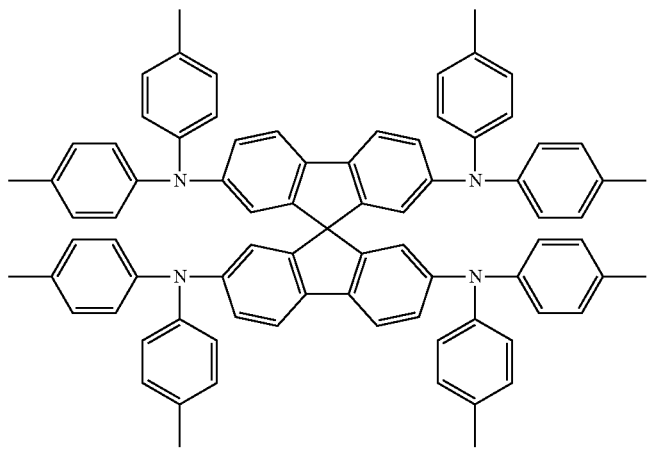
SpA1
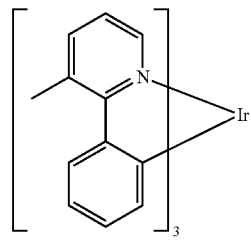
TEG1

TABLE 3-continued
Structural formulae of the materials for the OLEDs
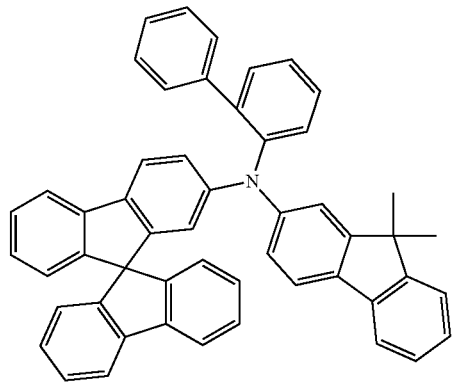 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
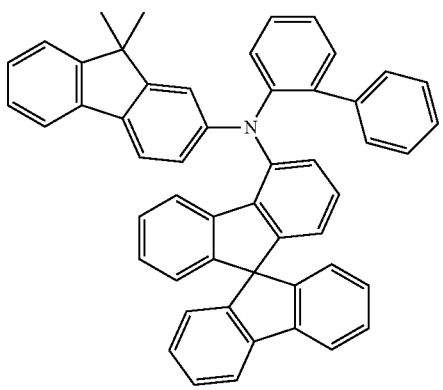 [SMILES: CC1(C)c2ccccc2-c2ccc(N(c3ccccc3-c3ccccc3)c3cccc4c3-c3ccccc3C43c4ccccc4-c4ccccc43)cc21]
SpMA2
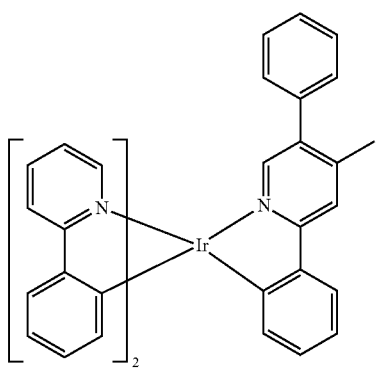
TEG2
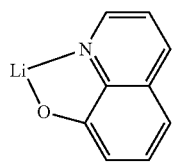
LiQ TABLE 3-continued
Structural formulae of the materials for the OLEDs
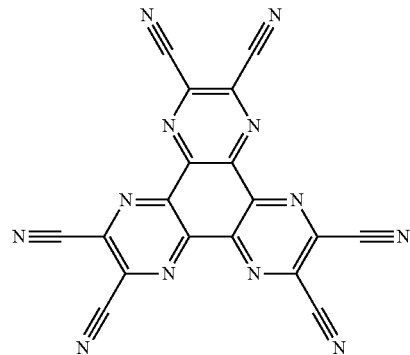 [SMILES: N#Cc1nc2c3nc(C#N)c(C#N)nc3c3nc(C#N)c(C#N)nc3c2nc1C#N]
HATCN
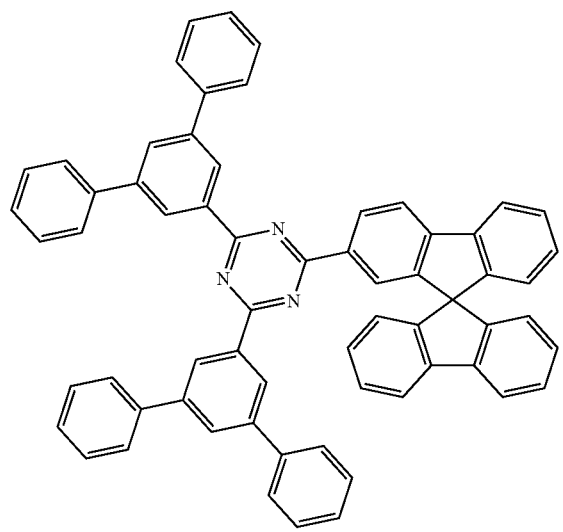 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
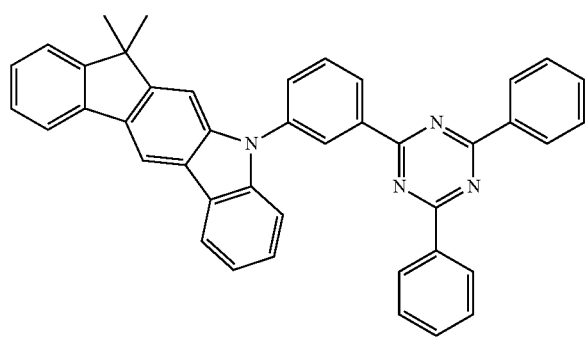 [SMILES: CC1(C)c2ccccc2-c2cc3c4ccccc4n(-c4cccc(-c5nc(-c6ccccc6)nc(-c6ccccc6)n5)c4)c3cc21]
IC1

TABLE 3-continued
Structural formulae of the materials for the OLEDs
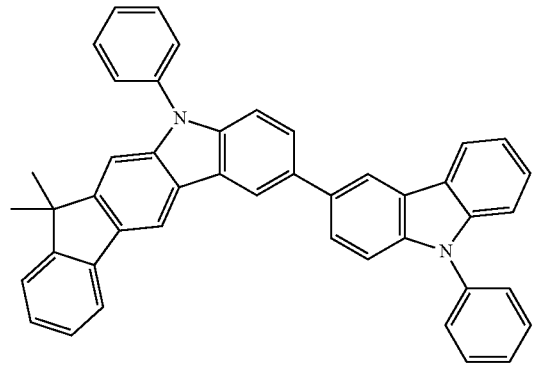 [SMILES: CC1(C)c2ccccc2-c2cc3c4cc(-c5ccc6c(c5)c5ccccc5n6-c5ccccc5)ccc4n(-c4ccccc4)c3cc21]
IC2
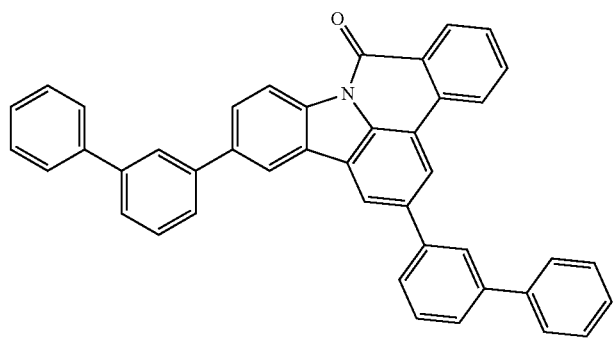 [SMILES: O=c1c2ccccc2c2cc(-c3cccc(-c4ccccc4)c3)cc3c4cc(-c5cccc(-c6ccccc6)c5)ccc4n1c23]
L1
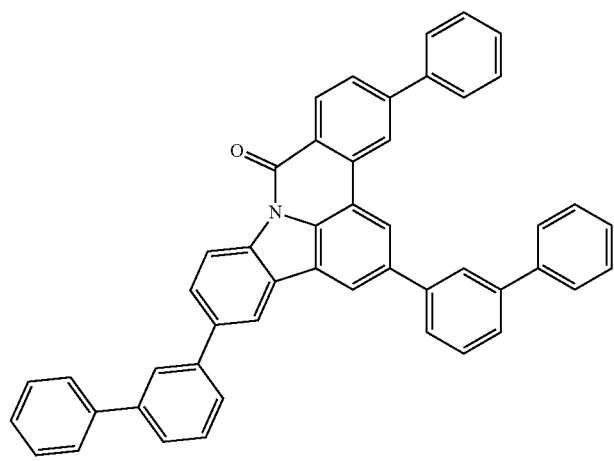 [SMILES: O=c1c2ccc(-c3ccccc3)cc2c2cc(-c3cccc(-c4ccccc4)c3)cc3c4cc(-c5cccc(-c6ccccc6)c5)ccc4n1c23]
L2

TABLE 3-continued
Structural formulae of the materials for the OLEDs
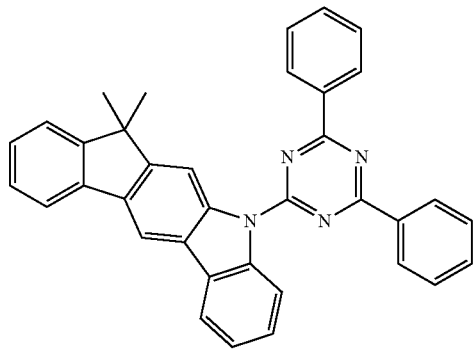 [SMILES: CC1(C)c2ccccc2-c2cc3c4ccccc4n(-c4nc(-c5ccccc5)nc(-c5ccccc5)n4)c3cc21]
IC3
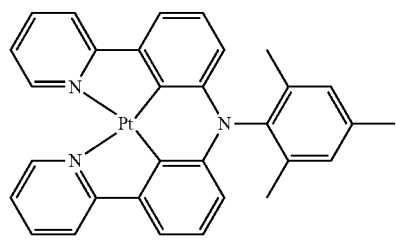
TER3
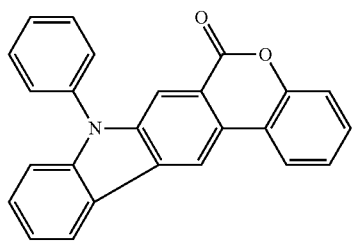 [SMILES: O=c1oc2ccccc2c2cc3c4ccccc4n(-c4ccccc4)c3cc12]
IP1
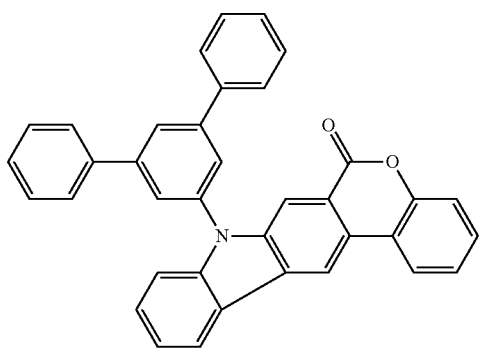 [SMILES: O=c1oc2ccccc2c2cc3c4ccccc4n(-c4cc(-c5ccccc5)cc(-c5ccccc5)c4)c3cc12]
IP2

TABLE 3-continued
Structural formulae of the materials for the OLEDs
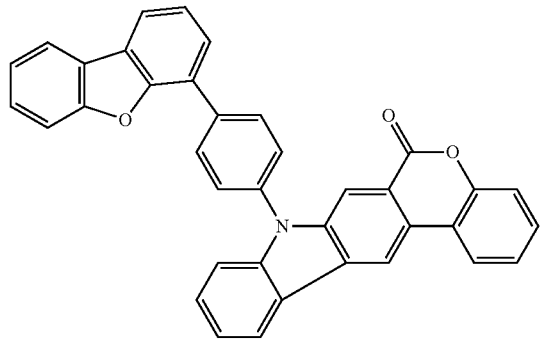 [SMILES: O=c1oc2ccccc2c2cc3c4ccccc4n(-c4ccc(-c5cccc6c5oc5ccccc56)cc4)c3cc12]
IP3
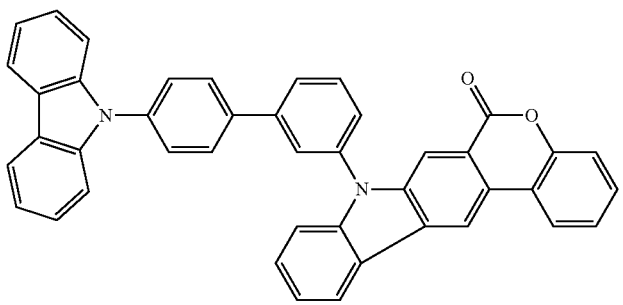
IP4
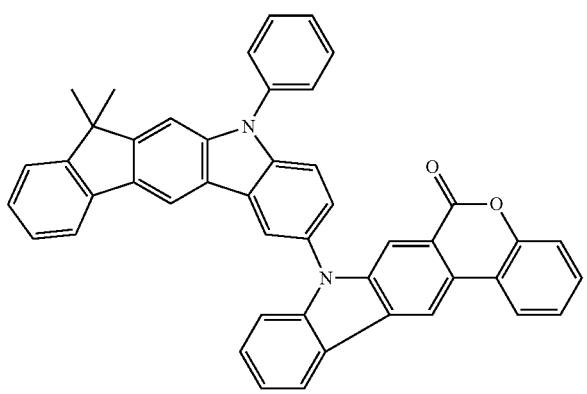 [SMILES: CC1(C)c2ccccc2-c2cc3c4cc(-n5c6ccccc6c6cc7c(cc65)c(=O)oc5ccccc57)ccc4n(-c4ccccc4)c3cc21]
IP5
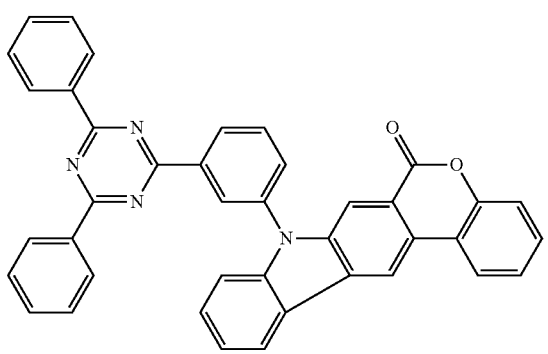 [SMILES: O=c1oc2ccccc2c2cc3c4ccccc4n(-c4cccc(-c5nc(-c6ccccc6)nc(-c6ccccc6)n5)c4)c3cc12]
IP6

TABLE 3-continued
Structural formulae of the materials for the OLEDs
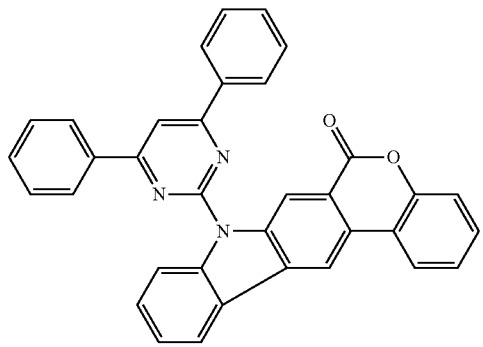 [SMILES: O=c1oc2ccccc2c2cc3c4ccccc4n(-c4nc(-c5ccccc5)cc(-c5ccccc5)n4)c3cc12]
IP7
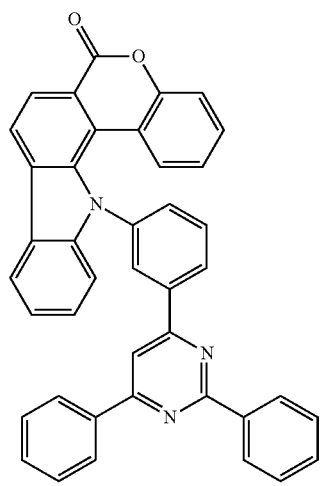 [SMILES: O=c1oc2ccccc2c2c1ccc1c3ccccc3n(-c3cccc(-c4cc(-c5ccccc5)nc(-c5ccccc5)n4)c3)c12]
IP8
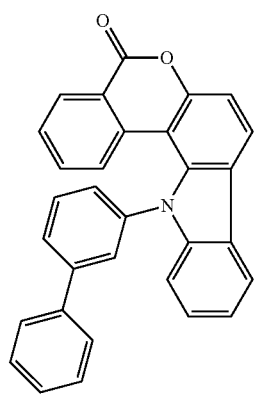 [SMILES: O=c1oc2ccc3c4ccccc4n(-c4cccc(-c5ccccc5)c4)c3c2c2ccccc12]
IP9

TABLE 3-continued
Structural formulae of the materials for the OLEDs
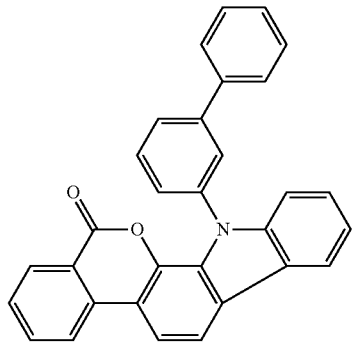 [SMILES: O=c1oc2c(ccc3c4ccccc4n(-c4cccc(-c5ccccc5)c4)c32)c2ccccc12]
IP10
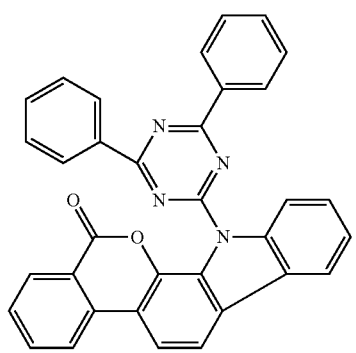 [SMILES: O=c1oc2c(ccc3c4ccccc4n(-c4nc(-c5ccccc5)nc(-c5ccccc5)n4)c32)c2ccccc12]
IP11
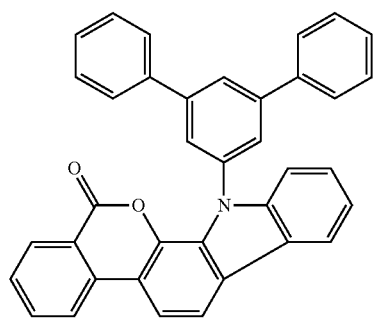 [SMILES: O=c1oc2c(ccc3c4ccccc4n(-c4cc(-c5ccccc5)cc(-c5ccccc5)c4)c32)c2ccccc12]
IP12

219
TABLE 3-continued
Structural formulae of the materials for the OLEDs
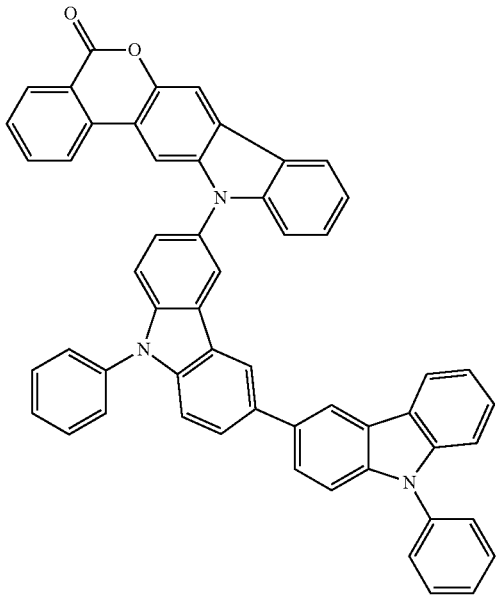 [SMILES: O=c1oc2cc3c4ccccc4n(-c4ccc5c(c4)c4cc(-c6ccc7c(c6)c6ccccc6n7-c6ccccc6)ccc4n5-c4ccccc4)c3cc2c2ccccc12]
IP13
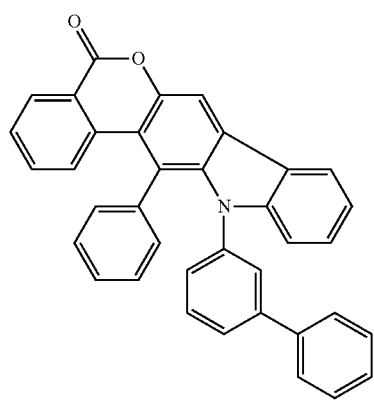 [SMILES: O=c1oc2cc3c4ccccc4n(-c4cccc(-c5ccccc5)c4)c3c(-c3ccccc3)c2c2ccccc12]
IP14
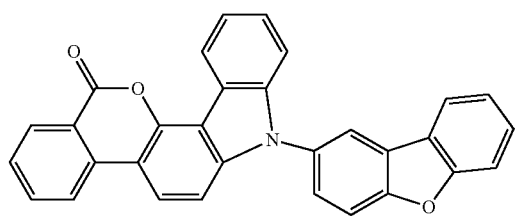 [SMILES: O=c1oc2c(ccc3c2c2ccccc2n3-c2ccc3oc4ccccc4c3c2)c2ccccc12]
IP15

TABLE 3-continued
Structural formulae of the materials for the OLEDs
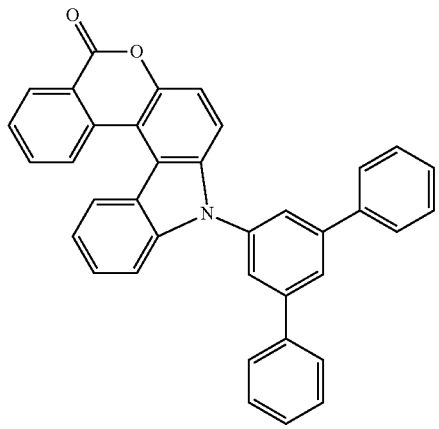 [SMILES: O=c1oc2ccc3c(c4ccccc4n3-c3cc(-c4ccccc4)cc(-c4ccccc4)c3)c2c2ccccc12]
IP16
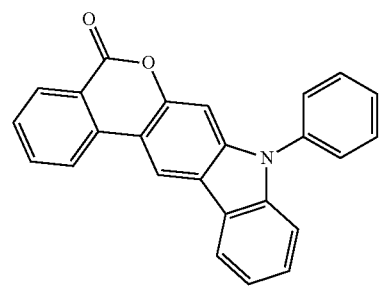 [SMILES: O=c1oc2cc3c(cc2c2ccccc12)c1ccccc1n3-c1ccccc1]
IP17
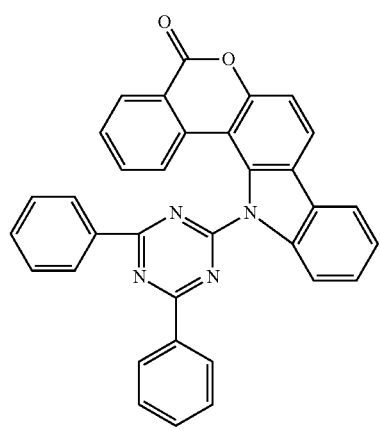 [SMILES: O=c1oc2ccc3c4ccccc4n(-c4nc(-c5ccccc5)nc(-c5ccccc5)n4)c3c2c2ccccc12]
IP18

TABLE 3-continued
Structural formulae of the materials for the OLEDs
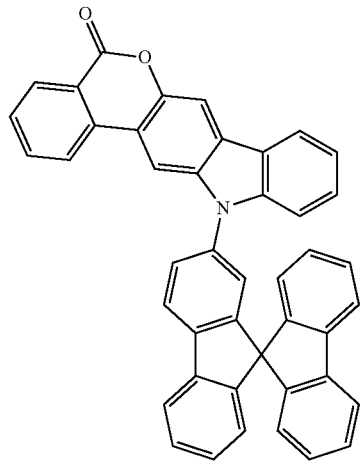 [SMILES: O=c1oc2cc3c4ccccc4n(-c4ccc5c(c4)C4(c6ccccc6-c6ccccc64)c4ccccc4-5)c3cc2c2ccccc12]
IP19
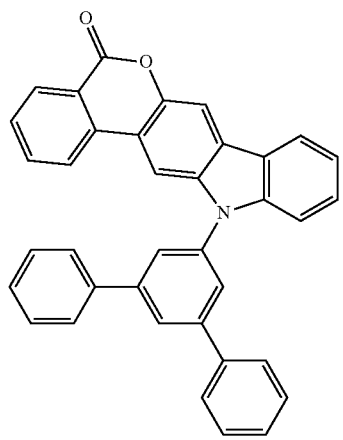 [SMILES: O=c1oc2cc3c4ccccc4n(-c4cc(-c5ccccc5)cc(-c5ccccc5)c4)c3cc2c2ccccc12]
IP20
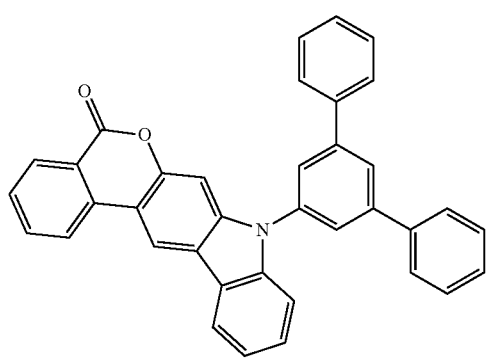 [SMILES: O=c1oc2cc3c(cc2c2ccccc12)c1ccccc1n3-c1cc(-c2ccccc2)cc(-c2ccccc2)c1]
IP21

TABLE 3-continued
Structural formulae of the materials for the OLEDs
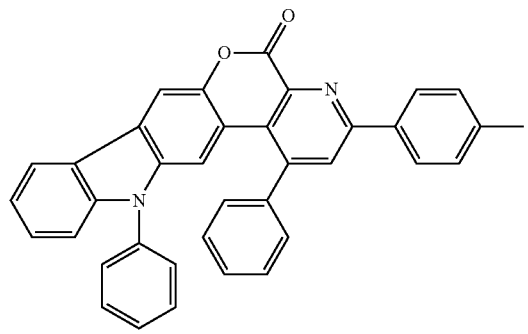 [SMILES: Cc1ccc(-c2cc(-c3ccccc3)c3c(n2)c(=O)oc2cc4c5ccccc5n(-c5ccccc5)c4cc23)cc1]
IP22
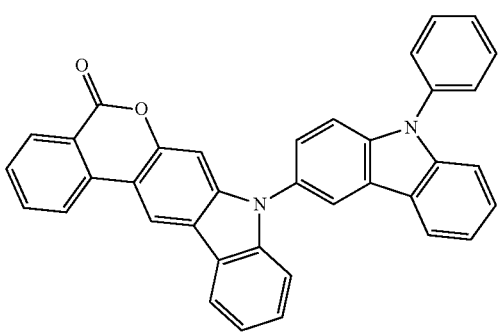 [SMILES: O=c1oc2cc3c(cc2c2ccccc12)c1ccccc1n3-c1ccc2c(c1)c1ccccc1n2-c1ccccc1]
IP23
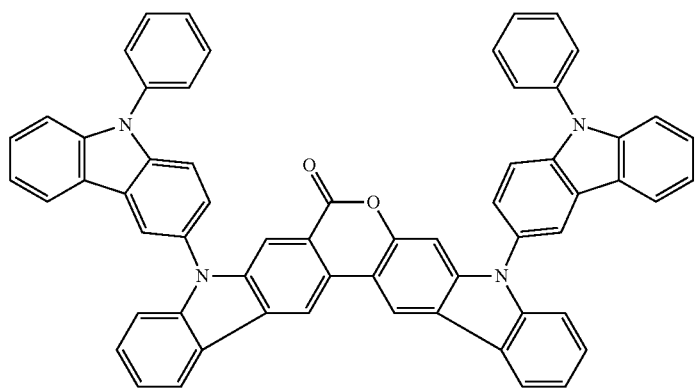 [SMILES: O=c1oc2cc3c(cc2c2cc4c5ccccc5n(-c5ccc6c(c5)c5ccccc5n6-c5ccccc5)c4cc12)c1ccccc1n3-c1ccc2c(c1)c1ccccc1n2-c1ccccc1]
IP24
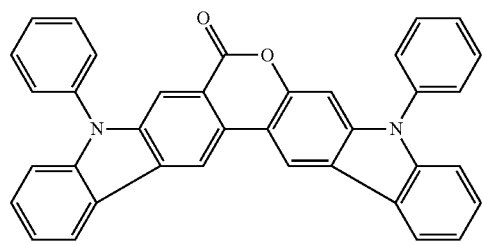 [SMILES: O=c1oc2cc3c(cc2c2cc4c5ccccc5n(-c5ccccc5)c4cc12)c1ccccc1n3-c1ccccc1]
IP25

TABLE 3-continued
Structural formulae of the materials for the OLEDs
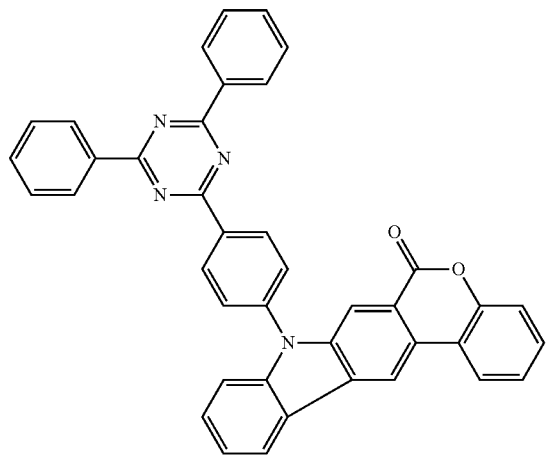 [SMILES: O=c1oc2ccccc2c2cc3c4ccccc4n(-c4ccc(-c5nc(-c6ccccc6)nc(-c6ccccc6)n5)cc4)c3cc12]
IP26
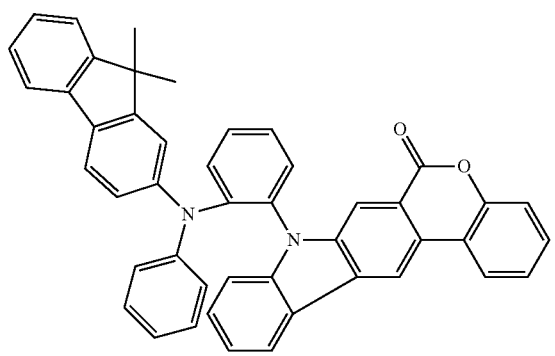 [SMILES: CC1(C)c2ccccc2-c2ccc(N(c3ccccc3)c3ccccc3-n3c4ccccc4c4cc5c(cc43)c(=O)oc3ccccc35)cc21]
IP27
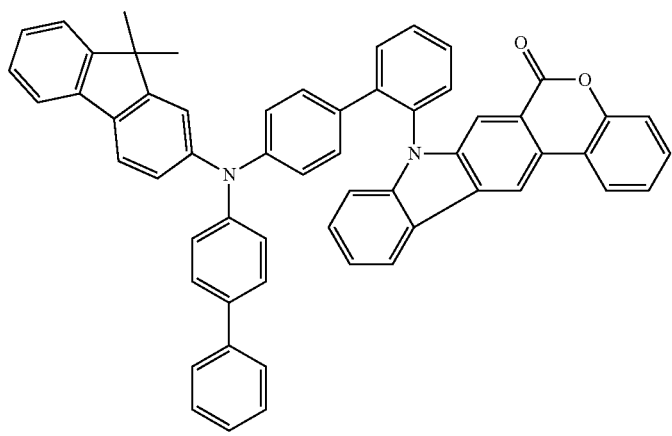 [SMILES: CC1(C)c2ccccc2-c2ccc(N(c3ccc(-c4ccccc4)cc3)c3ccc(-c4ccccc4-n4c5ccccc5c5cc6c(cc54)c(=O)oc4ccccc46)cc3)cc21]
IP28

TABLE 3-continued
Structural formulae of the materials for the OLEDs
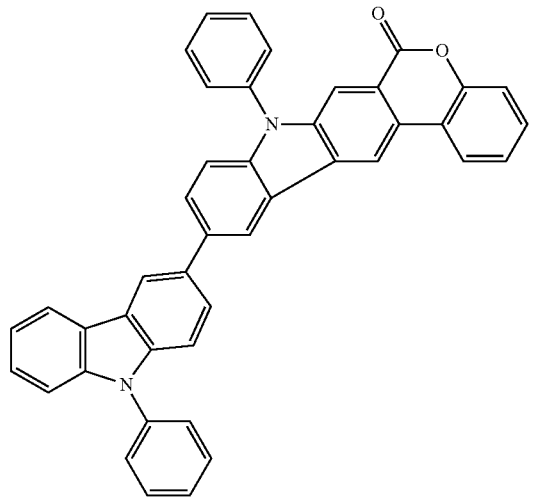 [SMILES: O=c1oc2ccccc2c2cc3c4cc(-c5ccc6c(c5)c5ccccc5n6-c5ccccc5)ccc4n(-c4ccccc4)c3cc12]
IP29
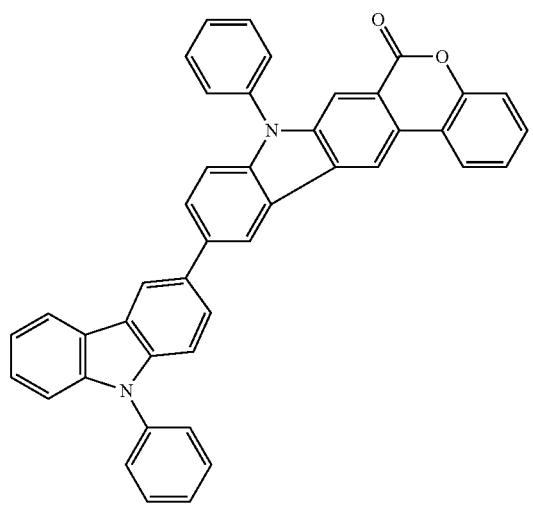 [SMILES: O=c1oc2ccccc2c2cc3c4cc(-c5ccc6c(c5)c5ccccc5n6-c5ccccc5)ccc4n(-c4ccccc4)c3cc12]
IP30
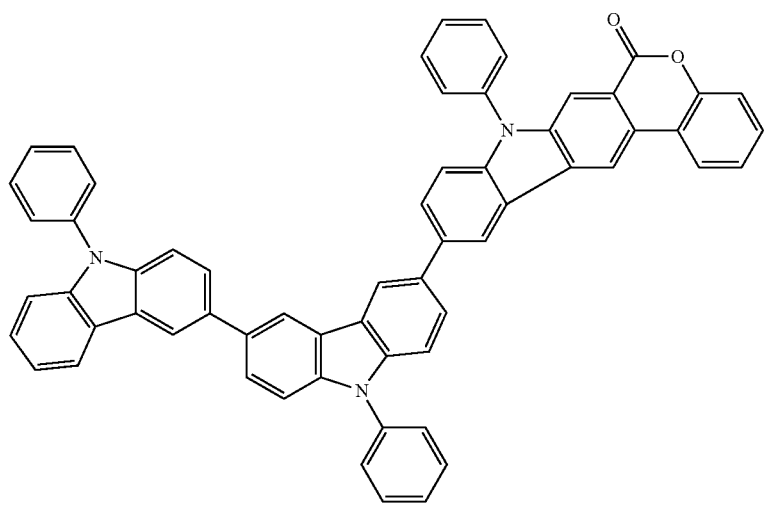 [SMILES: O=c1oc2ccccc2c2cc3c4cc(-c5ccc6c(c5)c5cc(-c7ccc8c(c7)c7ccccc7n8-c7ccccc7)ccc5n6-c5ccccc5)ccc4n(-c4ccccc4)c3cc12]
IP31

TABLE 3-continued
Structural formulae of the materials for the OLEDs
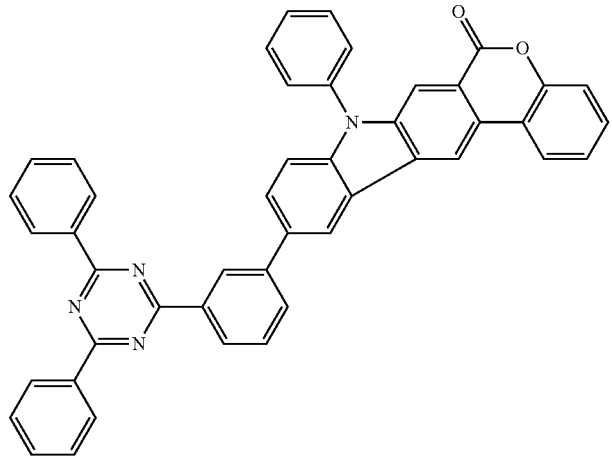 [SMILES: O=c1oc2ccccc2c2cc3c4cc(-c5cccc(-c6nc(-c7ccccc7)nc(-c7ccccc7)n6)c5)ccc4n(-c4ccccc4)c3cc12]
IP32
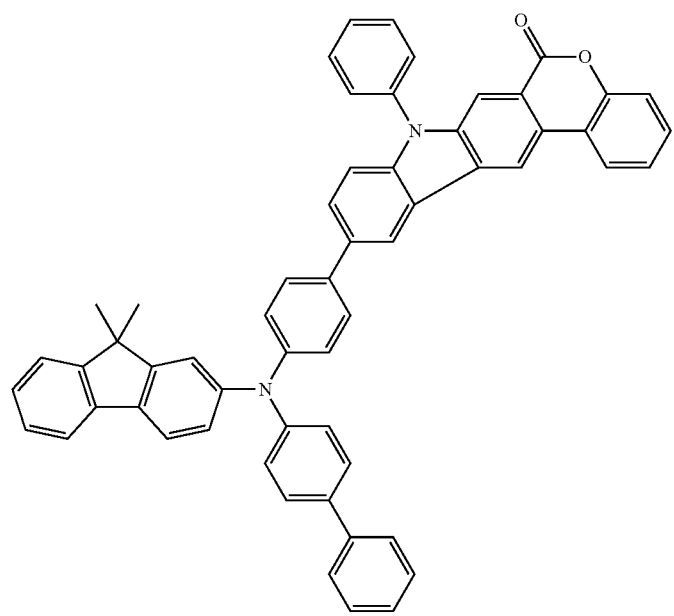 [SMILES: CC1(C)c2ccccc2-c2ccc(N(c3ccc(-c4ccccc4)cc3)c3ccc(-c4ccc5c(c4)c4cc6c(cc4n5-c4ccccc4)c(=O)oc4ccccc46)cc3)cc21]
IP33

TABLE 3-continued
Structural formulae of the materials for the OLEDs
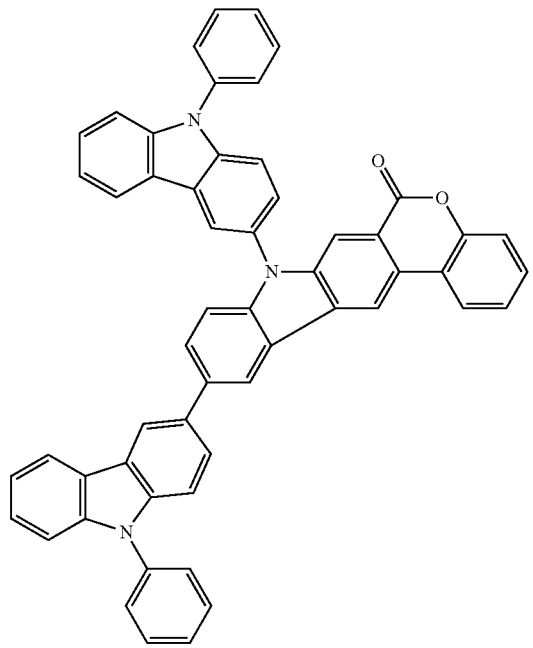 [SMILES: O=c1oc2ccccc2c2cc3c4cc(-c5ccc6c(c5)c5ccccc5n6-c5ccccc5)ccc4n(-c4ccc5c(c4)c4ccccc4n5-c4ccccc4)c3cc12]
IP34
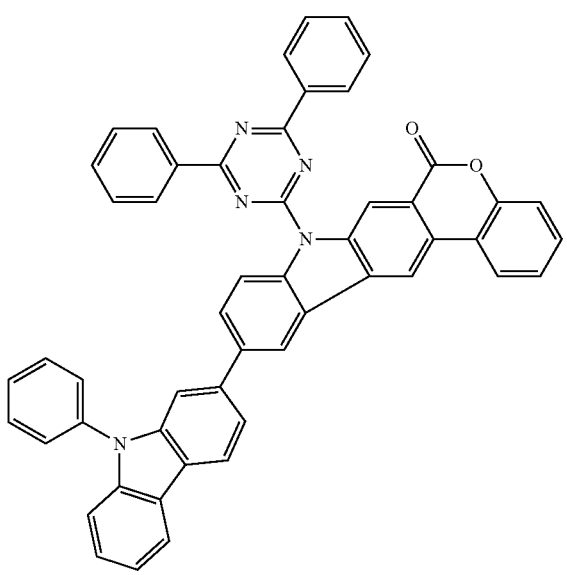 [SMILES: O=c1oc2ccccc2c2cc3c4cc(-c5ccc6c7ccccc7n(-c7ccccc7)c6c5)ccc4n(-c4nc(-c5ccccc5)nc(-c5ccccc5)n4)c3cc12]
IP35

The invention claimed is:
1. A compound of formula (1) or formula (2)

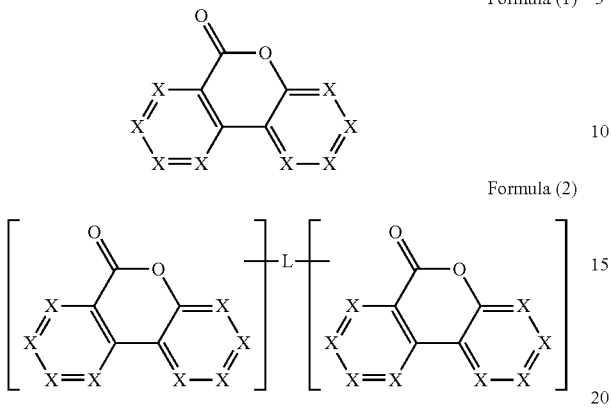

where the symbols used are as follows:
X is the same or different at each instance and is CR or N or two adjacent X groups are a group of the following formula (3):

Formula (3)

where ^ indicates the corresponding adjacent X groups in the formula (1) or formula (2), with the proviso that the compound of the formula (1) or formula (2) contains at least one group of the formula (3);
Z is the same or different at each instance and is CR or N;
L is a single bond or a bivalent group, where L is bonded in place of an R or $R^1$ group;
R is the same or different at each instance and is selected from the group consisting of H; D; F; Cl; Br; I; CN; $NO_2$; $N(Ar^1)_2$; $N(R^2)_2$; $C(=O)Ar^1$; $C(=O)R^2$; $P(=O)(Ar^1)_2$; $P(Ar^1)_2$; $B(Ar^1)_2$; $Si(Ar^1)_3$; $Si(R^2)_3$; a straight-chain alkyl, alkoxy or thioalkyl group having 1 to 40 carbon atoms; a branched or cyclic alkyl, alkoxy or thioalkyl group having 3 to 40 carbon atoms; an alkenyl or alkynyl group having 2 to 40 carbon atoms; wherein each of the alkyl, alkoxy thioalkyl, alkenyl and alkynyl group is optionally substituted by one or more $R^2$ radicals, where one or more nonadjacent $CH_2$ groups of the alkyl, alkoxy thioalkyl, alkenyl and alkynyl group is optionally replaced by $R^2C=CR^2$, C≡C, $Si(R^2)_2$, C=O, C=S, $C=NR^2$, $P(=O)(R^2)$, SO, $SO_2$, $NR^2$, O, S or $CONR^2$ and where one or more hydrogen atoms of the alkyl, alkoxy thioalkyl, alkenyl and alkynyl group is optionally replaced by D, F, Cl, Br, I, CN or $NO_2$; an aromatic or heteroaromatic ring system which has 5 to 60 aromatic ring atoms and wherein the aromatic or heteroaromatic ring is optionally substituted in each case by one or more $R^2$ radicals; an aryloxy or heteroaryloxy group which has 5 to 60 aromatic ring atoms and wherein the aryloxy or heteroaryloxy group is optionally substituted by one or more $R^2$ radicals; it is optionally possible for two adjacent R substituents to form a monocyclic or polycyclic, aliphatic, aromatic or heteroaromatic ring system which is optionally substituted by one or more $R^2$ radicals;
$R^1$ is the same or different at each instance and is selected from the group consisting of an aromatic or heteroaromatic ring system which has 5 to 60 aromatic ring atoms and is optionally substituted in each case by one or more $R^2$ radicals;
$Ar^1$ is the same or different at each instance and is an aromatic or heteroaromatic ring system which has 5-30 aromatic ring atoms and is optionally substituted by one or more nonaromatic $R^2$ radicals; two $Ar^1$ radicals bonded to the same nitrogen atom or phosphorus atom may also be bridged to one another by a single bond or a bridge selected from $N(R^2)$, $C(R^2)_2$, O and S; and
$R^2$ is the same or different at each instance and is selected from the group consisting of H; D; F; CN; an aliphatic hydrocarbyl radical having 1 to 20 carbon atoms and an aromatic or heteroaromatic ring system having 5 to 30 aromatic ring atoms wherein one or more hydrogen atoms of the aromatic or heteroaromatic ring system is optionally replaced by D, F, Cl, Br, I or CN, where two or more adjacent $R^2$ substituents together may form a mono- or polycyclic, aliphatic ring system.

2. The compound as claimed in claim 1, wherein the compound is a compound of the formula (4) or formula (5)

Formula (4)

Formula (5)

where X is as defined in claim 1 and $X^1$ is the same or different at each instance and is CR or N and R is as defined in claim 1.

3. The compound as claimed in claim 1, wherein the compound is a compound of the formulae (6) to (17)

Formula (6)

Formula (7)

Formula (8)
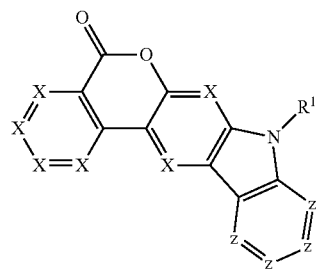
Formula (9)
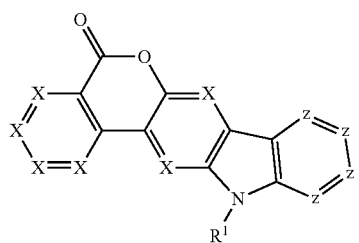
Formula (10)
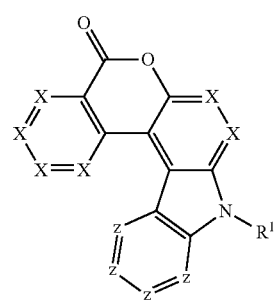
Formula (11)
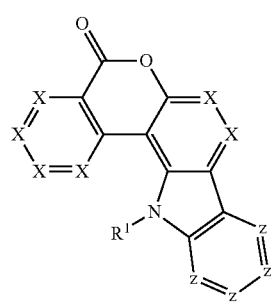
Formula (12)
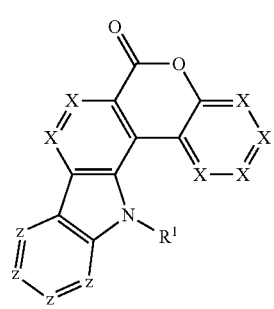
Formula (13)
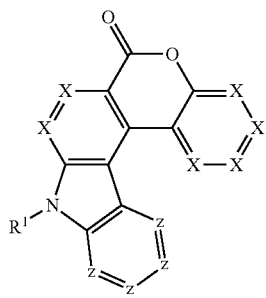
Formula (14)
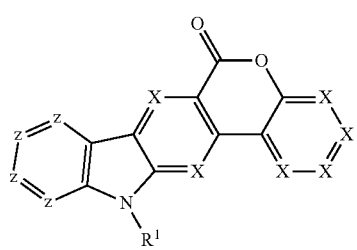
Formula (15)
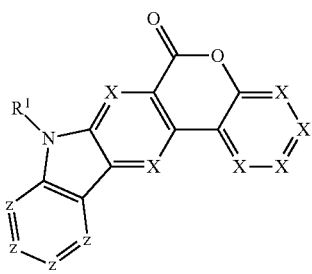
Formula (16)
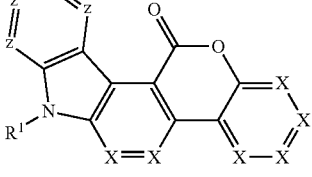
Formula (17)
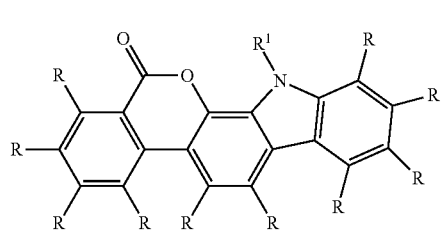
where the symbols used have the same definition as described in claim 1, and X is the same or different at each instance and is CR or N and R is as defined in claim 1.
4. The compound as claimed in claim 1, wherein the compound is a compound of the formulae (6a) to (17a)
Formula (6a)

Formula (7a)
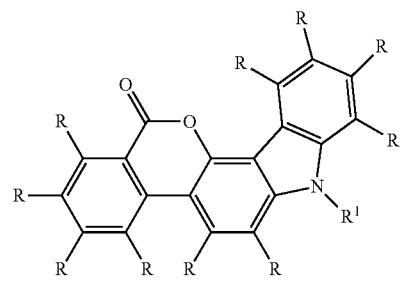
Formula (8a)
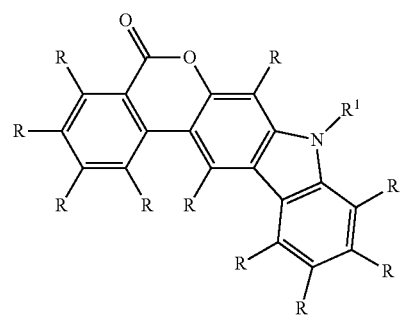
Formula (9a)
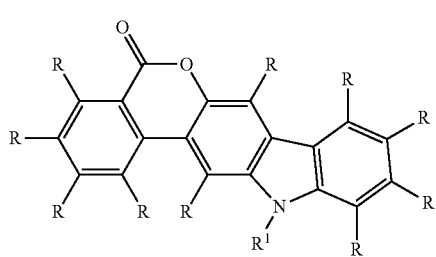
Formula (10a)
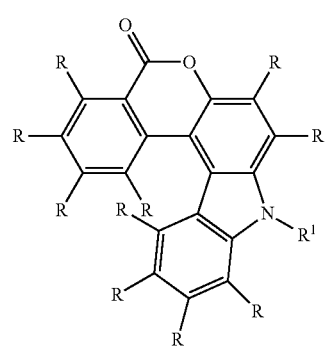
Formula (11a)
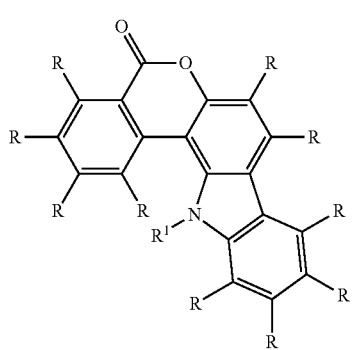
Formula (12a)
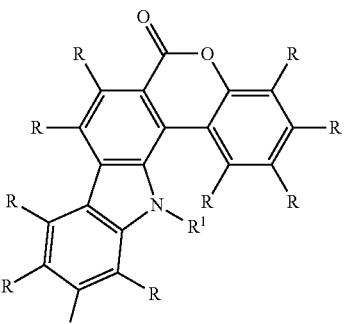
Formula (13a)
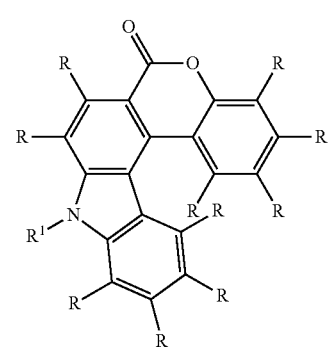
Formula (14a)
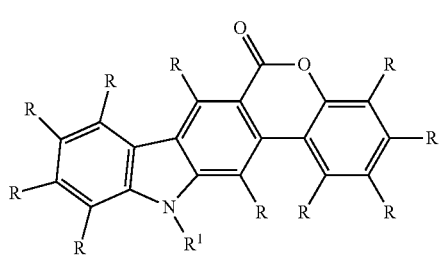
Formula (15a)
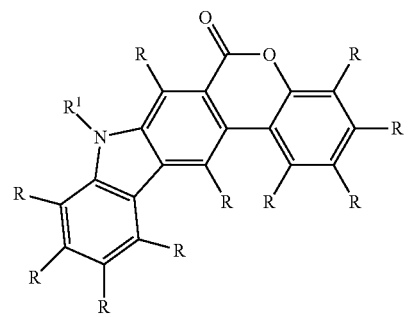
Formula (16a)
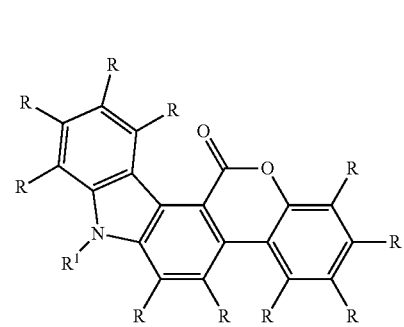

Formula (17a)
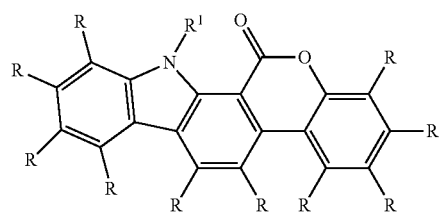
where the symbols used have the same definitions as described in claim 1.
5. The compound as claimed in claim 1, selected from the compounds of the formulae (6b) to (17b)
Formula (6b)
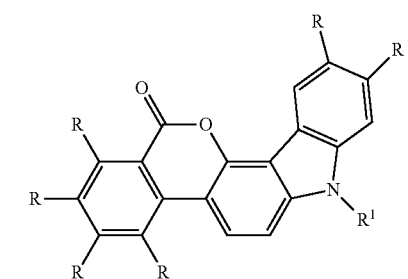
Formula (7b)
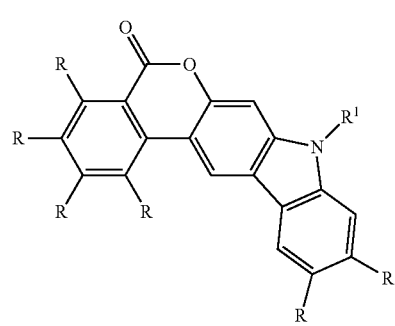
Formula (8b)
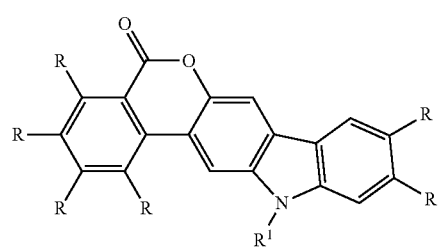
Formula (9b)
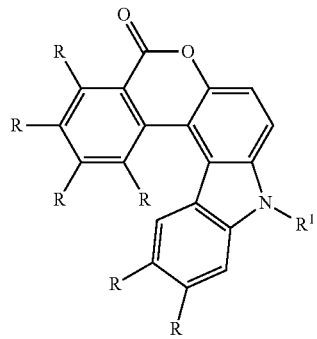
Formula (10b)
Formula (11b)
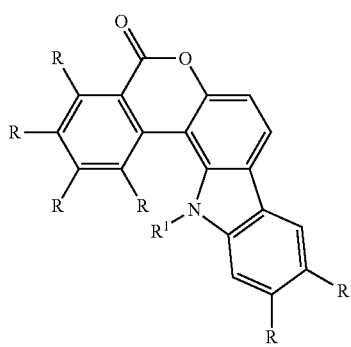
Formula (12b)
Formula (13b)
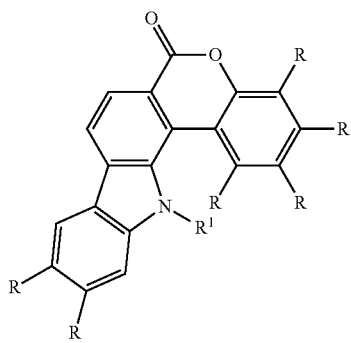
Formula (14b)
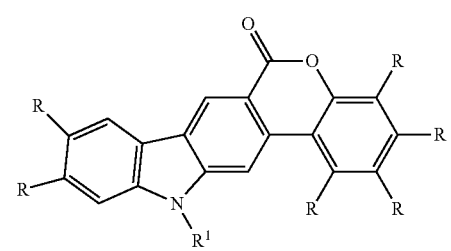

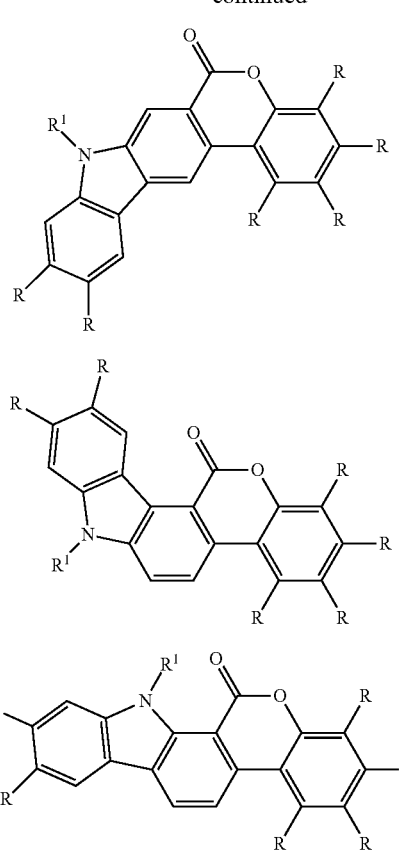

Formula (15b)

Formula (16b)

Formula (17b)

where the symbols used have the same definitions as described in claim 1.

6. The compound as claimed in claim 1, wherein, in compounds of the formula (2), the bivalent L group is bonded to the nitrogen atom of the formula (3).

7. The compound as claimed in claim 1, wherein L is selected from the group consisting of a single bond, a straight-chain alkylene group having 1 to 10 carbon atoms, a branched or cyclic alkylene group having 3 to 10 carbon atoms, an aromatic or heteroaromatic ring system which has 5 to 60 aromatic ring atoms and wherein the aromatic or heteroaromatic ring system is optionally substituted by one or more nonaromatic $R^2$ radicals wherein $R^2$ is H; D; F; CN; an aliphatic hydrocarbyl radical having 1 to 20 carbon atoms.

8. The compound as claimed in claim 1, wherein R is the same or different at each instance and is selected from the group consisting of H, F, CN, $N(Ar^1)_2$, a straight-chain alkyl group having 1 to 10 carbon atoms, a branched or cyclic alkyl group having 3 to 10 carbon atoms, an aromatic or heteroaromatic ring system which has 5 to 30 aromatic ring atoms and is optionally substituted by one or more nonaromatic $R^2$ radicals wherein $R^2$ is H; D; F; CN; an aliphatic hydrocarbyl radical having 1 to 20 carbon atoms.

9. The compound as claimed in claim 1, wherein, in compounds of the formula (2), the bivalent L group is bonded to the carbon atom para to the nitrogen atom in formula (3).

10. The compound as claimed in claim 1, wherein $R^1$ is the same or different at each instance and is selected from benzene; ortho-, meta- or para-biphenyl; ortho-, meta-, para- or branched terphenyl; ortho-, meta-, para- or branched quaterphenyl; 1-, 2-, 3- or 4-fluorenyl; 1-, 2-, 3- or 4-spiro-bifluorenyl; 1- or 2-naphthyl; pyrrole; furan; thiophene; indole; benzofuran; benzothiophene; 1-, 2-, 3- or 4-carbazole; 1-, 2-, 3- or 4-dibenzofuran; 1-, 2-, 3- or 4-dibenzothiophene; indenocarbazole; indolocarbazole; 2-, 3- or 4-pyridine; 2-, 4- or 5-pyrimidine; pyrazine; pyridazine; triazine; anthracene; phenanthrene; triphenylene; pyrene; benzanthracene and combinations of two or three of these groups, each of which is optionally substituted by one or more $R^2$ radicals wherein $R^2$ has the same definition as described in claim 1.

11. A process for preparing the compound as claimed in claim 1, comprising the reaction steps of:
    a) synthesizing the base skeleton of the corresponding indolodibenzopyranone derivative unsubstituted on the indole nitrogen atom; and
    b) introducing the substituent on the indole nitrogen atom.

12. An oligomer, polymer or dendrimer containing one or more of the compounds as claimed in claim 1, wherein one or more bonds of the compound to the polymer, oligomer or dendrimer are present in place of substituents at one or more positions.

13. A formulation comprising at least one compound as claimed in claim 1 and at least one further compound and/or a solvent.

14. A formulation comprising the oligomer, polymer or dendrimer as claimed in claim 12 and at least one further compound and/or a solvent.

15. An electronic device comprising the compound as claimed in claim 1.

16. An electronic device comprising the oligomer, polymer or dendrimer as claimed in claim 12.

17. An electronic device selected from the group consisting of organic electroluminescent devices, organic integrated circuits, organic field-effect transistors, organic thin-film transistors, organic light-emitting transistors, organic solar cells, dye-sensitized organic solar cells, organic optical detectors, organic photoreceptors, organic field-quench devices, light-emitting electrochemical cells, organic laser diodes and organic plasmon emitting devices, comprising at least one compound as claimed in claim 1.

18. An electronic device selected from the group consisting of organic electroluminescent devices, organic integrated circuits, organic field-effect transistors, organic thin-film transistors, organic light-emitting transistors, organic solar cells, dye-sensitized organic solar cells, organic optical detectors, organic photoreceptors, organic field-quench devices, light-emitting electrochemical cells, organic laser diodes and organic plasmon emitting devices, comprising the oligomer, polymer or dendrimer as claimed in claim 12.

19. An organic electroluminescent device, comprising the compound as claimed in claim 1, is used as a matrix material for phosphorescent or fluorescent emitters
    i) in an emitting layer, and/or
    ii) in an electron-blocking or exciton-blocking layer, and/or
    iii) in a hole transport layer, and/or
    iv) in a hole blocker layer or
    v) electron transport layer.

* * * * *